(12) United States Patent
Roh et al.

(10) Patent No.: US 11,547,486 B1
(45) Date of Patent: Jan. 10, 2023

(54) DIGITAL IMAGE ANALYSIS FOR ROBOTIC INSTALLATION OF SURGICAL IMPLANTS

(71) Applicant: IX Innovation LLC, Seattle, WA (US)

(72) Inventors: Jeffrey Roh, Seattle, WA (US); Justin Esterberg, Mesa, AZ (US); John Cronin, Jericho, VT (US); Seth Cronin, Essex Junction, VT (US); Michael John Baker, Georgia, VT (US)

(73) Assignee: IX Innovation LLC, Seattle, WA (US)

( * ) Notice: Subject to any disclaimer, the term of this patent is extended or adjusted under 35 U.S.C. 154(b) by 0 days.

(21) Appl. No.: 17/879,979

(22) Filed: Aug. 3, 2022

(51) Int. Cl.
| | | |
|---|---|---|
| *G06F 17/00* | (2019.01) | |
| *A61B 34/10* | (2016.01) | |
| *A61B 34/37* | (2016.01) | |
| *G06T 7/11* | (2017.01) | |
| *B25J 9/16* | (2006.01) | |

(52) U.S. Cl.
CPC .............. *A61B 34/10* (2016.02); *A61B 34/37* (2016.02); *B25J 9/1671* (2013.01); *G06T 7/11* (2017.01); *A61B 2034/102* (2016.02); *A61B 2034/105* (2016.02); *A61B 2034/107* (2016.02); *A61B 2034/108* (2016.02); *G06T 2207/30052* (2013.01)

(58) Field of Classification Search
CPC ... A61B 34/10; A61B 34/37; A61B 2034/102; A61B 2034/105; A61B 2034/107; A61B 2034/108; B25J 9/1671; G06T 7/11; G06T 2207/30052

USPC .......................................................... 700/246
See application file for complete search history.

(56) References Cited

U.S. PATENT DOCUMENTS

| | | | | |
|---|---|---|---|---|
| 9,820,818 | B2* | 11/2017 | Malackowski | A61B 34/20 |
| 10,105,168 | B2* | 10/2018 | Blau | A61B 17/1721 |
| 10,426,560 | B2* | 10/2019 | Bowling | A61B 34/30 |
| 10,806,517 | B2* | 10/2020 | Bonny | A61B 17/1703 |
| 10,987,175 | B2* | 4/2021 | Britton | A61B 34/30 |
| 11,045,958 | B2* | 6/2021 | Bowling | B25J 13/00 |
| 11,160,580 | B2* | 11/2021 | Hua | A61B 17/7091 |
| 11,179,210 | B2* | 11/2021 | Bowling | B25J 13/00 |
| 11,298,244 | B2* | 4/2022 | Schultz | A61F 2/30749 |
| 11,432,828 | B1* | 9/2022 | Lang | A61B 17/1622 |
| 11,471,232 | B2* | 10/2022 | Bowling | A61B 34/74 |
| 2016/0242931 | A1* | 8/2016 | Wong | A61B 34/10 |
| 2021/0186614 | A1* | 6/2021 | Forstein | A61B 5/6878 |
| 2021/0282858 | A1* | 9/2021 | Hill | G16H 50/50 |
| 2021/0308872 | A1* | 10/2021 | Bowling | A61B 34/10 |
| 2021/0391058 | A1* | 12/2021 | Kostrzewski | G16H 20/40 |
| 2022/0338886 | A1* | 10/2022 | Bonny | A61B 17/1764 |

\* cited by examiner

*Primary Examiner* — Ronnie M Mancho
(74) *Attorney, Agent, or Firm* — Perkins Coie LLP

(57) ABSTRACT

Computer-implemented digital image analysis methods, apparatuses, and systems for robotic installation of surgical implants are disclosed. A disclosed apparatus plans a route within an anatomy of a patient from an incision site to a surgical implant site for robotic installation of a surgical implant. The apparatus uses digital imaging data to identify less-invasive installation paths and determine the dimensions of the surgical implant components being used. The apparatus segments the surgical implant into surgical implant subcomponents and modifies the surgical implant subcomponents, such that they can be inserted using the identified less-invasive installation paths.

20 Claims, 14 Drawing Sheets

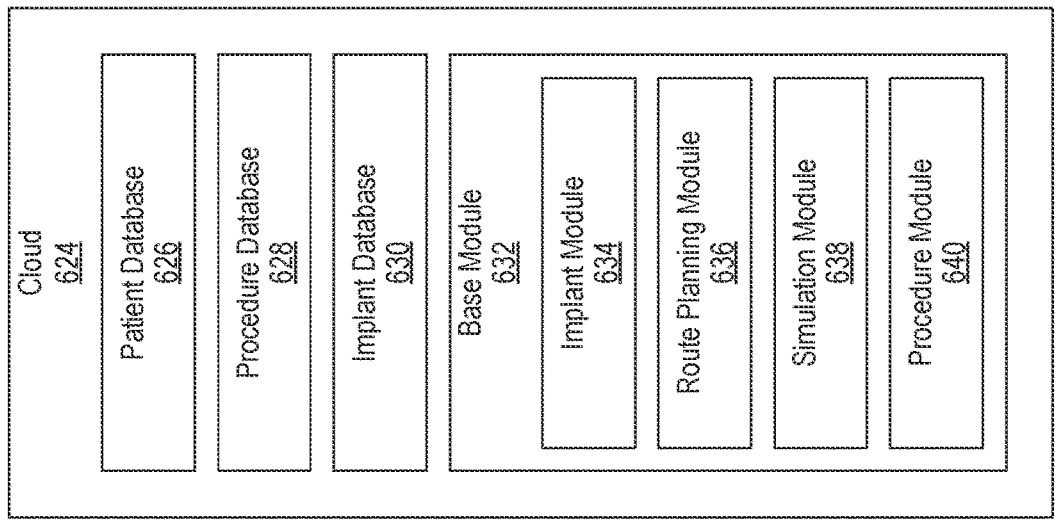
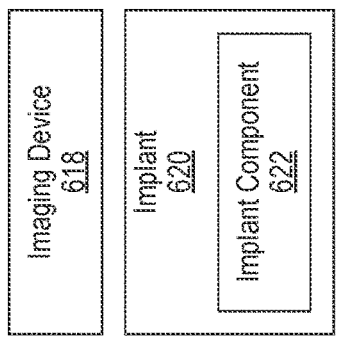
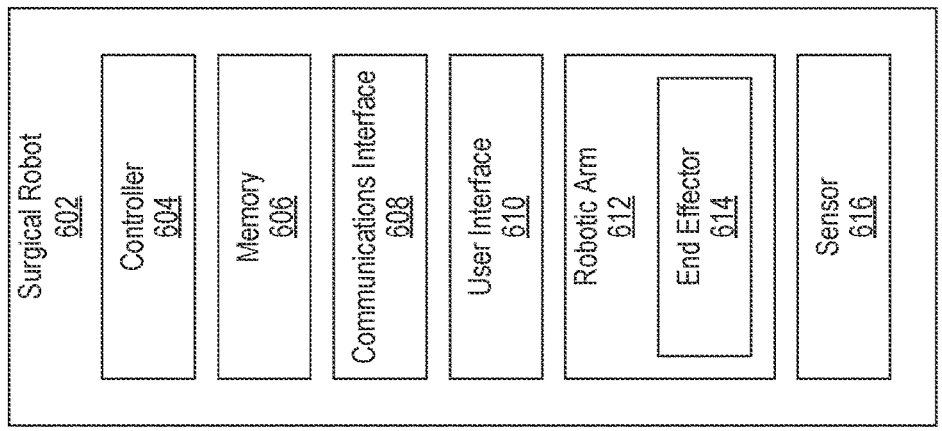
FIG. 6

| Patient ID | Age | Gender | Height (in.) | Allergies | Conditions | Image Files |
|---|---|---|---|---|---|---|
| M_0026 | 46 | Male | 70 | None | None | MRI_pelvis_3-20-2022 |
| F_0165 | 36 | Female | 65 | None | None | XRAY_r-knee_2-4-2022 |
| F_0654 | 48 | Female | 68 | Latex | Breast Cancer | CT_chest_1-5-2022 |
| M_0264 | 65 | Male | 72 | None | Coronary Heart Disease | CT_chest_2-16-2022 |
| F_0544 | 72 | Female | 63 | None | Osteoporosis | XRAY_pelvis_2-25-2022 |

*FIG. 7*

| Procedure ID | Patient ID | Surgeon ID | Procedure |
|---|---|---|---|
| 465463 | M_0026 | 1654 | Pelvis reconstruction |
| 847324 | F_0165 | 1548 | Knee replacement |
| 321698 | F_0654 | 1265 | Mastectomy and breast reconstruction |
| 765864 | M_0264 | 1874 | Triple bypass |
| 679465 | F_0544 | 1324 | Hip fracture repair |

*FIG. 8*

| Implant ID | Implant Component ID | Materials | Mechanisms | Width (cm) | Height (cm) | Length (cm) |
|---|---|---|---|---|---|---|
| A364 | 135 | Titanium Alloy | Butterfly hinges | 1.5 | 1 | 6 |
| A364 | 136 | Polypropylene | None | 2 | 1 | 3 |
| A364 | 137 | Cobalt-chromium Alloy | None | 1 | 2.5 | 5 |
| A364 | 138 | Medical-grade Silicone | None | 2 | 2 | 10 |
| A364 | 139 | Polyvinylchloride | None | 1 | 2 | 4 |
| A364 | 140 | Polyethylene | None | 1 | 2 | 4.5 |
| A364 | 141 | Polypropylene | None | 3 | 1.5 | 7 |
| A364 | 142 | Stainless Steel | Expanding mesh | 1 | 1 | 5 |
| A364 | 143 | Titanium | Telescoping tubing | 0.5 | 0.5 | 5 |
| A364 | 144 | Zirconia | None | 1.5 | 1.5 | 3 |

*FIG. 9*

DIGITAL IMAGE ANALYSIS FOR ROBOTIC INSTALLATION OF SURGICAL IMPLANTS

TECHNICAL FIELD

The present disclosure is generally related to digital image analysis for automated and robotic surgical procedures.

BACKGROUND

More than 200 million surgeries are performed worldwide each year, and recent reports reveal that adverse event rates for surgical conditions remain unacceptably high, despite traditional patient safety initiatives. Adverse events resulting from surgical interventions can be related to errors occurring before or after the procedure, as well as technical surgical errors during the operation. For example, adverse events can occur due to (i) a breakdown in communication within and among the surgical team, care providers, patients, and their families; (ii) delays in diagnosis or failure to diagnose; and (iii) delays in treatment or failure to treat. The risk of complications during surgery can include anesthesia complications, hemorrhaging, high blood pressure, a rise or fall in body temperature, etc. Such adverse events can further occur due to medical errors, infections, underlying physical or health conditions of the patient, reactions to anesthetics or other drugs, etc. Conventional methods for preventing wrong-site, wrong-person, wrong-procedure errors, or retained foreign objects are typically based on communication between the patient, the surgeon(s), and other members of the health care team. However, conventional methods are typically insufficient to prevent surgical errors and adverse events during surgery.

BRIEF DESCRIPTION OF THE DRAWINGS

FIG. 6 is a block diagram illustrating an example robotic surgical system, in accordance with one or more embodiments.

FIG. 7 illustrates a structure of an example database for performing route planning for robotic surgical implant installation, in accordance with one or more embodiments.

FIG. 8 illustrates a structure of an example database for performing route planning for robotic surgical implant installation, in accordance with one or more embodiments.

FIG. 9 illustrates a structure of an example database for performing route planning for robotic surgical implant installation, in accordance with one or more embodiments.

DETAILED DESCRIPTION

Figure 1:
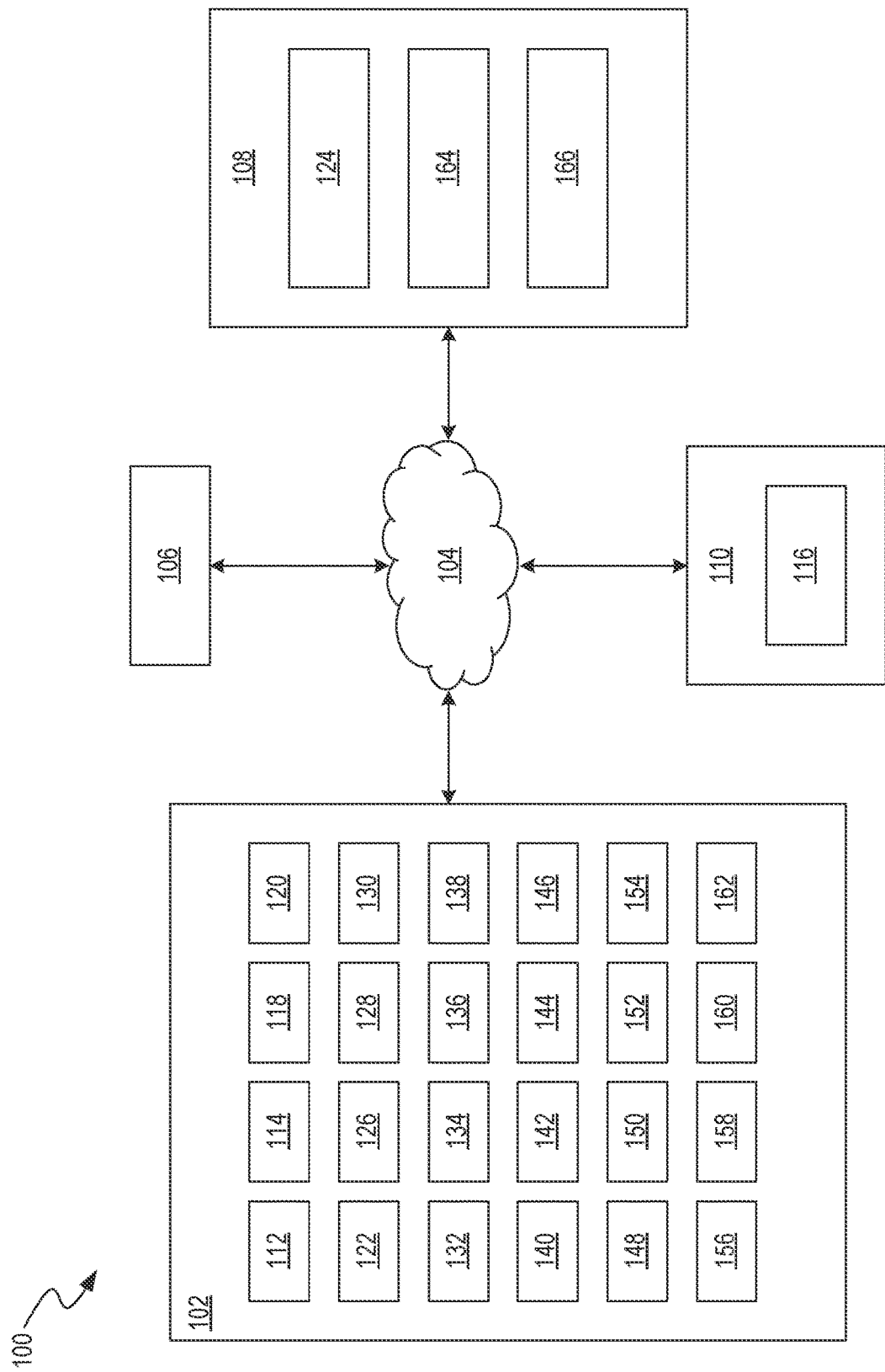
FIG. 1 is a block diagram illustrating an example surgical system, in accordance with one or more embodiments.

Embodiments of the present disclosure will be described more thoroughly from now on with reference to the accompanying drawings. Like numerals represent like elements throughout the several figures, and in which example embodiments are shown. However, embodiments of the claims can be embodied in many different forms and should not be construed as limited to the embodiments set forth herein. The examples set forth herein are non-limiting examples and are merely examples, among other possible examples. Throughout this specification, plural instances (e.g., "610") can implement components, operations, or structures (e.g., "610a") described as a single instance. Further, plural instances (e.g., "610") refer collectively to a set of components, operations, or structures (e.g., "610a") described as a single instance. The description of a single component (e.g., "610a") applies equally to a like-numbered component (e.g., "610b") unless indicated otherwise. These and other aspects, features, and implementations can be expressed as methods, apparatuses, systems, components, program products, means or steps for performing a function, and in other ways. These and other aspects, features, and implementations will become apparent from the following descriptions, including the claims.

The embodiments disclosed herein provide computer-implemented digital image analysis methods for robotic installation of surgical implants. The embodiments enable the visualization and maneuvering of surgical implants within a patient's body for minimally invasive surgery. Traditional surgery methods can sometimes result in unintended harm to a patient because of the difficulty or inability to visualize a surgical tool's movements within the patient's body. For example, traditional laparoscopic procedures typically use rigid tool extensions to maneuver within a patient's body that can limit movement and cause internal injury to the patient. For traditional surgical methods to access a desired surgical site within or on a patient's body, success requires not only proper location of the incisions but also sufficient space to maneuver tools into required positions and orientations.

Further, the disclosed embodiments herein describe methods, apparatuses, and systems for route planning for robotic surgical implant installation. The disclosed apparatus plans a route within a patient's body from an incision site to a surgical implant site to enable the installation of a surgical implant within the patient's body. The disclosed system uses imaging data to identify a less-invasive installation path, and determines the dimensions of the surgical implant components being used. The system segments the surgical implant into surgical implant subcomponents, and modifies the surgical implant subcomponents, such that they can be inserted using the identified less invasive installation path.

In some embodiments, a method of determining a route for installing an artificial structure (e.g., a surgical implant or a surgical implant component) in a patient's body using minimally invasive techniques includes imaging the patient's body to obtain at least one image of the patient. A surgical implant is segmented into multiple implant components. An incision site and an implant site in the patient's body are identified. At least two separate routes are identified between the incision site and the implant site for the implant components to pass through. Based on the identified routes, the system determines at least one surgical movement modality for the surgical implant segments. Movement of the implant components using the at least one surgical movement modality through the identified routes is simulated. The system identifies at least one route through which at least one surgical implant component can be navigated from the incision site to the implant site using the surgical movement modality.

The advantages and benefits of the methods, systems, and apparatuses disclosed herein include compatibility with best practice guidelines for performing surgery in an operating room, e.g., from regulatory bodies and professional standards organizations such as the Association for Surgical Technologists. The systems for route planning for robotic surgical implant installation disclosed use computer networks, the Internet, intranets, and supporting technologies to implement a cost-effective technology to collect, transmit, store, analyze, and use information in electronic formats. The disclosed embodiments especially facilitate the robotic installation of surgical implants without requiring larger incisions in the patient's body, thus improving healing and recovery times.

The disclosed methods enable the installation and assembly of surgical implants using implant components, e.g., metal rods, plates, or screws. The modularity provided by the embodiments improves a surgical robot's flexibility in managing the variability in physiology between patients. Further, the disclosed apparatuses enable treatment of a wider range of physiological defects. The disclosed surgical systems use the modularity and design of surgical implant components to reduce the impact on the patient to improve recovery times. Moreover, the disclosed embodiments reduce injury to the patient's body by reducing incision sizes and preventing internal injury while navigating through the patient's body during installation of a surgical implant. Thus, patient recovery times are improved. The disclosed route planning methods to navigate the patient's unique physiology further enables improved procedure times while reducing harm to the patient. The disclosed surgical implant designs when paired with image-based route planning enable minimally invasive implantation of even complex surgical implants. In addition, the advantages of the convolutional neural network (CNN) used for machine learning (ML) in the disclosed embodiments include the obviation of feature extraction and the use of shared weight in convolutional layers, which means that the same filter (weights bank) is used for each node in the layer; this both reduces memory footprint and improves performance.

FIG. 1 is a block diagram illustrating an example surgical system 100, in accordance with one or more embodiments. The system 100 includes various surgical and medical equipment (e.g., a patient monitor 112) located within an operating room 102 or a doctor's office 110, a console 108 for performing surgery or other patient care, and a database 106 for storing electronic health records. The console 108 is the same as or similar to the console 420 illustrated and described in more detail with reference to FIG. 4A. The system 100 is implemented using the components of the example computer system 300 illustrated and described in more detail with reference to FIG. 3. Likewise, embodiments of the system 100 can include different and/or additional components or can be connected in different ways.

The operating room 102 is a facility, e.g., within a hospital, where surgical operations are carried out in an aseptic environment. Proper surgical procedures require a sterile field. In some embodiments, the sterile field is maintained in the operating room 102 in a medical care facility such as a hospital, the doctor's office 110, or an outpatient surgery center.

In some embodiments, the system 100 includes one or more medical or surgical patient monitors 112. The monitors 112 can include a vital signs monitor (a medical diagnostic instrument), which can be a portable, battery-powered, multi-parametric, vital signs monitoring device used for both ambulatory and transport applications as well as bedside monitoring. The vital signs monitor can be used with an isolated data link to an interconnected portable computer or the console 108, allowing snapshot and trended data from the vital signs monitor to be printed automatically at the console 108, and also allowing default configuration settings to be downloaded to the vital signs monitor. The vital signs monitor is capable of use as a stand-alone unit as well as part of a bi-directional wireless communications network that includes at least one remote monitoring station (e.g., the console 108). The vital signs monitor can measure multiple physiological parameters of a patient wherein various sensor output signals are transmitted either wirelessly or by means of a wired connection to at least one remote site, such as the console 108.

In some embodiments, the monitors 112 include a heart rate monitor, which is a sensor and/or a sensor system applied in the context of monitoring heart rates. The heart rate monitor measures, directly or indirectly, any physiological condition from which any relevant aspect of heart rate can be gleaned. For example, some embodiments of the heart rate monitor measure different or overlapping physiological conditions to measure the same aspect of heart rate. Alternatively, some embodiments measure the same, different, or overlapping physiological conditions to measure different aspects of heart rate, e.g., number of beats, strength of beats, regularity of beats, beat anomalies, etc.

In some embodiments, the monitors 112 include a pulse oximeter or SpO2 monitor, which is a plethysmograph or any instrument that measures variations in the size of an organ or body part of the patient on the basis of the amount of blood passing through or present in the body part. The pulse oximeter is a type of plethysmograph that determines the oxygen saturation of the blood by indirectly measuring the oxygen saturation of the patient's blood (as opposed to measuring oxygen saturation directly through a blood sample) and changes in blood volume in the skin. The pulse oximeter can include a light sensor that is placed at a site on the patient, usually a fingertip, toe, forehead, or earlobe, or in the case of a neonate, across a foot. Light, which can be produced by a light source integrated into the pulse oximeter, containing both red and infrared wavelengths, is directed onto the skin of the patient, and the light that passes through the skin is detected by the pulse oximeter. The intensity of light in each wavelength is measured by the pulse oximeter over time. The graph of light intensity versus time is referred to as the photoplethysmogram (PPG) or, more commonly, simply as the "pleth." From the waveform of the PPG, it is possible to identify the pulse rate of the patient and when each individual pulse occurs. In addition, by comparing the intensities of two wavelengths when a pulse occurs, it is possible to determine blood oxygen saturation of hemoglobin in arterial blood. This relies on the observation that highly oxygenated blood will relatively absorb more red light and less infrared light than blood with a lower oxygen saturation.

In some embodiments, the monitors 112 include an end-tidal CO2 monitor or capnography monitor used for measurement of the level of carbon dioxide that is released at the end of an exhaled breath (referred to as end-tidal carbon dioxide, ETCO2). An end-tidal CO2 monitor or capnography monitor is widely used in anesthesia and intensive care. ETCO2 can be calculated by plotting expiratory CO2 with time. Further, ETCO2 monitors are important for the measurement of applications such as cardiopulmonary resuscitation (CPR), airway assessment, procedural sedation and analgesia, pulmonary diseases such as obstructive pulmonary disease, pulmonary embolism, etc., heart failure, metabolic disorders, etc. The end-tidal CO2 monitor can be configured as side stream (diverting) or mainstream (non-diverting). A diverting end-tidal CO2 monitor transports a portion of a patient's respired gases from the sampling site to the end-tidal CO2 monitor, while a non-diverting end-tidal CO2 monitor does not transport gas away. Also, measurement by the end-tidal CO2 monitor is based on the absorption of infrared light by carbon dioxide where exhaled gas passes through a sampling chamber containing an infrared light source and photodetector on both sides. Based on the amount of infrared light reaching the photodetector, the amount of carbon dioxide present in the gas can be determined.

In some embodiments, the monitors 112 include a blood pressure monitor that measures blood pressure, particularly in arteries. The blood pressure monitor uses a non-invasive technique (by external cuff application) or an invasive technique (by a cannula needle inserted in an artery, used in the operating room 102) for measurement. The non-invasive method (referred to as a sphygmomanometer) works by measurement of force exerted against arterial walls during (i) ventricular systole (i.e., systolic blood pressure occurs when the heart beats and pushes blood through the arteries) and (ii) ventricular diastole (i.e., diastolic blood pressure occurs when the heart rests and is filling with blood) thereby measuring systole and diastole, respectively. The blood pressure monitor can be of three types: automatic/digital, manual (aneroid-dial), and manual (mercury-column). The sphygmomanometer can include a bladder, a cuff, a pressure meter, a stethoscope, a valve, and a bulb. The cuff inflates until it fits tightly around the patient's arm, cutting off the blood flow, and then the valve opens to deflate it. The blood pressure monitor operates by inflating a cuff tightly around the arm; as the cuff reaches the systolic pressure, blood begins to flow in the artery, creating a vibration, which is detected by the blood pressure monitor, which records the systolic pressure. The techniques used for measurement can be auscultatory or oscillometric.

In some embodiments, the monitors 112 include a body temperature monitor. The body temperature monitor measures the temperature invasively or non-invasively by placement of a sensor into organs such as the bladder, rectum, esophagus, tympanum, etc., and mouth, armpit, etc., respectively. The body temperature monitor is of two types: contact and non-contact. Temperature can be measured in two forms: core temperature and peripheral temperature. Temperature measurement can be done by thermocouples, resistive temperature devices (RTDs, thermistors), infrared radiators, bimetallic devices, liquid expansion devices, molecular change-of-state, and silicon diodes. A body temperature monitor commonly used for the measurement of temperature includes a temperature sensing element (e.g., temperature sensor) and a means for converting to a numerical value.

In some embodiments, the monitors 112 measure respiration rate or breathing rate—the rate at which breathing occurs—and which is measured by the number of breaths the patient takes per minute. The rate is measured when a person is at rest and simply involves counting the number of breaths for one minute by counting how many times the chest rises. Normal respiration rates for an adult patient at rest are in the range: 12 to 16 breaths per minute. A variation can be an indication of an abnormality/medical condition or the patient's demographic parameters. The monitors 112 can indicate hypoxia, a condition with low levels of oxygen in the cells, or hypercapnia, a condition in which high levels of carbon dioxide are in the bloodstream. Pulmonary disorders, asthma, anxiety, pneumonia, heart diseases, dehydration, and drug overdose are some abnormal conditions, which can cause a change to the respiration rate, thereby increasing or reducing the respiration rate from normal levels.

In some embodiments, the monitors 112 measure an electrocardiogram (EKG or ECG), a representation of the electrical activity of the heart (graphical trace of voltage versus time) by placement of electrodes on the skin/body surface. The electrodes capture the electrical impulse, which travels through the heart causing systole and diastole or the pumping of the heart. This impulse provides information related to the normal functioning of the heart and the production of impulses. A change can occur due to medical conditions such as arrhythmias (tachycardia, where the heart rate becomes faster, and bradycardia, where the heart rate becomes slower), coronary heart disease, heart attacks, or cardiomyopathy. The instrument used for measurement of the electrocardiogram is called an electrocardiograph, which measures the electrical impulses by the placement of electrodes on the surface of the body and represents the ECG by a PQRST waveform. A PQRST wave is read as: P wave, which represents the depolarization of the left and right atrium and corresponds to atrial contraction; QRS complex, which indicates ventricular depolarization and represents the electrical impulse as it spreads through the ventricles; and T wave, which indicates ventricular repolarization and follows the QRS complex.

In some embodiments, the monitors 112 perform neuromonitoring, also called intraoperative neurophysiological monitoring (IONM). For example, the monitors 112 assess functions and changes in the brain, brainstem, spinal cord, cranial nerves, and peripheral nerves during a surgical procedure on these organs. Monitoring includes both continuous monitoring of neural tissue as well as the localization of vital neural structures. IONM measures changes in these organs where the changes are indicative of irreversible damage or injuries in the organs, aiming at reducing the risk of neurological deficits after operations involving the nervous system. Monitoring is effective in localization of anatomical structures, including peripheral nerves and the sensorimotor cortex, which helps in guiding a surgical robot during dissection. Electrophysiological modalities employed in neuromonitoring are an extracellular single unit and local field recordings (LFP), somatosensory evoked potential (SSEP), transcranial electrical motor evoked potentials (TCeMEP), electromyography (EMG), electroencephalography (EEG), and auditory brainstem response (ABR). The use of neurophysiological monitoring during surgical procedures requires anesthesia techniques to avoid interference and signal alteration due to anesthesia.

In some embodiments, the monitors 112 measure motor evoked potential (MEP), electrical signals that are recorded from descending motor pathways or muscles following stimulation of motor pathways within the brain. MEP is determined by measurement of the action potential elicited by non-invasive stimulation of the motor cortex through the scalp. MEP is for intraoperative monitoring and neurophysiological testing of the motor pathways specifically during spinal procedures. The technique of monitoring for measurement of MEP is defined based on parameters, such as a site of stimulation (motor cortex or spinal cord), method of stimulation (electrical potential or magnetic field), and site of recording (spinal cord or peripheral mixed nerve and muscle). The target site is stimulated by the use of electrical or magnetic means.

In some embodiments, the monitors 112 measure somatosensory evoked potential (SSEP or SEP): the electrical signals generated by the brain and the spinal cord in response to sensory stimulus or touch. SSEP is used for intraoperative neurophysiological monitoring in spinal surgeries. The measurements are reliable, which allows for continuous monitoring during a surgical procedure. The sensor stimulus commonly given to the organs can be auditory, visual, or somatosensory SEPs and applied on the skin, peripheral nerves of the upper limbs, lower limbs, or scalp. The stimulation technique can be mechanical, electrical (provides larger and more robust responses), or intraoperative spinal monitoring modality.

In some embodiments, the monitors 112 provide electromyography (EMG): the evaluation and recording of electrical signals or electrical activity of the skeletal muscles. An electromyography instrument, electromyograph, or electromyogram for the measurement of the EMG activity records electrical activity produced by skeletal muscles and evaluates the functional integrity of individual nerves. The nerves monitored by an EMG instrument can be intracranial, spinal, or peripheral nerves. The electrodes used for the acquisition of signals can be invasive or non-invasive electrodes. The technique used for measurement can be spontaneous or triggered. Spontaneous EMG refers to the recording of myoelectric signals such as compression, stretching, or pulling of nerves during surgical manipulation. Spontaneous EMG is recorded by the insertion of a needle electrode. Triggered EMG refers to the recording of myoelectric signals during stimulation of a target site such as a pedicle screw with incremental current intensities.

In some embodiments, the monitors 112 provide electroencephalography (EEG), measuring the electrical signals in the brain. Brain cells communicate with each other through electrical impulses. EEG can be used to help detect potential problems associated with this activity. An electroencephalograph is used for the measurement of EEG activity. Electrodes ranging from 8 to 16 pairs are attached to the scalp, where each pair of electrodes transmits a signal to one or more recording channels. EEG is a modality for intraoperative neurophysiological monitoring and assessing cortical perfusion and oxygenation during a variety of vascular, cardiac, and neurosurgical procedures. The waves produced by EEG are alpha, beta, theta, and delta.

In some embodiments, the monitors 112 include sensors, such as microphones or optical sensors, that produce images or video captured from at least one of multiple imaging devices, for example, cameras attached to manipulators or end effectors, cameras mounted to the ceiling or other surface above the surgical theater, or cameras mounted on a tripod or other independent mounting device. In some embodiments, the cameras are body worn by a surgical robot or other surgical staff, cameras are incorporated into a wearable device, such as an augmented reality device like Google Glass™, or cameras are integrated into an endoscopic, microscopic, or laparoscopic device. In some embodiments, a camera or other imaging device (e.g., ultrasound) present in the operating room 102 is associated with one or more areas in the operating room 102. The sensors can be associated with measuring a specific parameter of the patient, such as respiratory rate, blood pressure, blood oxygen level, heart rate, etc.

In some embodiments, the system 100 includes a medical visualization apparatus 114 used for visualization and analysis of objects (preferably two-dimensional (2D) or three-dimensional (3D) objects) in the operating room 102. The medical visualization apparatus 114 provides the selection of points at surfaces, selection of a region of interest, or selection of objects. The medical visualization apparatus 114 can also be used for diagnosis, treatment planning, intraoperative support, documentation, or educational purposes. The medical visualization apparatus 114 can further include microscopes, endoscopes/arthroscopes/laparoscopes, fiber optics, surgical lights, high-definition monitors, operating room cameras, etc. Two-dimensional (2D) or three-dimensional (3D) visualization software provides visual representations of scanned body parts via virtual models, offering significant depth and nuance to static two-dimensional medical images. The software facilitates improved diagnoses, narrowed surgical operation learning curves, reduced operational costs, and shortened image acquisition times.

In some embodiments, the system 100 includes an instrument 118 such as an endoscope, arthroscope, or laparoscope for minimally invasive surgery (MIS), in which procedures are performed by cutting a minimal incision in the body. An endoscope refers to an instrument used to visualize, diagnose, and treat problems inside hollow organs where the instrument is inserted through natural body openings such as the mouth or anus. An endoscope can perform a procedure as follows: a scope with a tiny camera attached to a long, thin tube is inserted. A surgical robot moves it through a body passageway or opening to see inside an organ. It can be used for diagnosis and surgery (such as for removing polyps from the colon). An arthroscope refers to an instrument used to visualize, diagnose, and treat problems inside a joint by a TV camera inserted through small portals/incisions and to perform procedures on cartilage, ligaments, tendons, etc. An arthroscope can perform the procedure as follows: a surgical robot makes a small incision in a patient's skin and inserts a pencil-sized instrument with a small lens and lighting system to magnify the target site (joint) and viewing of the interior of the joint by means of a miniature TV camera and then performs the procedure. A laparoscope refers to an instrument used to visualize, diagnose, and treat problems inside soft organs like the abdomen and pelvis by a TV camera inserted through small portals/incisions and to perform procedures.

In some embodiments, the system 100 includes fiber optics 120, which refer to flexible, transparent fiber made by drawing glass (silica) or plastic to a diameter slightly thicker than that of a human hair. Fiber optics 120 are arranged in bundles called optical cables and used to transmit light signals across long distances. Fiber optics 120 are used most often as a means to transmit light between the two ends of the fiber and find wide usage in the medical field. Traditional surgery requires sizable and invasive incisions to expose internal organs and operate on affected areas, but with fiber optics 120 much smaller surgical incisions can be performed. Fiber optics 120 contain components such as a core, cladding, and buffer coating. Fiber optics 120 can be inserted in hypodermic needles and catheters, endoscopes, operation theater tools, ophthalmological tools, and dentistry tools. Fiber optic sensors include a light source, optical fiber, external transducer, and photodetector. Fiber optic sensors can be intrinsic or extrinsic. Fiber optic sensors can be categorized into four types: physical, imaging, chemical, and biological.

In some embodiments, the system 100 includes surgical lights 122 (referred to as operating lights) that perform illumination of a local area or cavity of the patient. Surgical lights 122 play an important role in illumination before, during, and after a medical procedure. Surgical lights 122 can be categorized by lamp type as conventional (incandescent) and LED (light-emitting diode). Surgical lights 122 can be categorized by mounting configuration as ceiling-mounted, wall-mounted, or floor stand. Surgical lights 122 can be categorized by type as tungsten, quartz, xenon halogens, and/or LEDs. Surgical lights 122 include sterilizable handles, which allow a surgical robot to adjust light positions. Some important factors affecting surgical lights 122 can be illumination, shadow management (cast shadows and contour shadows), the volume of light, heat management, or fail-safe surgical lighting.

In some embodiments, the system 100 includes a surgical tower 128, e.g., used in conjunction with the robotic surgical system 160 disclosed herein, for MIS. The surgical tower 128 includes instruments used for performing MIS or surgery, which is performed by creating small incisions in the body. The instruments are also referred to as minimally invasive devices or minimally invasive access devices. The procedure of performing MIS can also be referred to as a minimally invasive procedure. MIS is a safer, less invasive, and more precise surgical procedure. Some medical procedures where the surgical tower 128 is useful and widely used are procedures for lung, gynecological, head and neck, heart, and urological conditions. MIS can be robotic or non-robotic/endoscopic. MIS can include endoscopic, laparoscopic, arthroscopic, natural orifice intraluminal, and natural orifice transluminal procedures. A surgical tower access device can also be designed as an outer sleeve and an inner sleeve that telescopingly or slidably engage with one another. When a telescope is used to operate on the abdomen, the procedure is called laparoscopy. The surgical tower 128 typically includes access to a variety of surgical tools, such as for electrocautery, radiofrequency, lasers, sensors, etc.

In some embodiments, radiofrequency (RF) is used in association with MIS devices. The RF can be used for the treatment of skin by delivering it to the skin through a minimally invasive surgical tool (e.g., fine needles), which does not require skin excision. The RF can be used for real-time tracking of MIS devices such as laparoscopic instruments. The RF can provide radiofrequency ablation to a patient suffering from atrial fibrillation through smaller incisions made between the ribs. The RF can be used to perform an endoscopic surgery on the body such as the spine by delivery of RF energy.

In some embodiments, the system 100 includes an instrument 130 to perform electrocautery for burning a part of the body to remove or close off a part of it. Various physiological conditions or surgical procedures require the removal of body tissues and organs, a consequence of which is bleeding. In order to achieve hemostasis and for removing and sealing all blood vessels that are supplied to an organ after surgical incision, the electrocautery instrument 130 can be used. For example, after removing part of the liver for removal of a tumor, etc., blood vessels in the liver must be sealed individually. The electrocautery instrument 130 can be used for sealing living tissue such as arteries, veins, lymph nodes, nerves, fats, ligaments, and other soft tissue structures. The electrocautery instrument 130 can be used in applications such as surgery, tumor removal, nasal treatment, or wart removal. Electrocautery can operate in two modes, monopolar or bipolar. The electrocautery instrument 130 can consist of a generator, a handpiece, and one or more electrodes.

In some embodiments, the system 100 includes a laser 132 used in association with MIS devices. The laser 132 can be used in MIS with an endoscope. The laser 132 is attached to the distal end of the endoscope and steered at high speed by producing higher incision quality than with existing surgical tools thereby minimizing damage to surrounding tissue. The laser 132 can be used to perform MIS using a laparoscope in the lower and upper gastrointestinal tract, eye, nose, and throat. The laser 132 is used in MIS to ablate soft tissues, such as a herniated spinal disc bulge.

In some embodiments, sensors 134 are used in association with MIS devices and the robotic surgical system 160 described herein. The sensors 134 can be used in MIS for tactile sensing of surgical tool-tissue interaction forces. During MIS, the field of view and workspace of surgical tools are compromised due to the indirect access to the anatomy and lack of surgeon's hand-eye coordination. The sensors 134 provide a tactile sensation to the surgeon by providing information regarding shape, stiffness, and texture of organ or tissue (different characteristics) to the surgeon's hands through a sense of touch. This detects a tumor through palpation, which exhibits a "tougher" feel than that of healthy soft tissue, pulse felt from blood vessels, and abnormal lesions. The sensors 134 can output shape, size, pressure, softness, composition, temperature, vibration, shear, and normal forces. The sensors 134 can be electrical or optical, consisting of capacitive, inductive, piezoelectric, piezoresistive, magnetic, and auditory. The sensors 134 can be used in robotic or laparoscopic surgery, palpation, biopsy, heart ablation, and valvuloplasty.

In some embodiments, the system 100 includes an imaging system 136 (instruments are used for the creation of images and visualization of the interior of a human body for diagnostic and treatment purposes). The imaging system 136 is used in different medical settings and can help in the screening of health conditions, diagnosing causes of symptoms, or monitoring of health conditions. The imaging system 136 can include various imaging techniques such as X-ray, fluoroscopy, magnetic resonance imaging (MRI), ultrasound, endoscopy, elastography, tactile imaging, thermography, medical photography, and nuclear medicine, e.g., positron emission tomography (PET). Some factors which can drive the market are cost and clinical advantages of medical imaging modalities, a rising share of ageing populations, increasing prevalence of cardiovascular or lifestyle diseases, and increasing demand from emerging economies.

In some embodiments, the imaging system 136 includes X-ray medical imaging instruments that use X-ray radiation (i.e., X-ray range in the electromagnetic radiation spectrum) for the creation of images of the interior of the human body for diagnostic and treatment purposes. An X-ray instrument is also referred to as an X-ray generator. It is a non-invasive instrument based on different absorption of X-rays by tissues based on their radiological density (radiological density is different for bones and soft tissues). For the creation of an image by the X-ray instrument, X-rays produced by an X-ray tube are passed through a patient positioned to the detector. As the X-rays pass through the body, images appear in shades of black and white, depending on the type and densities of tissue the X-rays pass through. Some of the applications where X-rays are used can be bone fractures, infections, calcification, tumors, arthritis, blood vessel blockages, digestive problems, or heart problems. The X-ray instrument can consist of components such as an X-ray tube, operating console, collimator, grid, detector, radiographic film, etc.

In some embodiments, the imaging system 136 includes MRI medical imaging instruments that use powerful magnets for the creation of images of the interior of the human body for diagnostic and treatment purposes. Some of the applications where MRI can be used are brain/spinal cord anomalies, tumors in the body, breast cancer screening, joint injuries, uterine/pelvic pain detection, or heart problems. For the creation of the image by an MRI instrument, magnetic resonance is produced by powerful magnets, which produce a strong magnetic field that forces protons in the body to align with that field. When a radiofrequency current is then pulsed through the patient, the protons are stimulated, and spin out of equilibrium, straining against the pull of the magnetic field. Turning off the radiofrequency field allows detection of energy released by realignment of protons with the magnetic field by MRI sensors. The time taken by the protons for realignment with the magnetic field and energy release is dependent on environmental factors and the chemical nature of the molecules. MRI is more widely suitable for imaging of non-bony parts or soft tissues of the body. MRI can be less harmful as it does not use damaging ionizing radiation as in the X-ray instrument. MRI instruments can consist of magnets, gradients, radiofrequency systems, or computer control systems. Some areas where imaging by MRI should be prohibited can be people with implants.

In some embodiments, the imaging system 136 uses computed tomography imaging (CT) that uses an X-ray radiation (i.e., X-ray range in the electromagnetic radiation spectrum) for the creation of cross-sectional images of the interior of the human body. CT refers to a computerized X-ray imaging procedure in which a narrow beam of X-rays is aimed at a patient and quickly rotated around the body, producing signals that are processed by the machine's computer to generate cross-sectional images—or "slices"—of the body. A CT instrument is different from an X-ray instrument as it creates 3-dimensional cross-sectional images of the body while the X-ray instrument creates 2-dimensional images of the body; the 3-dimensional cross-sectional images are created by taking images from different angles, which is done by taking a series of tomographic images from different angles. The diverse images are collected by a computer and digitally stacked to form a 3-dimensional image of the patient. For creation of images by the CT instrument, a CT scanner uses a motorized X-ray source that rotates around the circular opening of a donut-shaped structure called a gantry while the X-ray tube rotates around the patient shooting narrow beams of X-rays through the body. Some of the applications where CT can be used can be blood clots; bone fractures, including subtle fractures not visible on X-ray; or organ injuries.

In some embodiments, the imaging system 136 includes ultrasound imaging, also referred to as sonography or ultrasonography, that uses ultrasound or sound waves (also referred to as acoustic waves) for the creation of cross-sectional images of the interior of the human body. Ultrasound waves in the imaging system 136 can be produced by a piezoelectric transducer, which produces sound waves and sends them into the body. The sound waves that are reflected are converted into electrical signals, which are sent to an ultrasound scanner. Ultrasound instruments can be used for diagnostic and functional imaging or for therapeutic or interventional procedures. Some of the applications where ultrasound can be used are diagnosis/treatment/guidance during medical procedures (e.g., biopsies, internal organs such as liver/kidneys/pancreas, fetal monitoring, etc.), in soft tissues, muscles, blood vessels, tendons, or joints. Ultrasound can be used for internal imaging (where the transducer is placed in organs, e.g., vagina) and external imaging (where the transducer is placed on the chest for heart monitoring or the abdomen for fetal monitoring). An ultrasound machine can consist of a monitor, keyboard, processor, data storage, probe, and transducer.

In some embodiments, the system 100 includes a stereotactic navigation system 138 that uses patient imaging (e.g., CT, MRI) to guide surgical robots in the placement of specialized surgical instruments and implants. The patient images are taken to guide a surgical robot before or during the medical procedure. The stereotactic navigation system 138 includes a camera having infrared sensors to determine the location of the tip of the probe being used in the surgical procedure. This information is sent in real-time so that the surgical robot has a clear image of the precise location where it is working in the body. The stereotactic navigation system 138 can be framed (requires attachment of a frame to the patient's head using screws or pins) or frameless (does not require the placement of a frame on the patient's anatomy). The stereotactic navigation system 138 can be used for diagnostic biopsies, tumor resection, bone preparation/implant placement, placement of electrodes, otolaryngologic procedures, or neurosurgical procedures.

In some embodiments, the system 100 includes an anesthesiology machine 140 that is used to generate and mix medical gases, such as oxygen or air, and anesthetic agents to induce and maintain anesthesia in patients. The anesthesiology machine 140 delivers oxygen and anesthetic gas to the patient and filters out expiratory carbon dioxide. The anesthesiology machine 140 can perform functions such as providing oxygen (02), accurately mixing anesthetic gases and vapors, enabling patient ventilation, and minimizing anesthesia-related risks to patients and staff. The anesthesiology machine 140 can include the following essential components: a source of O2, O2 flowmeter, vaporizer (anesthetics include isoflurane, halothane, enflurane, desflurane, sevoflurane, and methoxyflurane), patient breathing circuit (tubing, connectors, and valves), and scavenging system (removes any excess anesthetics gases). The anesthesiology machine 140 can be divided into three parts: the high pressure system, the intermediate pressure system, and the low pressure system. The process of anesthesia starts with oxygen flow from a pipeline or cylinder through the flowmeter; the O2 flows through the vaporizer and picks up the anesthetic vapors; the O2-anesthetic mix then flows through the breathing circuit and into the patient's lungs, usually by spontaneous ventilation or normal respiration.

In some embodiments, the system 100 includes a surgical bed 142 equipped with mechanisms that can elevate or lower the entire bed platform; flex, or extend individual components of the platform; or raise or lower the head or the feet of the patient independently. The surgical bed 142 can be an operation bed, cardiac bed, amputation bed, or fracture bed. Some essential components of the surgical bed 142 can be a bed sheet, woolen blanket, bath towel, and bed block. The surgical bed 142 can also be referred to as a post-operative bed, which refers to a special type of bed made for the patient who is coming from the operation theater or from another procedure that requires anesthesia. The surgical bed 142 is designed in a manner that makes it easier to transfer an unconscious or weak patient from a stretcher/wheelchair to the bed. The surgical bed 142 should protect bed linen from vomiting, bleeding, drainage, and discharge; provide warmth and comfort to the patient to prevent shock; provide necessary positions, which are suitable for operation; protect patient from being chilled; and be prepared to meet any emergency.

In some embodiments, the system 100 includes a Jackson frame 144 (or Jackson table), which refers to a frame or table that is designed for use in spinal surgeries and can be used in a variety of spinal procedures in supine, prone, or lateral positions in a safe manner. Two peculiar features of the Jackson table 144 are the absence of central table support and an ability to rotate the table through 180 degrees. The Jackson table 144 is supported at both ends, which keeps the whole of the table free. This allows the visualization of a patient's trunk and major parts of extremities as well. The Jackson frame 144 allows the patient to be slid from the cart onto the table in the supine position with appropriate padding placed. The patient is then strapped securely on the Jackson table 144.

In some embodiments, the system 100 includes a disposable air warmer 146 (sometimes referred to as a Bair™ or Bair Hugger™). The disposable air warmer 146 is a convective temperature management system used in a hospital or surgery center to maintain a patient's core body temperature. The disposable air warmer 146 includes a reusable warming unit and a single-use disposable warming blanket for use during surgery. It can also be used before and after surgery. The disposable air warmer 146 uses convective warming consisting of two components: a warming unit and a disposable blanket. The disposable air warmer 146 filters air and then forces warm air through disposable blankets, which cover the patient. The blanket can be designed to use pressure points on the patient's body to prevent heat from reaching areas at risk for pressure sores or burns. The blanket can also include drainage holes where fluid passes through the surface of the blanket to linen underneath, which will reduce the risk of skin softening and reduce the risk of unintended cooling because of heat loss from evaporation.

In some embodiments, the system 100 includes a sequential compression device (SCD) 148 used to help prevent blood clots in the deep veins of legs. The sequential compression device 148 uses cuffs around the legs that fill with air and squeeze the legs. This increases blood flow through the veins of the legs and helps prevent blood clots. A deep vein thrombosis (DVT) is a blood clot that forms in a vein deep inside the body. Some of the risks of using the SCD 148 can be discomfort, warmth, sweating beneath the cuff, skin breakdown, nerve damage, or pressure injury.

In some embodiments, the system 100 includes a bed position controller 150, which refers to an instrument for controlling the position of the patient bed. Positioning a patient in bed is important for maintaining alignment and for preventing bedsores (pressure ulcers), foot drop, and contractures. Proper positioning is also vital for providing comfort for patients who are bedridden or have decreased mobility related to a medical condition or treatment. When positioning a patient in bed, supportive devices such as pillows, rolls, and blankets, along with repositioning, can aid in providing comfort and safety. The patient can be in the following positions in a bed: supine position, prone position, lateral position, Sims' position, Fowler's position, semi-Fowler's position, orthopedic or tripod position, or Trendelenburg position.

In some embodiments, the system 100 includes environmental controls 152. The environmental controls 152 can be operating room environmental controls for control or maintenance of the environment in the operating room 102 where procedures are performed to minimize the risk of airborne infection and to provide a conducive environment for everyone in the operating room 102 (e.g., surgeon, anesthesiologist, nurses, and patient). Some factors that can contribute to poor quality in the environment of the operating room 102 are temperature, ventilation, and humidity, and those conditions can lead to profound effects on the health and work productivity of people in the operating room 102. As an example: surgeons prefer a cool, dry climate since they work under bright, hot lights; anesthesia personnel prefer a warmer, less breezy climate; patient condition demands a relatively warm, humid, and quiet environment. The operating room environmental controls can control the environment by taking care of the following factors: environmental humidity, infection control, or odor control. Humidity control can be performed by controlling the temperature of anesthesia gases; infection can be controlled by the use of filters to purify the air.

In some embodiments, the environmental controls 152 include a heating, ventilation, and air conditioning (HVAC) system for regulating the environment of indoor settings by moving air between indoor and outdoor areas, along with heating and cooling. HVAC can use a different combination of systems, machines, and technologies to improve comfort. HVAC can be necessary to maintain the environment of the operating room 102. The operating room 102 can be a traditional operating room (which can have a large diffuser array directly above the operating table) or a hybrid operating room (which can have monitors and imaging equipment 136 that consume valuable ceiling space and complicate the design process). HVAC can include three main units, for example, a heating unit (e.g., furnace or boiler), a ventilation unit (natural or forced), and an air conditioning unit (which can remove existing heat). HVAC can be made of components such as air returns, filters, exhaust outlets, ducts, electrical elements, outdoor units, compressors, coils, and blowers. The HVAC system can use central heating and AC systems that use a single blower to circulate air via internal ducts.

In some embodiments, the environmental controls 152 include an air purification system for removing contaminants from the air in the operating room 102 to improve indoor air quality. Air purification can be important in the operating room 102 as surgical site infection can be a reason for high mortality and morbidity. The air purification system can deliver clean, filtered, contaminant-free air over the surgical bed 142 using a diffuser, airflow, etc., to remove all infectious particles down and away from the patient. The air purification system can be an air curtain, multi-diffuser array, or single large diffuser (based on laminar diffuser flow) or High-Efficiency Particulate Air filter (HEPA filter). A HEPA filter protects a patient from infection and contamination using a filter, which is mounted at the terminal of the duct. A HEPA filter can be mounted on the ceiling and deliver clean, filtered air in a flow to the operating room 102 that provides a sweeping effect that pushes contaminants out via the return grilles that are usually mounted on the lower wall.

In some embodiments, the system 100 includes one or more medical or surgical tools 154. The surgical tools 154 can include orthopedic tools (also referred to as orthopedic instruments) used for treatment and prevention of deformities and injuries of the musculoskeletal system or skeleton, articulations, and locomotive system (i.e., set formed by skeleton, muscles attached to it, and the part of the nervous system that controls the muscles). A major percentage of orthopedic tools are made of plastic. The orthopedic tools can be divided into the following specialties: hand and wrist, foot and ankle, shoulder, and elbow, arthroscopic, hip, and knee. The orthopedic tools can be fixation tools, relieving tools, corrective tools, or compression-distraction tools. A fixation tool refers to a tool designed to restrict movements partially or completely in a joint, e.g., hinged splints (for preserving a certain range of movement in a joint) or rigid splints. A relieving tool refers to a tool designed to relieve pressure on an ailing part by transferring support to healthy parts of an extremity, e.g., Thomas splint and the Voskoboinikova apparatus. A corrective tool refers to a surgical tool designed to gradually correct a deformity, e.g., corsets, splints, orthopedic footwear, insoles, and other devices to correct abnormal positions of the foot. A compression-distraction tool refers to a surgical tool designed to correct acquired or congenital deformities of the extremities, e.g., curvature, shortening, and pseudarthrosis such as Gudushauri. A fixation tool can be an internal fixation tool (e.g., screws, plates) or external fixation tools used to correct a radius or tibia fracture. The orthopedic tools can be bone-holding forceps, drill bits, nail pins, hammers, staples, etc.

In some embodiments, the surgical tools 154 include a drill for making holes in bones for insertion of implants like nails, plates, screws, and wires. The drill tool functions by drilling cylindrical tunnels into bone. Drills can be used in orthopedics for performing medical procedures. If the drill does not stop immediately when used, the use of the drill on bones can have some risks, such as harm caused to bone, muscle, nerves, and venous tissues, which are wrapped by surrounding tissue. Drills vary widely in speed, power, and size. Drills can be powered as electrical, pneumatic, or battery. Drills generally can work on speeds below 1000 rpm in orthopedic settings. Temperature control of drills is an important aspect in the functioning of the drill and is dependent on parameters such as rotation speed, torque, orthotropic site, sharpness of the cutting edges, irrigation, and cooling systems. The drill can include a physical drill, power cord, electronically motorized bone drill, or rotating bone shearing incision work unit.

In some embodiments, the surgical tools 154 include a scalpel for slicing, cutting, or osteotomy of bone during orthopedic procedure. The scalpel can be designed to provide clean cuts through osseous structures with minimal loss of viable bone while sparing adjacent elastic soft tissues largely unaffected while performing a slicing procedure. This is suited for spine applications where bone must be cut adjacent to the dura and neural structures. The scalpel does not rotate but performs cutting by an ultrasonically oscillating or forward/backward moving metal tip. Scalpels can prevent injuries caused by a drill in a spinal surgery such as complications such as nerve thermal injury, grasping soft tissue, tearing dura mater, and mechanical injury.

In some embodiments, stitches (also referred to as sutures) or a sterile, surgical thread is used to repair cuts or lacerations and is used to close incisions or hold body tissues together after a surgery or an injury. Stitches can involve the use of a needle along with an attached thread. Stitches can be either absorbable (the stitches automatically break down harmlessly in the body over time without intervention) or non-absorbable (the stitches do not automatically break down over time and must be manually removed if not left indefinitely). Stitches can be based on material monofilament, multifilament, and barb. Stitches can be classified based on size. Stitches can be based on synthetic or natural material. Stitches can be coated or un-coated.

In some embodiments, the surgical tools 154 include a stapler used for fragment fixation when inter-fragmental screw fixation is not easy. When there is vast damage and a bone is broken into fragments, staples can be used between these fragments for internal fixation and bone reconstruction. For example, they can be used around joints in ankle and foot surgeries, in cases of soft tissue damage, or to attach tendons or ligaments to the bone for reconstruction surgery. Staplers can be made of surgical grade stainless steel or titanium, and they are thicker, stronger, and larger.

In some embodiments, other medical or surgical equipment, such as a set of articles, surgical tools, or objects, is used to implement or achieve an operation or activity. A medical equipment refers to an article, instrument, apparatus, or machine used for diagnosis, prevention, or treatment of a medical condition or disease, or to the detection, measurement, restoration, correction, or modification of structure/function of the body for some health purpose. The medical equipment can perform functions invasively or non-invasively. In some embodiments, the medical equipment includes components such as a sensor/transducer, a signal conditioner, a display, or a data storage unit, etc. In some embodiments, the medical equipment includes a sensor to receive a signal from instruments measuring a patient's body, a transducer for converting one form of energy to electrical energy, a signal conditioner such as an amplifier, filter, etc., to convert the output from the transducer into an electrical value, a display to provide a visual representation of the measured parameter or quantity, or a storage system to store data, which can be used for future reference. A medical equipment can perform diagnosis or provide therapy; for example, the equipment delivers air into the lungs of a patient who is physically unable to breathe, or breathes insufficiently, and moves it out of the lungs.

In some embodiments, the system includes a machine 156 to aid in breathing. The machine 156 can be a ventilator (also referred to as a respirator) that provides a patient with oxygen when they are unable to breathe on their own. A ventilator is required when a person is not able to breathe on their own. A ventilator can perform a function of gently pushing air into the lungs and allow it to come back out. The ventilator functions by delivery of positive pressure to force air into the lungs, while usual breathing uses negative pressure by the opening of the mouth, and air flows in. The ventilator can be required during surgery or after surgery. The ventilator can be required in case of respiratory failure due to acute respiratory distress syndrome, head injury, asthma, lung diseases, drug overdose, neonatal respiratory distress syndrome, pneumonia, sepsis, spinal cord injury, cardiac arrest, etc., or during surgery. The ventilator can be used with a face mask (non-invasive ventilation, where the ventilation is required for a shorter duration of time) or with a breathing tube also referred to as an endotracheal tube (invasive ventilation, where the ventilation is required for a longer duration of time). Ventilator use can have some risks such as infections, fluid build-up, muscle weakness, lung damage, etc. The ventilator can be operated in various modes, such as assist-control ventilation (ACV), synchronized intermittent-mandatory ventilation (SIMV), pressure-controlled ventilation (PCV), pressure support ventilation (PSV), pressure-controlled inverse ratio ventilation (PCIRV), airway pressure release ventilation (APRV), etc.

The ventilator can include a gas delivery system, power source, control system, safety feature, gas filter, and monitor.

In some embodiments, the machine 156 is a continuous positive airway pressure (CPAP) used for the treatment of sleep apnea disorder in a patient. Sleep apnea refers to a disorder in which breathing repeatedly stops and starts while a patient is sleeping, often because throat/airways briefly collapse or something temporarily blocks them. Sleep apnea can lead to serious health problems, such as high blood pressure and heart trouble. A CPAP instrument helps the patient with sleep apnea to breathe more easily during sleep by sending a steady flow of oxygen into the nose and mouth during sleep, which keeps the airways open and helps the patient to breathe normally. The CPAP machine can work by a compressor/motor, which generates a continuous stream of pressurized air that travels through an air filter into a flexible tube. The tube delivers purified air into a mask sealed around the nose/mouth of the patient. The airstream from the instrument pushes against any blockages, opening the airways so lungs receive plenty of oxygen, and breathing does not stop as nothing obstructs oxygen. This helps the patient to not wake up to resume breathing. CPAP can have a nasal pillow mask, nasal mask, or full mask. A CPAP instrument can include a motor, a cushioned mask, a tube that connects the motor to the mask, a headgear frame, and adjustable straps. The essential components can be a motor, a cushioned mask, and a tube that connects the motor to the mask.

In some embodiments, the system 100 includes surgical supplies, consumables 158, or necessary supplies for the system 100 to provide care within the hospital or surgical environment. The consumables 158 can include gloves, gowns, masks, syringes, needles, sutures, staples, tubing, catheters, or adhesives for wound dressing, in addition to other surgical tools needed by surgical robots, doctors, and nurses to provide care. Depending on the device, mechanical testing can be carried out in tensile, compression, or flexure; in dynamic or fatigue; via impact; or with the application of torsion. The consumables 158 can be disposable (e.g., time-saving, have no risk of healthcare-associated infections, and cost-efficient) or sterilizable (to avoid cross-contamination or risk of surgical site infections).

In some embodiments, the system 100 includes a robotic surgical system 160 (sometimes referred to as a medical robotic system or a robotic system) that provides intelligent services and information to the operating room 102 and the console 108 by interacting with the environment, including human beings, via the use of various sensors, actuators, and human interfaces. The robotic surgical system 160 can be employed for automating processes in a wide range of applications, ranging from industrial (manufacturing), domestic, medical, service, military, entertainment, space, etc. The medical robotic system market is segmented by product type into surgical robotic systems, rehabilitative robotic systems, non-invasive radiosurgery robots, and hospital and pharmacy robotic systems. Robotic surgeries can be performed using tele-manipulators (e.g., input devices 166 at the console 108), which use the surgeon's actions on one side to control one or more "effectors" on the other side. The medical robotic system 160 provides precision and can be used for remotely controlled, minimally invasive procedures. The robotic surgical system 160 includes computer-controlled electromechanical devices that work in response to controls (e.g., input devices 166 at the console 108) manipulated by the surgeons.

In some embodiments, the system 100 includes equipment tracking systems 162, such as RFID, which is used to tag an instrument with an electronic tag and tracks it using the tag. Typically, this could involve a centralized platform that provides details such as location, owner, contract, and maintenance history for all equipment in real-time. A variety of techniques can be used to track physical assets, including RFID, global positioning system (GPS), Bluetooth low energy (BLE), barcodes, near-field communication (NFC), Wi-Fi, etc. The equipment tracking system 162 includes hardware components, such as RFID tags, GPS trackers, barcodes, and QR codes. The hardware component is placed on the asset, and it communicates with the software (directly or via a scanner), providing the software with data about the asset's location and properties. In some embodiments, the equipment tracking system 162 uses electromagnetic fields to transmit data from an RFID tag to a reader. Reading of RFID tags can be done by portable or mounted RFID readers. The read range for RFID varies with the frequency used. Managing and locating important assets is a key challenge for tracking medical equipment. Time spent searching for critical equipment can lead to expensive delays or downtime, missed deadlines and customer commitments, and wasted labor. The problem has previously been solved by using barcode labels or manual serial numbers and spreadsheets; however, these require manual labor. The RFID tag can be passive (smaller and less expensive, read ranges are shorter, have no power of their own, and are powered by the radio frequency energy transmitted from RFID readers/antennas) or active (larger and more expensive, read ranges are longer, have a built-in power source and transmitter of their own).

In some embodiments, the system 100 includes medical equipment, computers, software, etc., located in the doctor's office 110 that is communicably coupled to the operating room 102 over the network 104. For example, the medical equipment in the doctor's office 110 can include a microscope 116 used for viewing samples and objects that cannot be seen with an unaided eye. The microscope 116 can have components such as eyepieces, objective lenses, adjustment knobs, a stage, an illuminator, a condenser, or a diaphragm. The microscope 116 works by manipulating how light enters the eye using a convex lens, where both sides of the lens are curved outwards. When light reflects off of an object being viewed under the microscope 116 and passes through the lens, it bends toward the eye. This makes the object look bigger than it is. The microscope 116 can be compound (light-illuminated and the image seen with the microscope 116 is two-dimensional), dissection or stereoscope (light-illuminated and the image seen with the microscope 116 is three-dimensional), confocal (laser-illuminated and the image seen with the microscope 116 is on a digital computer screen), scanning electron (SEM) (electron-illuminated and the image seen with the microscope 116 is in black and white), or transmission electron microscope (TEM) (electron-illuminated and the image seen with the microscope 116 is the high magnification and high resolution).

The system 100 includes an electronic health records (EHR) database 106 that contains patient records. The EHR is a digital version of patients' paper charts. The EHR database 106 can contain more information than a traditional patient chart, including, but not limited to, a patient's medical history, diagnoses, medications, treatment plans, allergies, diagnostic imaging, lab results, etc. In some embodiments, the steps for each procedure disclosed herein are stored in the EHR database 106. Electronic health records can also include data collected from the monitors 112 from historical procedures. The EHR database 106 is implemented using components of the example computer system 300 illustrated and described in more detail with reference to FIG. 3.

In some embodiments, the EHR database 106 includes a digital record of patients' health information, collected, and stored systematically over time. The EHR database 106 can include demographics, medical history, history of present illness (HPI), progress notes, problems, medications, vital signs, immunizations, laboratory data, or radiology reports. Software (in memory 164) operating on the console 108 or implemented on the example computer system 300 (e.g., the instructions 304, 308 illustrated and described in more detail with reference to FIG. 3) are used to capture, store, and share patient data in a structured way. The EHR database 106 can be created and managed by authorized providers and can make health information accessible to authorized providers across practices and health organizations, such as laboratories, specialists, medical imaging facilities, pharmacies, emergency facilities, etc. The timely availability of EHR data enables healthcare providers to make more accurate decisions and provide better care to the patients by effective diagnosis and reduced medical errors. Besides providing opportunities to enhance patient care, the EHR database 106 can also be used to facilitate clinical research by combining patients' demographics into a large pool. For example, the EHR database 106 can support a wide range of epidemiological research on the natural history of disease, drug utilization, and safety, as well as health services research.

The console 108 is a computer device, such as a server, computer, tablet, smartphone, smart speaker, etc., implemented using components of the example computer system 300 illustrated and described in more detail with reference to FIG. 3. In some embodiments, the steps for each procedure disclosed herein are stored in memory 164 on the console 108 for execution.

In some embodiments, the operating room 102 or the console 108 includes high-definition monitors 124, which refer to displays in which a clearer picture is possible than with low-definition, low-resolution screens. The high-definition monitors 124 have a higher density of pixels per inch than past standard TV screens. Resolution for the high-definition monitors 124 can be 1280×720 pixels or more (e.g., Full HD, 1920×1080; Quad HD, 2560×1440; 4K, 3840×2160; 8K, 7680×4320 pixels). The high-definition monitor 124 can operate in progressive or interlaced scanning mode. High-definition monitors used in medical applications can offer improved visibility; allow for precise and safe surgery with rich color reproduction; provide suitable colors for each clinical discipline; provide better visibility, operability with a large screen and electronic zoom, higher image quality in low light conditions, better visualization of blood vessels and lesions, and high contrast at high spatial frequencies; be twice as sensitive as conventional sensors; and make it easier to determine tissue boundaries (fat, nerves, vessels, etc.).

In some embodiments, the console 108 includes an input interface or one or more input devices 166. The input devices 166 can include a keyboard, a mouse, a joystick, any hand-held controller, or a hand-controlled manipulator, e.g., a tele-manipulator used to perform robotic surgery.

In some embodiments, the console 108, the equipment in the doctor's office 110, and the EHR database 106 are communicatively coupled to the equipment in the operating room 102 by a direct connection, such as ethernet, or wirelessly by the cloud over the network 104. The network 104 is the same as or similar to the network 314 illustrated and described in more detail with reference to FIG. 3. For example, the console 108 can communicate with the robotic surgical system 160 using the network adapter 312 illustrated and described in more detail with reference to FIG. 3.

In embodiments, the system 100 uses quantum computing. Quantum computing refers to the use of a computational device or method that uses properties of quantum states defined by quantum mechanics such as superposition, entanglement, etc., to perform computations. Quantum devices use qubits, which are the quantum equivalent of bits in a classical computing system. Qubits have at least two quantum states or probable outcomes. These outcomes, combined with a coefficient representing the probability of each outcome, describes the possible states, or bits of data, which can be represented by the qubits according to the principle of quantum superposition. These states can be manipulated to shift the probability of each outcome, or additionally, add additional possible outcomes to perform computations, the final state of which can be measured to achieve the result.

Quantum computing provides significant benefits in the areas of encryption and the simulation of natural systems. Encryption is aided by the uncertain nature of quantum computing in that data is represented by an indeterminate state of probable outcomes, therefore making decryption virtually impossible. The simulation of natural systems, such as chemical and biological interactions, benefit from the fact that the nature of quantum computing is the same as the systems being simulated. In medical fields, quantum computing shows the greatest promise for drug discovery and simulating the interaction of drugs with biologic systems, however the same technology can also be used to predict the interaction of a biologic system with an implanted device, preventing rejection of an implant by a patient's body. Quantum computing can be used to investigate long term functioning of an implant. Further, quantum computing can be used to study the reaction of a patient to a surgical procedure, during a simulation, before a procedure, or actively during a procedure.

Figure 2:
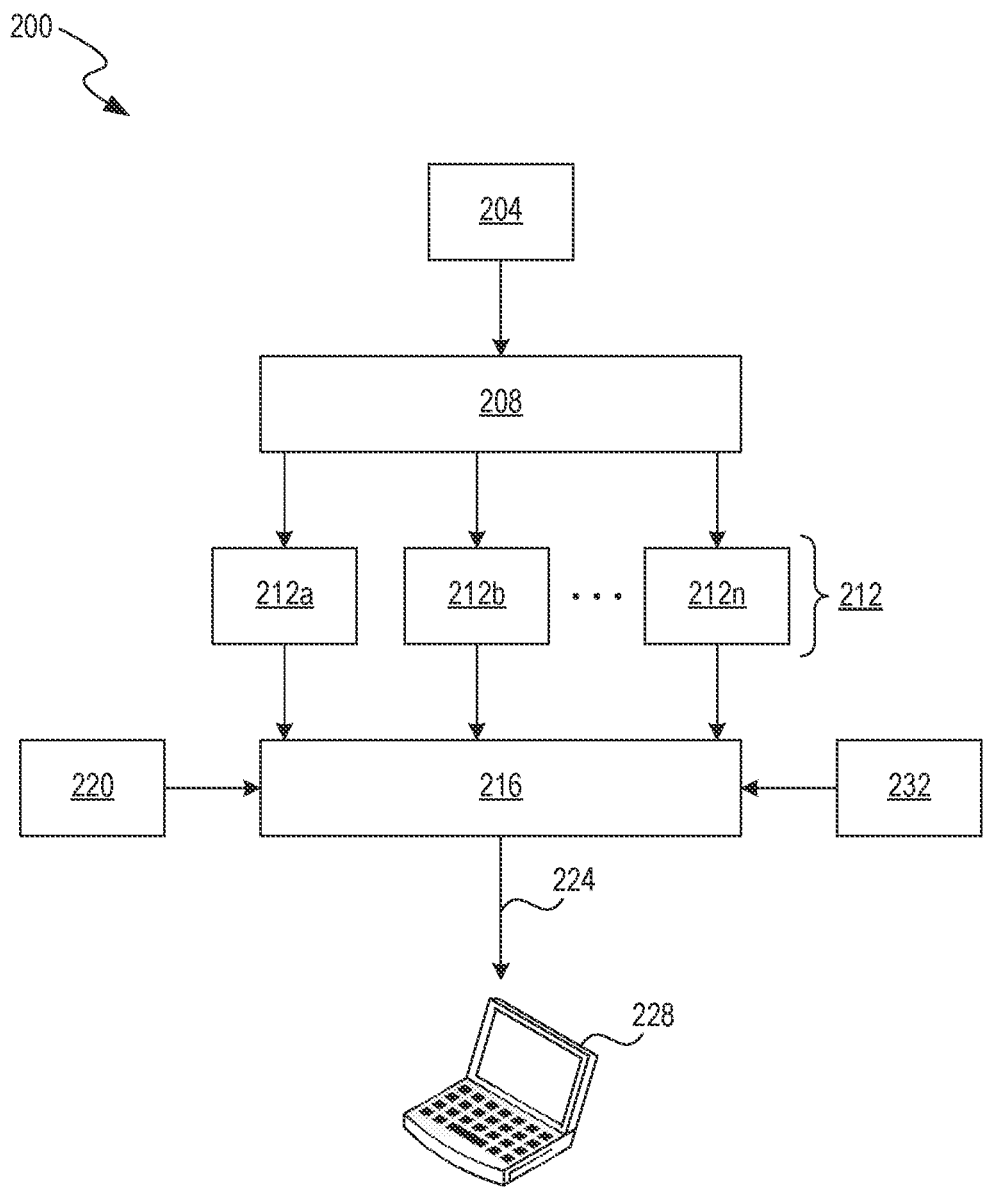
FIG. 2 is a block diagram illustrating an example machine learning (ML) system, in accordance with one or more embodiments.

FIG. 2 is a block diagram illustrating an example machine learning (ML) system 200, in accordance with one or more embodiments. The ML system 200 is implemented using components of the example computer system 300 illustrated and described in more detail with reference to FIG. 3. For example, the ML system 200 can be implemented on the console 108 using instructions programmed in the memory 164 illustrated and described in more detail with reference to FIG. 1. Likewise, embodiments of the ML system 200 can include different and/or additional components or be connected in different ways. The ML system 200 is sometimes referred to as a ML module.

The ML system 200 includes a feature extraction module 208 implemented using components of the example computer system 300 illustrated and described in more detail with reference to FIG. 3. In some embodiments, the feature extraction module 208 extracts a feature vector 212 from input data 204. For example, the input data 204 can include one or more physiological parameters measured by the monitors 112 illustrated and described in more detail with reference to FIG. 1. The feature vector 212 includes features 212$a$, 212$b$, . . . , 212$n$. The feature extraction module 208 reduces the redundancy in the input data 204, e.g., repetitive data values, to transform the input data 204 into the reduced set of features 212, e.g., features 212$a$, 212$b$, . . . , 212$n$. The feature vector 212 contains the relevant information from the input data 204, such that events or data value thresholds of interest can be identified by the ML model 216 by using this reduced representation. In some example embodiments, the following dimensionality reduction techniques are used by the feature extraction module 208: independent component analysis, Isomap, kernel principal component analysis (PCA), latent semantic analysis, partial least squares, PCA, multifactor dimensionality reduction, nonlinear dimensionality reduction, multilinear PCA, multilinear subspace learning, semidefinite embedding, autoencoder, and deep feature synthesis.

In alternate embodiments, the ML model 216 performs deep learning (also known as deep structured learning or hierarchical learning) directly on the input data 204 to learn data representations, as opposed to using task-specific algorithms. In deep learning, no explicit feature extraction is performed; the features 212 are implicitly extracted by the ML system 200. For example, the ML model 216 can use a cascade of multiple layers of nonlinear processing units for implicit feature extraction and transformation. Each successive layer uses the output from the previous layer as input. The ML model 216 can thus learn in supervised (e.g., classification) and/or unsupervised (e.g., pattern analysis) modes. The ML model 216 can learn multiple levels of representations that correspond to different levels of abstraction, wherein the different levels form a hierarchy of concepts. In this manner, the ML model 216 can be configured to differentiate features of interest from background features.

In alternative example embodiments, the ML model 216, e.g., in the form of a CNN generates the output 224, without the need for feature extraction, directly from the input data 204. The output 224 is provided to the computer device 228 or the console 108 illustrated and described in more detail with reference to FIG. 1. The computer device 228 is a server, computer, tablet, smartphone, smart speaker, etc., implemented using components of the example computer system 300 illustrated and described in more detail with reference to FIG. 3. In some embodiments, the steps performed by the ML system 200 are stored in memory on the computer device 228 for execution. In other embodiments, the output 224 is displayed on the high-definition monitors 124 illustrated and described in more detail with reference to FIG. 1.

A CNN is a type of feed-forward artificial neural network in which the connectivity pattern between its neurons is inspired by the organization of a visual cortex. Individual cortical neurons respond to stimuli in a restricted area of space known as the receptive field. The receptive fields of different neurons partially overlap such that they tile the visual field. The response of an individual neuron to stimuli within its receptive field can be approximated mathematically by a convolution operation. CNNs are based on biological processes and are variations of multilayer perceptrons designed to use minimal amounts of preprocessing.

The ML model 216 can be a CNN that includes both convolutional layers and max pooling layers. The architecture of the ML model 216 can be "fully convolutional," which means that variable sized sensor data vectors can be fed into it. For all convolutional layers, the ML model 216 can specify a kernel size, a stride of the convolution, and an amount of zero padding applied to the input of that layer. For the pooling layers, the model 216 can specify the kernel size and stride of the pooling.

In some embodiments, the ML system 200 trains the ML model 216, based on the training data 220, to correlate the feature vector 212 to expected outputs in the training data 220. As part of the training of the ML model 216, the ML system 200 forms a training set of features and training labels by identifying a positive training set of features that have been determined to have a desired property in question, and, in some embodiments, forms a negative training set of features that lack the property in question.

The ML system 200 applies ML techniques to train the ML model 216, that when applied to the feature vector 212, outputs indications of whether the feature vector 212 has an associated desired property or properties, such as a probability that the feature vector 212 has a particular Boolean property, or an estimated value of a scalar property. The ML system 200 can further apply dimensionality reduction (e.g., via linear discriminant analysis (LDA), PCA, or the like) to reduce the amount of data in the feature vector 212 to a smaller, more representative set of data.

The ML system 200 can use supervised ML to train the ML model 216, with feature vectors of the positive training set and the negative training set serving as the inputs. In some embodiments, different ML techniques, such as linear support vector machine (linear SVM), boosting for other algorithms (e.g., AdaBoost), logistic regression, naïve Bayes, memory-based learning, random forests, bagged trees, decision trees, boosted trees, boosted stumps, neural networks, CNNs, etc., are used. In some example embodiments, a validation set 232 is formed of additional features, other than those in the training data 220, which have already been determined to have or to lack the property in question. The ML system 200 applies the trained ML model 216 to the features of the validation set 232 to quantify the accuracy of the ML model 216. Common metrics applied in accuracy measurement include: Precision and Recall, where Precision refers to a number of results the ML model 216 correctly predicted out of the total it predicted, and Recall is a number of results the ML model 216 correctly predicted out of the total number of features that had the desired property in question. In some embodiments, the ML system 200 iteratively re-trains the ML model 216 until the occurrence of a stopping condition, such as the accuracy measurement indication that the ML model 216 is sufficiently accurate, or a number of training rounds having taken place. The validation set 232 can include data corresponding to confirmed anatomical features, tissue states, tissue conditions, diagnoses, or combinations thereof. This allows the detected values to be validated using the validation set 232. The validation set 232 can be generated based on analysis to be performed.

Figure 3:
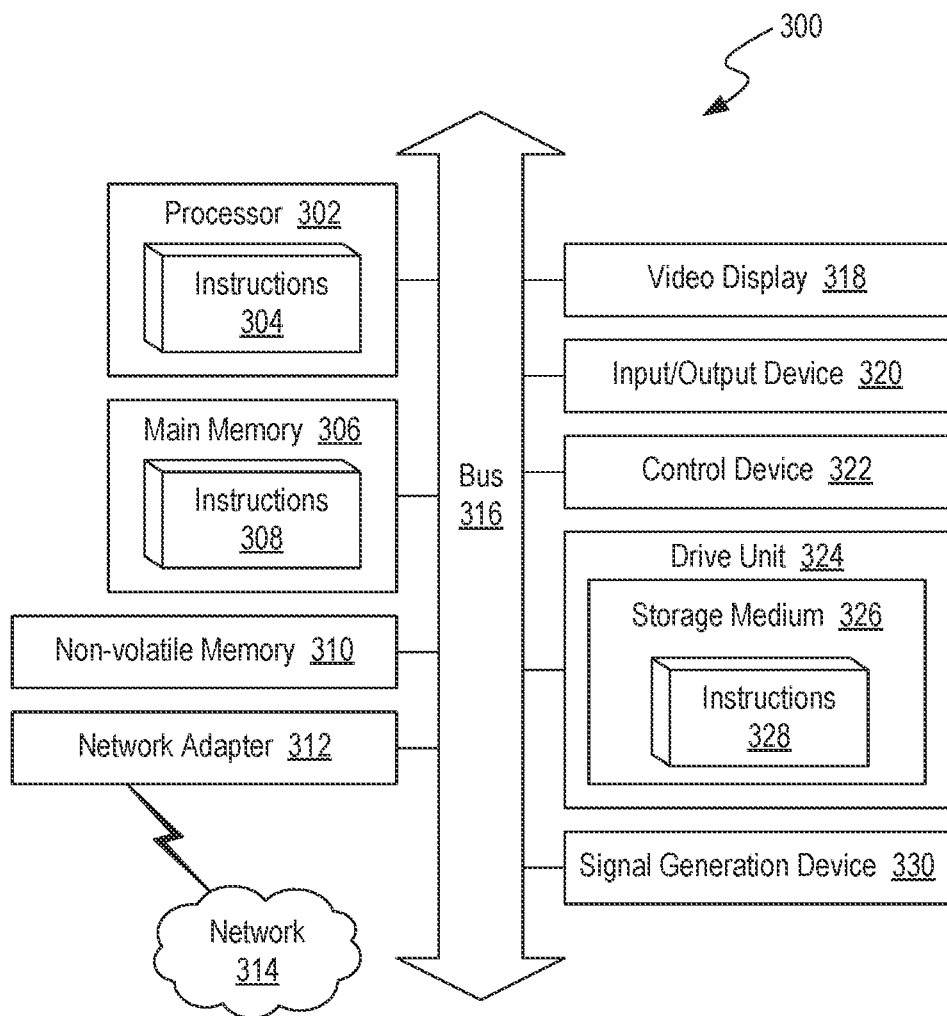
FIG. 3 is a block diagram illustrating an example computer system, in accordance with one or more embodiments.

FIG. 3 is a block diagram illustrating an example computer system, in accordance with one or more embodiments. Components of the example computer system 300 can be used to implement the monitors 112, the console 108, or the EHR database 106 illustrated and described in more detail with reference to FIG. 1. In some embodiments, components of the example computer system 300 are used to implement the ML system 200 illustrated and described in more detail with reference to FIG. 2. At least some operations described herein can be implemented on the computer system 300.

The computer system 300 can include one or more central processing units ("processors") 302, main memory 306, non-volatile memory 310, network adapters 312 (e.g., network interface), video displays 318, input/output devices 320, control devices 322 (e.g., keyboard and pointing devices), drive units 324 including a storage medium 326, and a signal generation device 320 that are communicatively connected to a bus 316. The bus 316 is illustrated as an abstraction that represents one or more physical buses and/or point-to-point connections that are connected by appropriate bridges, adapters, or controllers. The bus 316, therefore, can include a system bus, a Peripheral Component Interconnect (PCI) bus or PCI-Express bus, a HyperTransport or industry standard architecture (ISA) bus, a small computer system interface (SCSI) bus, a universal serial bus (USB), IIC (I2C) bus, or an Institute of Electrical and Electronics Engineers (IEEE) standard 1394 bus (also referred to as "Firewire").

The computer system 300 can share a similar computer processor architecture as that of a desktop computer, tablet computer, personal digital assistant (PDA), mobile phone, game console, music player, wearable electronic device (e.g., a watch or fitness tracker), network-connected ("smart") device (e.g., a television or home assistant device), virtual/augmented reality systems (e.g., a head-mounted display), or another electronic device capable of executing a set of instructions (sequential or otherwise) that specify action(s) to be taken by the computer system 300.

While the main memory 306, non-volatile memory 310, and storage medium 326 (also called a "machine-readable medium") are shown to be a single medium, the term "machine-readable medium" and "storage medium" should be taken to include a single medium or multiple media (e.g., a centralized/distributed database and/or associated caches and servers) that store one or more sets of instructions 328. The term "machine-readable medium" and "storage medium" shall also be taken to include any medium that is capable of storing, encoding, or carrying a set of instructions for execution by the computer system 300.

In general, the routines executed to implement the embodiments of the disclosure can be implemented as part of an operating system or a specific application, component, program, object, module, or sequence of instructions (collectively referred to as "computer programs"). The computer programs typically include one or more instructions (e.g., instructions 304, 308, 328) set at various times in various memory and storage devices in a computer device. When read and executed by the one or more processors 302, the instruction(s) cause the computer system 300 to perform operations to execute elements involving the various aspects of the disclosure.

Moreover, while embodiments have been described in the context of fully functioning computer devices, those skilled in the art will appreciate that the various embodiments are capable of being distributed as a program product in a variety of forms. The disclosure applies regardless of the particular type of machine or computer-readable media used to actually effect the distribution.

Further examples of machine-readable storage media, machine-readable media, or computer-readable media include recordable-type media such as volatile and non-volatile memory devices 310, floppy and other removable disks, hard disk drives, optical discs (e.g., Compact Disc Read-Only Memory (CD-ROMS), Digital Versatile Discs (DVDs)), and transmission-type media such as digital and analog communication links.

The network adapter 312 enables the computer system 300 to mediate data in a network 314 with an entity that is external to the computer system 300 through any communication protocol supported by the computer system 300 and the external entity. The network adapter 312 can include a network adapter card, a wireless network interface card, a router, an access point, a wireless router, a switch, a multi-layer switch, a protocol converter, a gateway, a bridge, a bridge router, a hub, a digital media receiver, and/or a repeater.

The network adapter 312 can include a firewall that governs and/or manages permission to access proxy data in a computer network and tracks varying levels of trust between different machines and/or applications. The firewall can be any number of modules having any combination of hardware and/or software components able to enforce a predetermined set of access rights between a particular set of machines and applications, machines and machines, and/or applications and applications (e.g., to regulate the flow of traffic and resource sharing between these entities). The firewall can additionally manage and/or have access to an access control list that details permissions including the access and operation rights of an object by an individual, a machine, and/or an application, and the circumstances under which the permission rights stand.

Figure 4A:
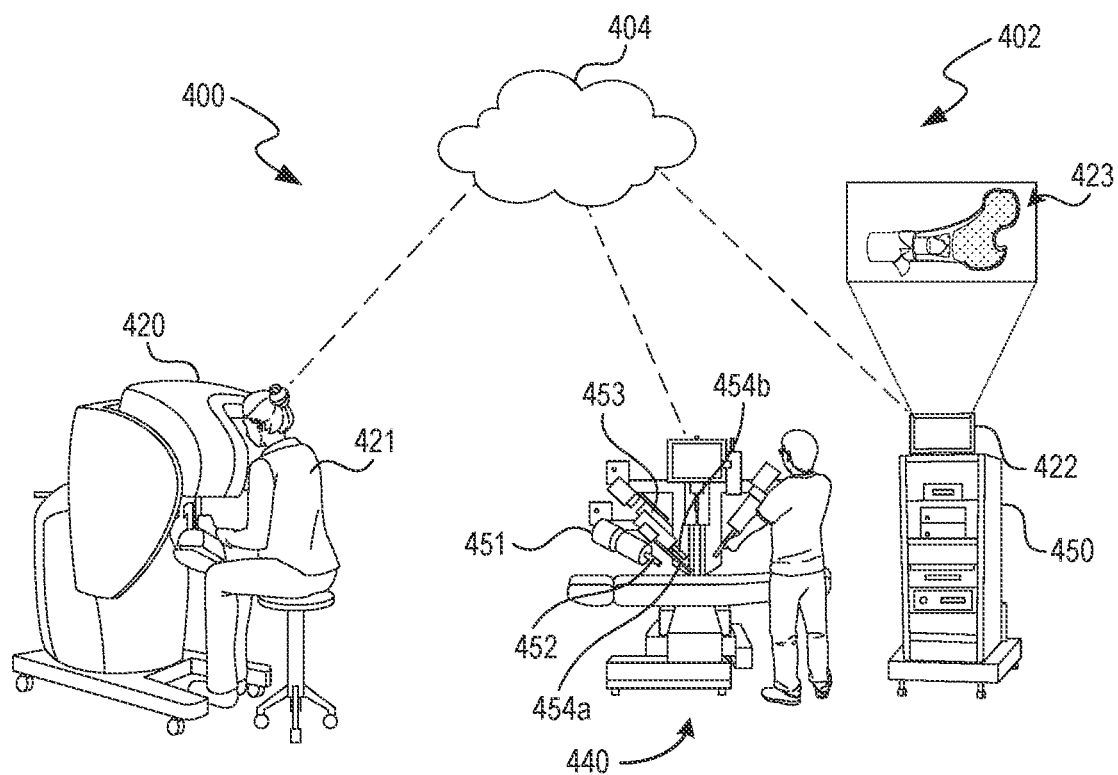
FIG. 4A is a block diagram illustrating an example robotic surgical system, in accordance with one or more embodiments.

FIG. 4A is a block diagram illustrating an example robotic surgical system 400, in accordance with one or more embodiments. The robotic surgical system 400 is the same as or similar to the robotic surgical system 160 illustrated and described in more detail with reference to FIG. 1. The robotic surgical system 400 can include components and features discussed in connection with FIGS. 1-3 and 4B-5. For example, the robotic surgical system 400 can include a console 420 with features of the console 108 of FIG. 1. Likewise, the components and features of FIG. 4A can be included or used with other embodiments disclosed herein. For example, the description of the input devices of FIG. 4A applies equally to other input devices (e.g., input devices 166 of FIG. 1).

The robotic surgical system 400 includes a user device or console 420 ("console 420"), a surgical robot 440, and a computer or data system 450. The console 420 can be operated by a surgeon and can communicate with components in an operating room 402, remote devices/servers, a network 404, or databases (e.g., database 106 of FIG. 1) via the network 404. The robotic surgical system 400 can include surgical control software and can include a guidance system (e.g., ML guidance system, AI guidance system, etc.), surgical planning software, event detection software, surgical tool software, etc. or other features disclosed herein to perform surgical step(s) or procedures or implement steps of processes discussed herein.

The user 421 can use the console 420 to view and control the surgical robot 440. The console 420 can be communicatively coupled to one or more components disclosed herein and can include input devices operated by one, two, or more users. The input devices can be hand-operated controls, but can alternatively, or in addition, include controls that can be operated by other parts of the user's body, such as, but not limited to, foot pedals. The console 420 can include a clutch pedal to allow the user 421 to disengage one or more sensor-actuator components from control by the surgical robot 440. The console 420 can also include display or output so that the one of more users can observe the patient being operated on, or the product being assembled, for example. In some embodiments, the display can show images, such as, but not limited to, medical images, video, etc. For surgical applications, the images could include, but are not limited to, real-time optical images, real-time ultrasound, real-time OCT images and/or other modalities, or could include pre-operative images, such as MRI, CT, PET, etc. The various imaging modalities can be selectable, programmed, superimposed, and/or can include other information superimposed in graphical and/or numerical or symbolic form.

The robotic surgical system 400 can include multiple consoles 420 to allow multiple users to simultaneously or sequentially perform portions of a surgical procedure. The term "simultaneous" herein refers to actions performed at the same time or in the same surgical step. The number and configuration of consoles 420 can be selected based on the surgical procedure to be performed, number and configurations of surgical robots, surgical team capabilities, or the like.

Figure 4B:
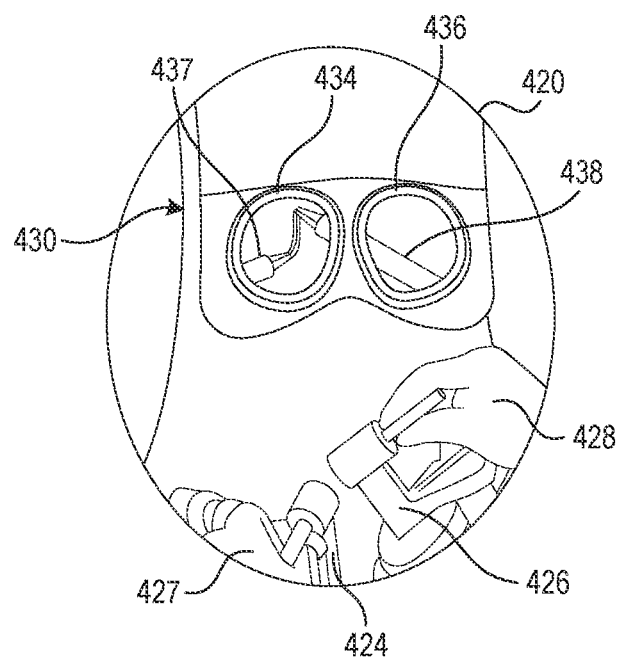
FIG. 4B illustrates an example console of the robotic surgical system of FIG. 4A, in accordance with one or more embodiments.

FIG. 4B illustrates an example console 420 of the robotic surgical system 400 of FIG. 4A, in accordance with one or more embodiments. The console 420 includes hand-operated input devices 424, 426, illustrated held by the user's left and right hands 427, 428, respectively. A viewer 430 includes left and right eye displays 434, 436. The user can view, for example, the surgical site, instruments 437, 438, or the like. The user's movements of the input devices 424, 426 can be translated in real-time to, for example, mimic the movement of the user on the viewer 430 and display (e.g., display 124 of FIG. 1) and within the patient's body while the user can be provided with output, such as alerts, notifications, and information. The information can include, without limitation, surgical or implantation plans, patient vitals, modification to surgical plans, values, scores, predictions, simulations, and other output, data, and information disclosed herein. The console 420 can be located at the surgical room or at a remote location.

The viewer 430 can display at least a portion of a surgical plan, including multiwavelength images, imaging modality information, fused data sets, tissue types, mapped images (e.g., tissue types maps, bone tissue maps, tissue density maps, diseased tissue maps, tissue condition maps, etc.), past and future surgical steps, patient monitor readings (e.g., vitals), surgical room information (e.g., available team members, available surgical equipment, surgical robot status, or the like), images (e.g., pre-operative images, images from simulations, real-time images, instructional images, etc.), and other surgical assist information. In some embodiments, the viewer 430 can be a VR/AR headset, display, or the like. The robotic surgical system 400, illustrated and described in more detail with reference to FIG. 4A, can further include multiple viewers 430 so that multiple members of a surgical team can view the surgical procedure. The number and configuration of the viewers 430 can be selected based on the configuration and number of surgical robots.

Referring again to FIG. 4A, the surgical robot 440 can include one or more controllers, computers, sensors, arms, articulators, joints, links, grippers, motors, actuators, imaging systems, effector interfaces, end effectors, or the like. For example, a surgical robot with a high number of degrees of freedom can be used to perform complicated procedures whereas a surgical robot with a low number of degrees of freedom can be used to perform simple procedures. The configuration (e.g., number of arms, articulators, degrees of freedom, etc.) and functionality of the surgical robot 440 can be selected based on the procedures to be performed.

The surgical robot 440 can operate in different modes selected by a user, set by the surgical plan, and/or selected by the robotic surgical system 400. In some procedures, the surgical robot 440 can remain in the same mode throughout a surgical procedure. In other procedures, the surgical robot 440 can be switched between modes any number of times. The configuration, functionality, number of modes, and type of modes can be selected based on the desired functionality and user control of the robotic surgical system 400. The robotic surgical system 400 can switch between modes based on one or more features, such as triggers, notifications, warnings, events, etc. Different example modes are discussed below. A trigger can be implemented in software to execute a jump to a particular instruction or step of a program. A trigger can be implemented in hardware, e.g., by applying a pulse to a trigger circuit.

In a user control mode, a user 421 controls, via the console 420, movement of the surgical robot 440. The user's movements of the input devices can be translated in real-time into movement of end effectors 452 (one identified).

In a semi-autonomous mode, the user 421 controls selected steps and the surgical robot 440 autonomously performs other steps. For example, the user 421 can control one robotic arm to perform one surgical step while the surgical robot 440 autonomously controls one or more of the other arms to concurrently perform another surgical step. In another example, the user 421 can perform steps suitable for physician control. After completion, the surgical robot 440 can perform steps involving coordination between three or more robotic arms, thereby enabling complicated procedures. For example, the surgical robot 440 can perform steps involving four or five surgical arms, each with one or more end effectors 452. The surgical robot 440 can include a multi-modality imager 453 having imaging devices 454a, 454b (collectively "imaging devices 454"). The imaging devices 454 can be, for example, PET scanners, ultrasound imagers, MRI imagers, CT scanners, cameras (e.g., camera imager hardware, digital cameras, etc.), infrared imagers, etc. In embodiments, the surgical robot 440 retrieves/receives images from standalone X-ray machines, MRI machines, CT scanners, etc. Example imaging devices are discussed in connection with FIGS. 1 and 6. The number, imaging capabilities, and configurations of the imaging devices 454 can be selected based on the imaging to be performed.

The robotic surgical system 400 can automatically generate multi-modality images based on surgical plans and then perform one or more surgical steps of a planned surgical procedure. In embodiments, the robotic surgical system 400 analyzes a surgical plan for a patient to generate an imaging plan for obtaining patient information for diagnostic purposes, modifying the surgical plan, performing surgical steps (e.g., one surgical step, multiple surgical steps, all surgical steps), etc. The imaging plan can include, without limitation, one or more regions of interest, targeted information, predicted features of interest, information for diagnostic purposes, or the like. The robotic surgical system 400 can generate the imaging plan based on imaging capabilities of the multi-modality imager 453. The robotic surgical system 400 can notify the surgical team to add or replace imaging devices 454 to achieve the desired imaging capability.

The robotic surgical system 400 can retrieve available images of a patient from, for example, electronic medical records, image databases, and/or other imaging sources. The robotic surgical system 400 can identify and retrieve images that can be processed for producing one or more multi-modality images. The robotic surgical system 400 can determine whether additional unavailable images could be useful for generating multi-modality images that (1) meet at least one threshold criteria (e.g., a confidence score), (2) identify features of interest, (3) have diagnostic capability criteria, etc. In some procedures, the robotic surgical system 400 retrieves available images and determines imaging programs or parameters (e.g., positions, imaging settings, etc.) of one or more of the imaging devices 454 corresponding to the available images. In embodiments, a machine learning system (see FIG. 2) can be used to generate imaging plans based on training sets. The training sets can include, for example, single modality training sets, composite multi-modality training sets, confirmed diagnostic training sets, and other training sets. This allows the robotic surgical system 400 to perform re-training procedures for continuously or periodically training the machine learning system. Newly-captured images can be keyed to or matched with the retrieved images, thereby increasing accuracy of the multi-modality images. During intro-operative imaging, the images can be analyzed in real-time to further control the robotic surgical system 400.

In an autonomous mode, the surgical robot 440 can autonomously perform steps under the control of the data system 450. The robotic surgical system 400 can be pre-programmed with instructions for performing the steps autonomously. For example, command instructions can be generated based on a surgical plan. The surgical robot 440 autonomously performs steps or the entire procedure. The user 421 and surgical team can observe the surgical procedure to modify or stop the procedure. Advantageously, complicated procedures can be autonomously performed without user intervention to enable the surgical team to focus and attend to other tasks. Although the robotic surgical system 400 can autonomously perform steps, the surgical team can provide information in real-time that is used to continue the surgical procedure. The information can include surgical robot input, surgical team observations, and other data input.

The robotic surgical system 400 can also adapt to the user control to facilitate completion of the surgical procedure. In some embodiments, the robotic surgical system 400 can monitor, via one or more sensors, at least a portion of the surgical procedure performed by the surgical robot 440. The robotic surgical system 400 can identify an event, such as a potential adverse surgical event, associated with a robotically performed surgical task. For example, a potential adverse surgical event can be determined based on acquired monitoring data and information for the end effector, such as surgical tool data from a medical device report, database, manufacturer, etc. The robotic surgical system 400 can perform one or more actions based on the identified event. The actions can include, without limitation, modification of the surgical plan to address the potential adverse surgical event, thereby reducing the risk of the event occurring. The adverse surgical event can include one or more operating parameters approaching respective critical thresholds, as discussed in connection with FIG. 12. The adverse surgical events can be identified using a machine learning model trained using, for example, prior patient data, training sets (e.g., tool data), etc.

In some embodiments, the robotic surgical system 400 determines whether a detected event (e.g., operational parameters outside a target range or exceeding a threshold, etc.) is potentially an adverse surgical event based on one or more criteria set by the robotic surgical system 400, user, or both. The adverse surgical event can be an adverse physiological event of the patient, surgical robotic malfunction, surgical errors, or other event that can adversely affect the patient or the outcome of the surgery. Surgical events can be defined and inputted by the user, surgical team, healthcare provider, manufacturer of the robotic surgery system, or the like.

The robotic surgical system 400 can take other actions in response to identification of an event. If the robotic surgical system 400 identifies an end effector malfunction or error, the robotic surgical system 400 can stop usage of the end effector and replace the malfunctioning component (e.g., surgical tool or equipment) to complete the procedure. The robotic surgical system 400 can monitor hospital inventory, available resources in the surgical room 402, time to acquire equipment (e.g., time to acquire replacement end effectors, surgical tools, or other equipment), and other information to determine how to proceed with surgery. The robotic surgical system 400 can generate multiple proposed surgical plans for continuing with the surgical procedure. The user and surgical team can review the proposed surgical plans to select an appropriate surgical plan. The robotic surgical system 400 can modify a surgical plan with one or more corrective surgical steps based on identified surgical complications, sensor readings, or the like. The surgical steps include, without limitation, cauterizing, cutting tissue, clamping tissue, stapling tissue, excising tissue, implanting items, alternative steps to replace planned surgical steps, manipulating tissue, or other steps disclosed herein. The surgical steps can be selected to keep the patient's vital(s) within a target range, for example, based on one or more surgical criteria (e.g., overall surgical time, length of surgical step, etc.).

The robotic surgical system 400 can retrieve surgical system information from a database to identify events. The database can describe, for example, maintenance of the robotic surgery system, specifications of the robotic surgery system, specifications of end effectors, surgical procedure information for surgical tools, consumable information associated with surgical tools, operational programs and parameters for surgical tools, monitoring protocols for surgical tools, or the like. The robotic surgical system 400 can use other information in databases disclosed herein to generate rules for triggering actions, identifying warnings, defining events, or the like. Databases can be updated with data (e.g., intraoperative data collected during the surgical procedure, simulation data, etc.) to intraoperatively adjust surgical plans, collect data for ML/AI training sets, or the like. Data from on-site and off-site simulations (e.g., pre-, or post-operative virtual simulations, simulations using models, etc.) can be generated and collected.

The surgical robot 440 can include robotic arms 451 (one identified) with robotic links, motors, and integrated or removable end effectors 452 (one identified). The end effectors 452 can include, without limitation, imagers (e.g., cameras, optical guides, etc.), robotic grippers, instrument holders, cutting instruments (e.g., cutters, scalpels, or the like), drills, cannulas, reamers, rongeurs, scissors, clamps, or other equipment or surgical tools disclosed herein. In some embodiments, the end effectors can be reusable or disposable surgical tools. The number and configuration of end effectors can be selected based on the configuration of the robotic system, procedure to be performed, surgical plan, etc. Imaging and viewing technologies can integrate with the surgical robot 440 to provide more intelligent and intuitive results.

The data system 450 can improve surgical planning, monitoring (e.g., via the display 422), data collection, surgical robotics/navigation systems, intelligence for selecting instruments, implants, etc. The data system 450 can execute, for example, surgical control instructions or programs for a guidance system (e.g., ML guidance system, AI guidance system, etc.), surgical planning programs, event detection programs, surgical tool programs, etc. For example, the data system 450 can increase procedure efficiency and reduce surgery duration by providing information insertion paths, surgical steps, or the like. The data system 450 can be incorporated into or include other components and systems disclosed herein. As shown by FIG. 4A, the display 422 can display, for example, a diagnosis of tissue, images, maps, surgical plans, etc. For example, the display 422 can display a diagnostic image or map showing, for example, a bone in image 423 (discussed in more detail below with reference to multi-modality imaging), regions of interest (e.g., zones of diseased tissue, regions of tissue with specific characteristic(s), margins, etc.), features of interest, anatomical elements (e.g., cartilage, soft tissue, etc.), or the like. An example image is discussed in connection with FIG. 15. In some embodiments, a diagnostic image can include tissue density, tissue state, identified disease tissue, or the like. The system 402 can use the displayed data to perform one or more surgical steps. A user can view the display 422 to confirm the position of the tissue during the procedure.

The robotic surgical system 400 can be used to perform open procedures, minimally invasive procedures, such as laparoscopic surgeries, non-robotic laparoscopic/abdominal surgery, retroperitoneoscopy, arthroscopy, pelviscopy, nephroscopy, cystoscopy, cisternoscopy, sinoscopy, hysteroscopy, urethroscopy, and the like. The methods, components, apparatuses, and systems can be used with many different systems for conducting robotic or minimally invasive surgery. One example of a surgical system and surgical robots which can incorporate methods and technology is the DAVINCI™ system available from Intuitive Surgical, Inc.™ of Mountain View, Calif. However, other surgical systems, robots, and apparatuses can be used.

The robotic surgical system 400 can perform one or more simulations using selected entry port placements and/or robot positions, to allow a surgeon or other user to practice procedures. The practice session can be used to generate, modify, or select a surgical plan. In some embodiments, the system can generate a set of surgical plans for physician consideration. The physician can perform practice sessions for each surgical plan to determine and select a surgical plan to be implemented. In some embodiments, the systems disclosed herein can perform virtual surgeries to recommend a surgical plan. The physician can review the virtual simulations to accept or reject the recommended surgical plan. The physician can modify surgical plans pre-operatively or intraoperatively.

Embodiments can provide a means for mapping the surgical path for neurosurgery procedures that minimize damage through artificial intelligence mapping. The software for artificial intelligence is trained to track the least destructive pathway. A surgical robot can make an initial incision based on a laser marking on the skin that illuminates the optimal site. Next, a robot can make a small hole and insert surgical equipment (e.g., guide wires, cannulas, etc.) that highlights the best pathway. This pathway minimizes the amount of tissue damage that occurs during surgery. Mapping can also be used to identify one or more insertion points associated with a surgical path. Mapping can be performed before treatment, during treatment, and/or after treatment. For example, pretreatment and posttreatment mapping can be compared by the surgeon and/or ML/AI system. The comparison can be used to determine next steps in a procedure and/or further train the ML/AI system.

Figure 5:
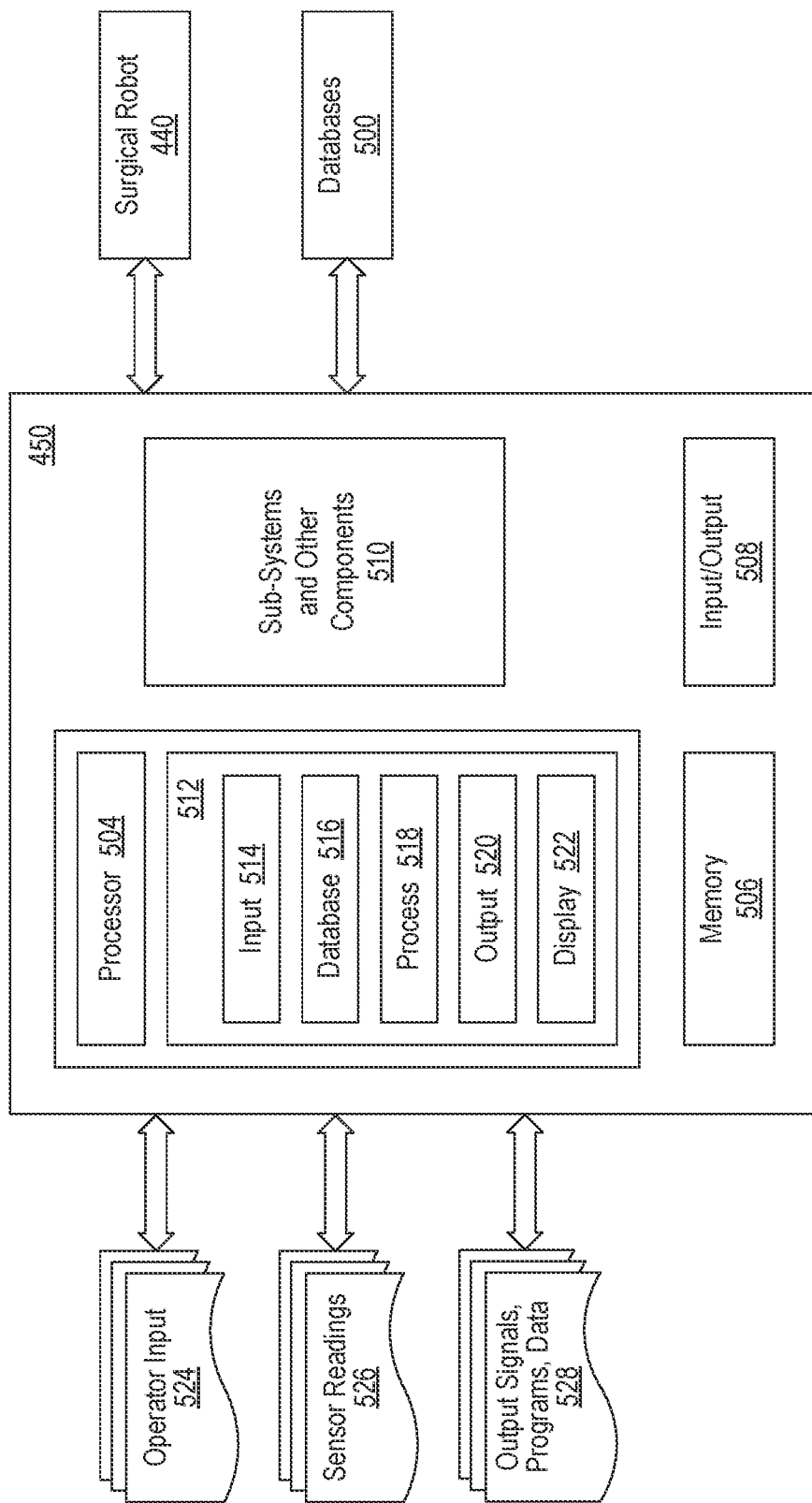
FIG. 5 is a schematic block diagram illustrating subcomponents of the robotic surgical system of FIG. 4A, in accordance with one or more embodiments.

FIG. 5 is a schematic block diagram illustrating subcomponents of the robotic surgical system 400 of FIG. 4A in accordance with embodiment of the present technology. The data system 450 has one or more processors 504, a memory 506, input/output devices 508, and/or subsystems and other components 510. The processor 504 can perform any of a wide variety of computing processing, image processing, robotic system control, plan generation or modification, and/or other functions. Components of the data system 450 can be housed in a single unit (e.g., within a hospital or surgical room) or distributed over multiple, interconnected units (e.g., though a communications network). The components of the data system 450 can accordingly include local and/or devices.

As illustrated in FIG. 5, the processor 504 can include a plurality of functional modules 512, such as software modules, for execution by the processor 504. The various implementations of source code (i.e., in a conventional programming language) can be stored on a computer-readable storage medium or can be embodied on a transmission medium in a carrier wave. The modules 512 of the processor 504 can include an input module 514, a database module 516, a process module 518, an output module 520, and, optionally, a display module 524 for controlling the display.

In operation, the input module 514 accepts an operator input 524 via the one or more input devices, and communicates the accepted information or selections to other components for further processing. The database module 516 organizes plans (e.g., robotic control plans, surgical plans, etc.), records (e.g., maintenance records, patient records, historical treatment data, etc.), surgical equipment data (e.g., instrument specifications), control programs, and operating records and other operator activities, and facilitates storing and retrieving of these records to and from a data storage device (e.g., internal memory 506, external databases, etc.). Any type of database organization can be utilized, including a flat file system, hierarchical database, relational database, distributed database, etc.

In the illustrated example, the process module 518 can generate control variables based on sensor readings 526 from sensors (e.g., end effector sensors of the surgical robot 440, patient monitoring equipment, etc.), operator input 524 (e.g., input from the surgeon console 420 and/or other data sources), and the output module 520 can communicate operator input to external computing devices and control variables to controllers. The display module 522 can be configured to convert and transmit processing parameters, sensor readings 526, output signals 528, input data, treatment profiles and prescribed operational parameters through one or more connected display devices, such as a display screen, touch screen, printer, speaker system, etc.

In various embodiments, the processor 504 can be a standard central processing unit or a secure processor. Secure processors can be special-purpose processors (e.g., reduced instruction set processor) that can withstand sophisticated attacks that attempt to extract data or programming logic. The secure processors cannot have debugging pins that enable an external debugger to monitor the secure processor's execution or registers. In other embodiments, the system can employ a secure field-programmable gate array, a smartcard, or other secure devices.

The memory 506 can be standard memory, secure memory, or a combination of both memory types. By employing a secure processor and/or secure memory, the system can ensure that data and instructions are both highly secure and sensitive operations such as decryption are shielded from observation. In various embodiments, the memory 506 can be flash memory, secure serial EEPROM, secure field-programmable gate array, or secure application-specific integrated circuit. The memory 506 can store instructions for causing the surgical robot 440 to perform acts disclosed herein.

The input/output device 508 can include, without limitation, a touch screen, a keyboard, a mouse, a stylus, a push button, a switch, a potentiometer, a scanner, an audio component such as a microphone, or any other device suitable for accepting user input and can also include one or more video monitors, a medium reader, an audio device such as a speaker, any combination thereof, and any other device or devices suitable for providing user feedback. For example, if an applicator moves an undesirable amount during a treatment session, the input/output device 508 can alert the subject and/or operator via an audible alarm. The input/output device 508 can be a touch screen that functions as both an input device and an output device.

The data system 450 can output instructions to command the surgical robot 440 and communicate with one or more databases 2600. The surgical robot 440 or other components disclosed herein can communicate to send collected data (e.g., sensor readings, instrument data, surgical robot data, etc.) to the database 500. This information can be used to, for example, create new training data sets, generate plans, perform future simulations, post-operatively analyze surgical procedures, or the like. The data system 450 can be incorporated, used with, or otherwise interact with other databases, systems, and components disclosed herein. In some embodiments, the data system 450 can be incorporated into the surgical robot 440 or other systems disclosed herein. In some embodiments, the data system 450 can be located at a remote location and can communicate with a surgical robot via one or more networks. For example, the data system 450 can communicate with a hospital via a network, such as a wide area network, a cellular network, etc. One or more local networks at the hospital can establish communication channels between surgical equipment within the surgical room.

A surgical program or plan ("surgical plan") can include, without limitation, patient data (e.g., pre-operative images, medical history, physician notes, etc.), imaging programs, surgical steps, mode switching programs, criteria, goals, or the like. The imaging programs can include, without limitation, AR/VR programs, identification programs (e.g., fiducial identification programs, tissue identification programs, target tissue identification programs, etc.), image analysis programs, or the like. Surgical programs can define surgical procedures or a portion thereof. For example, surgical programs can include end effector information, positional information, surgical procedure protocols, safety settings, surgical robot information (e.g., specifications, usage history, maintenance records, performance ratings, etc.), order of surgical steps, acts for a surgical step, feedback (e.g., haptic feedback, audible feedback, etc.), or the like. The mode switching programs can be used to determine when to switch the mode of operation of the surgical robot 440. For example, mode switching programs can include threshold or configuration settings for determining when to switch the mode of operation of the surgical robot 440. Example criteria can include, without limitation, thresholds for identifying events, data for evaluating surgical steps, monitoring criteria, patient health criteria, physician preference, or the like. The goals can include intraoperative goals, post-operative goals (e.g., target outcomes, metrics, etc.), goal rankings, etc. Monitoring equipment or the surgical team can determine goal progress, whether a goal has been achieved, etc. If an intraoperative goal is not met, the surgical plan can be modified in real-time so that, for example, the post-operative goal is achieved. The post-operative goal can be redefined intraoperatively in response to events, such as surgical complications, unplanned changes to patient's vitals, etc.

The surgical plan can also include healthcare information, surgical team information, assignments for surgical team members, or the like. The healthcare information can include surgical room resources, hospital resources (e.g., blood banks, standby services, available specialists, etc.), local or remote consultant availability, insurance information, cost information (e.g., surgical room costs, surgical team costs, etc.).

The systems disclosed herein can generate pre-operative plans and simulation plans. Pre-operative plans can include scheduling of equipment, surgical room, staff, surgical teams, and resources for surgery. The systems can retrieve information from one or more databases to generate the pre-operative plan based on physician input, insurance information, regulatory information, reimbursements, patient medical history, patient data, or the like. Pre-operative plans can be used to generate surgical plans, cost estimates, scheduling of consultants and remote resources, or the like. For example, a surgical plan can be generated based on available resources scheduled by the pre-operative plans. If a resource becomes unavailable, the surgical plan can be adjusted for the change in resources. The healthcare provider can be alerted if additional resources are recommended. The systems disclosed herein can generate simulation plans for practicing surgical procedures. On approval, a surgeon can virtually simulate a procedure using a console or another simulation device. Plans (e.g., surgical plans, implantation plans, etc.) can be generated and modified based on the surgeon's performance and simulated outcome.

The systems disclosed herein can generate post-operative plans for evaluating surgical outcomes, developing physical therapy and/or rehab programs and plans, etc. The post-operative plans can be modified by the surgical team, primary care provider, and others based on the recovery of the patient. In some embodiments, systems generate pre-operative plans, surgical plans, and post-operative plans prior to beginning a surgical procedure. The system then modifies one or more or the plans as additional information is provided. For example, one or more steps of the methods discussed herein can generate data that is incorporated into the plan. ML data sets to be incorporated into the plan generate a wide range of variables to be considered when generating plans. Plans can be generated to optimize patient outcome, reduce or limit the risk of surgical complications, mitigate adverse events, manage costs for surgical procedures, reduce recovery time, or the like. The healthcare provider can modify how plans are generated over time to further optimize based on one or more criteria.

FIG. 6 is a block diagram illustrating an example robotic surgical system, in accordance with one or more embodiments. The system can be incorporated into or used with technology discussed in connection with FIGS. 1-5. For example, one or more components of the system 600 can be incorporated into the operating room 102 discussed in connection with FIG. 1. By way of another example, a user interface 610 and/or imaging device 618 of the system 600 can be part of the console 420 discussed in connection with FIG. 4B. Output from the system 600 can be transmitted to the controller 604 and/or various other components disclosed herein. Accordingly, the system can be incorporated into robotic surgery systems, or utilized to perform manual surgical procedures or to perform other procedures disclosed herein. Portions of the system 600 are implemented using the components of the example computer system 300 illustrated and described in more detail with reference to FIG. 3. Likewise, embodiments of the system 600 can include different and/or additional components or can be connected in different ways.

This system includes a surgical robot 602, which is a robotic system designed to perform a surgical operation or assist a surgeon in performing a surgical operation on a patient. The surgical robot can perform digital image analysis for robotic installation of surgical implants. An example surgical robot 440 is illustrated and described in more detail with reference to FIG. 4A. The surgical robot 602 can include a controller 604, a memory 606, and at least one robotic arm 612 having an end effector 614. The surgical robot 602 can further include a user interface 610 for accepting control inputs from a user, such as a surgeon or other medical professional. The surgical robot 602 can further include a communications interface 608 for transmitting and receiving data to and from a cloud 624 for the purpose of training an artificial intelligence (AI) implemented within the surgical robot 602, or receiving commands from a remote user or another AI implemented external to the surgical robot 602. An example AI (machine learning system 200) is illustrated and described in more detail with reference to FIG. 2. The surgical robot 602 can additionally include multiple sensors 616 for providing feedback to the user or an AI.

The controller 604 shown by FIG. 6 is a computing device including a computer processor for performing computations. The controller 604 communicates with a memory 606 for storing data. The controller 604 is in communication with a communications interface 608 and can further control the at least one robotic arm 612 and end effector 614 of the surgical robot 602. In embodiments, the controller is a commercially available central processing unit (CPU) or graphical processing unit (GPU), or a proprietary, purpose-built design. Multiple controllers 604 can operate in tandem. The multiple controllers 604 can be of different types, such as a CPU and a GPU. A GPU is not restricted to only processing graphics or image data and can be used for other computations.

The memory 606 includes electronic circuitry within a computing device of the surgical robot 602 that temporarily stores data for usage by the controller 604. Examples of a main memory 306, non-volatile memory 310, and storage medium 326 are illustrated and described in more detail with reference to FIG. 3. The memory 606 can additionally include persistent data storage for storing data used by the controller 604. The memory 606 can be integrated into the controller 604 or can be a discrete component. The memory 606 can be integrated into a circuit, such as a soldered-on component of a single-board computer (SBC), or can be a removable component such as a discrete dynamic random-access memory (DRAM) stick, a secure digital (SD) card, a flash drive, a solid state drive (SSD), a magnetic hard disk drive (SSD), etc. In embodiments, the memory 606 is part of a controller 604. Multiple types of memory can be used by the surgical robot 602.

The communications interface 608 enables the surgical robot 602 to communicate with external devices and can include a wireless antenna and transceiver, or a port for receiving a cable to facilitate a wired connection. Examples of a wired connection include Ethernet, universal serial bus (USB), and proprietary connections. The communications interface 608 can be wireless, including a combination of Wi-Fi, Bluetooth, near field communication (NFC), or a cellular communications interface such as 3G, 4G, LTE, or 5G. The communications interface 608 can connect the user interface 610 to the surgical robot 602 or can facilitate access to a local network or a cloud 624 network to access a remote server and/or a database (see FIG. 7).

The user interface 610 is a means of interacting with the surgical robot 602 and can include a combination of a keyboard, computer mouse, trackball, joystick, wireless or wired gamepad, sliders, scroll wheels, touch screen, or microphone for receiving voice commands. The user interface 610 can additionally include different methods of interaction for a user (e.g., surgeon) with the surgical robot 602. The user interface 610 can accept direct inputs, such as from a joystick controlling the movement of a robotic arm. The user interface 610 can accept indirect inputs, such as commands entered on a keyboard or touch screen, e.g., adjusting the sensitivity of a joystick control or the speed of movement of the robotic arm 612 in response to joystick input. The user interface 610 can also include a screen for presenting information to a user such as patient status, imaging data, or navigation data, and speakers for providing auditory feedback. The user interface 610 can also use haptics to provide feedback to the user.

The robotic arm 612 is a mechanically actuated arm or lever with at least two degrees of freedom. The robotic arm 612 will typically include at least one end effector 614 or an imaging device 618, and can include both an end effector 614 and an imaging device 618. The robotic arm 612 can additionally be implemented to replace the end effector 614 to facilitate multiple functions and operation of a variety of surgical tools. Example surgical tools 154 are illustrated and described in more detail with reference to FIG. 1. The robotic arm 612 can be manually controlled or operated in an autonomous or semi-autonomous mode. The surgical robot 602 can have one robotic arm 612 or multiple robotic arms 612, each of which can be operated independently by one or more users or autonomous systems (e.g., an AI) or a combination of users and autonomous systems.

The end effector 614 is a tool or device located at or attached to an end of the robotic arm 612 for interacting with the patient's body or a physical object. The end effector 614 can be a surgical tool intended for acting upon or within the patient's body, or can be a gripping device for securing a separate surgical tool to the robotic arm 612. The end effector 614 can be permanently affixed to the end of the robotic arm 612 or can be detachable to allow for a system of interchangeable end effectors 614, which can alternatively be selected and swapped by a single robotic arm 612 or multiple robotic arms 612.

The sensor 616 is a measurement tool for monitoring a characteristic or metric associated with the surgical robot 602, the end effector 614, or the patient. The sensor 616 can be discrete or part of an array or assembly, such as an array of force transducers integrated into the end effector 614 to monitor the forces applied to the patient's body. One or more of the sensors 616 can include an electrophysiologic sensor, a temperature sensor, a thermal gradient sensor, a barometer, an altimeter, an accelerometer, a gyroscope, a humidity sensor, a magnetometer, an inclinometer, an oximeter, a colorimetric monitor, a sweat analyte sensor, a galvanic skin response sensor, an interfacial pressure sensor, a flow sensor, a stretch sensor, a microphone, or a combination thereof. The sensors 616 can be integrated into the operation of the surgical robot 602 or can monitor the status of the patient's body.

Data acquired by the sensors 616 can be used to train a machine learning (ML) model used by the surgical robot 602 or an AI to control the surgical robot 602. An example ML model 216 is illustrated and described in more detail with reference to FIG. 2. In some embodiments, ML model 216 is trained using reference patient data. In embodiments, the surgical robot 602 capture one or more images of an anatomy of a patient using one or more imaging devices 618. The imaging devices 618 refer to any device capable of collecting data that can be used to create an image, or a representation of a physical structure or phenomena. In embodiments, a computer system (e.g., computer system 300) causes the capture of one or more images of an anatomy of a patient using the imaging devices 618.

An imaging device 618 can include any device capable of detecting sound or electromagnetic waves and assembling a visual representation of the detected waves. Imaging devices 618 can collect waves from any part of the electromagnetic spectrum or sounds at any range of frequencies, often as a matrix of independently acquired measurements that each represent a pixel of a two- or three-dimensional image. These measurements can be taken simultaneously or in series via a scanning process or a combination of methods. Some pixels of an image produced by an imaging device 618 can be interpolated from direct measurements representing adjacent pixels in order to increase the resolution of a generated image. Example imaging devices (e.g., monitors 112, imaging system 136) are illustrated and described in more detail with reference to FIG. 1.

The imaging devices 618 can receive or generate imaging data from a plurality of imaging devices 618. The plurality of imaging devices 618 can include, for example, cameras attached to the robotic arm 612, cameras mounted to the ceiling or other structure above the surgical theater, cameras mounted on a tripod or other independent mounting device, body cameras worn by the surgeon or other surgical staff, cameras incorporated into a wearable device, such as an augmented reality device like Google Glass, Microsoft HoloLens, etc., cameras integrated into an endoscopic, microscopic, laparoscopic, or any other camera or imaging devices 618 (e.g. ultrasound) present in the surgical theater. The imaging device 618 can include any algorithm or software module capable of determining qualitative or quantitative data from medical images, which can be, for example, a deep learning algorithm that has been trained on a data set of medical images. An imaging device 618 can further refer to a device used to acquire medical imagery by any means including magnetic resonance imaging (MRI), computed tomography (CT), X-ray, positron emission tomography (PET), ultrasound, arthrography, angiography, myelography, etc.

The implant 620 is a structure embedded within the body of a patient. The implant 620 can consist of one piece, or can include multiple implant components 622. Surgical implantation is described in more detail with reference to FIGS. 4A-4B. The implant can be rigid, flexible, or combine both rigid and flexible components. The implant 620 can be made of synthetic materials such as biocompatible metals, metal alloys, plastics, resins, ceramics, etc., or can alternatively be made of organic components such as tissues harvested or derived from humans or animals. In embodiments, an implant 620 can include both organic and inorganic implant components 622. Implants 620 can be customized to fit a patient's unique physiology or to perform a specific function. Implants 620 can provide reinforcement to a patient's physiology or can replace, repair, or improve the function or performance of a part of the patient's body, such as replacing a knee joint or inserting a stent to open a vein or block off an aneurism. An implant 620 can also be a prosthetic or therapeutic device that is attached to the patient's body. An implant 620 is characterized by being surgically attached to the patient, however, the entirety of the implant 620 need not be fully embedded within the patient, and part or all of the implant 620 can be exposed even after patient recovery. In such cases, implant 620 and implant components 622 will relate to parts of such implants 620 that are in contact with the patient.

An implant component 622 is a discrete part or subassembly of an implant 620. An implant component 622 can be made of any biocompatible material that will not illicit an immune response from the patient. Biocompatible materials can be organic or inorganic. Examples of inorganic biocompatible materials include metals such as titanium, metal alloys such as titanium alloys, stainless steel, and cobalt-chromium alloy, ceramics such as zirconia and bioglass, thermoplastics such as polyvinylchloride (PVC), polyethylene (PE), polypropylene (PP), polytetrafluoroethylene (PTFE), and polymethylmethacrylate (PMMA), and other resins and materials including alumina, hydroxyapatite, medical-grade silicone, trimethyl carbonate, TMC NAD-lactide, etc. Implant components 622 can additionally include organic structures such as organs harvested from human or animal donors or tissues and compounds that can be grown or otherwise synthesized in a lab. An implant 620 can consist of a single implant component 622. Implant components 622 can be customizable.

The cloud 624 is a distributed network of computers including servers and databases. The cloud 624 is implemented using components of the example computer system 300 illustrated and described in more detail with reference to FIG. 3. The cloud 624 facilitates communication links among the components of the system 600. The cloud 624 can be a wired and/or a wireless network. The cloud 624, if wireless, can be implemented using communication techniques such as Visible Light Communication (VLC), Worldwide Interoperability for Microwave Access (WiMAX), Long Term Evolution (LTE), Wireless Local Area Network (WLAN), infrared (IR) communication, Public Switched Telephone Network (PSTN), radio waves, and other communication techniques known in the art (see FIG. 3). The cloud 624 can be a private cloud 624, where access is restricted by isolating the network such as preventing external access, or by using encryption to limit access to only authorized users. Alternatively, a cloud 624 can be a public cloud 624, where access is widely available via the internet. A public cloud 624 may not be secured or may include limited security features.

A patient database 626 stores patient data including electronic medical records, diagnosed conditions, patient-specific baseline values such as heart rate, blood pressure, etc., and medical imaging data. The patient database 626 can additionally include personal identifiable information, insurance and billing information, personal contact information, and emergency contact information. The patient database 626 can also contain legal documentation such as consent to perform a procedure. The patient database 626 can further include familial relationships and genetic data to facilitate a comprehensive family history. In some aspects of the present invention, patient database 626 stores medical images that can be used by the implant module 634, route planning module 636, simulation module 638, and/or procedure module 640 to determine aspects of the patient's anatomy that can affect the procedure, implant 620, or implant components 622. The medical images can additionally include annotations from a practitioner and/or algorithm that can indicate tissue types, structures, and/or other anatomical features which can be used by the implant module 634, route planning module 636, simulation module 638, and/or procedure module 640 to modify the procedure, implant 620, or implant components 622.

A procedure database 628 can store data related to surgical or therapeutic procedures including the type of procedure, actions taken during the procedure, what is treated by the procedure, possible contraindications or complications, and resources required such as personnel, hard goods, and consumables. The procedures can include the installation of one or more implants 620 and can include data such as the type of implant 620, number of implant components 622, and manner in which the implant 620 and implant components 622 were installed. The procedure database 628 can additionally store route data, which can include at least one incision site, at least one implant site, and one or more routes through the patient from the one or more incision sites to the one or more implant sites. The data can additionally include parameters of each path, such as the maximum dimensions of implants 620 or implant components 622 that can be accommodated. When multiple routes exist, a score or rank can be assigned to prioritize preferred routes. Preferred routes will generally accommodate implants 620 or implant components 622 with larger dimensions, or alternatively provide greater margins. Similarly, preferred routes will avoid sensitive tissues, such as blood vessels, nervous tissues, organs, etc.

An implant database 630 stores data related to one or more implants 620. The implant 620 data can include the type of implant 620, the location where the implant 620 is installed, the number and type of implant components 622, and specific properties of the implant components 622 including dimensions, materials, and manufacturing methods. The implant 620 data can additionally include physical characteristics such as hardness, flexibility, etc. The implant database 630 can additionally include data related to the procedures used to install the implants 620, patient information about the patients in whom the implants 620 are installed, and patient outcomes. The implant database 630 can be populated by a separate system that customizes the implant 620 or implant components 622, or by a database such as a third-party source that can include the manufacturer of an implant 620 or implant components 622.

The base module 632 uses at least one imaging device 618 to acquire one or more images of a patient, specifically the surgical site encompassing the location where the implant 620 is to be installed. The base module 632 is implemented using computer hardware, computer software, computer firmware, or a combination thereof, e.g., as illustrated and described in more detail with reference to FIG. 3. The implant module 634 is triggered, receives the image data, and queries the implant database 630. The implant module 634 is implemented using computer hardware, computer software, computer firmware, or a combination thereof, e.g., as illustrated and described in more detail with reference to FIG. 3. In some embodiments, the system 600 generates a virtual anatomy of the patient based on the one or more images. For example, the virtual anatomy may comprise a virtual incision site and a virtual implant site corresponding to the incision site and the implant site, respectively.

In embodiments, the system 600 segments the surgical implant 620 into multiple implant components 622 based on one or more images of the patient's anatomy. Each implant component 622 has a size and a shape compatible with the implant site. The surgical implant design is selected and is segmented into one or more implant components 622. In some embodiments, the system 600 segments a surgical implant design or a three-dimensional virtual implant model (e.g., a computer-aid design (CAD) model, virtual solid models, surface models, etc.) of the surgical implant into multiple virtual implant components based on one or more images of the patient's anatomy. in some embodiments, the system 600 segments the surgical implant based on a segmentation plan. The segmentation plan can be generated based on the design of the implant, features at the implantation site, size of the implantation site, etc. The segmentation plan can be implemented to segment the implant into a target number of sub components (e.g., two, three, four, five separate virtual implant components) capable of being at least partially assembled within the body. Postoperative loading can be analyzed to determine the segmentation locations such that the assembled implant is configured to withstanding planned loading.

Each virtual implant component has a virtual size and a virtual shape compatible with a virtual implant site corresponding to the implant site. In some embodiments, a machine learning model (e.g., ML model 216, as illustrated in FIG. 2) may be used to perform segmentation of the surgical implant 620, the surgical implant design, or the three-dimensional virtual implant model of the surgical implant. In some embodiments, the system 600 designs virtual implant components based on the images or virtual anatomy of the patient. For example, the virtual implant components may be designed to form a three-dimensional virtual implant model representing the surgical implant.

Each implant component 622 or virtual implant component is then assessed for whether it needs to be modified. Implant components 622 or virtual implant components are modified as necessary, and then the customized implant components 622 are saved to the implant database 630. The customized implant components 622 are received by the base module 632, and the route planning module 636 is triggered. The route planning module 636 receives image data and data from the procedure database 628, identifies at least one implant site and at least one incision site. In some embodiments, a machine learning model (e.g., ML model 216, as illustrated in FIG. 2) may be used to perform identification of the at least one implant site and the at least one incision site.

The route planning module 636 generates possible routes or delivery paths through which implant components 622 can be moved from the incision site to the implant site. In some embodiments, the route planning module 636 identifies at least one virtual implant site and at least one virtual incision site, and generates possible routes through which the virtual implant components can be moved from the virtual incision site to the virtual implant site. In some embodiments, a machine learning model (e.g., ML model 216, as illustrated in FIG. 2) may be used to perform identification of the at least one virtual implant site and the at least one virtual incision site. The route planning module 636 is implemented using computer hardware, computer software, computer firmware, or a combination thereof, e.g., as illustrated and described in more detail with reference to FIG. 3.

Constraints or other selection criteria are determined based upon parameters of the implant components 622 including the dimensions of the largest implant components 622, dimensions, curvature, or other features of the patient's anatomy, dimensions, curvature, or other features of the available routes, capabilities of the robotic surgical system or other delivery instruments, maneuverability of the robotic surgical system or other delivery instruments, availability of surgical tools, time constraints of the patient or physician, or other factors. Constraints for virtual implant components may be determined based upon parameters of the virtual implant components including the dimensions of the largest virtual implant components, dimensions, curvature, or other features of the patient's virtual anatomy, dimensions, curvature, or other features of the available routes, capabilities of the robotic surgical system or other delivery instruments, maneuverability of the robotic surgical system or other delivery instruments, availability of surgical tools, time constraints of the patient or physician, or other factors. A route is selected and is evaluated for compliance with the identified constraints. Compliant routes are added to a list of valid routes, and the list of valid routes is saved to the procedure database 628 and received by the base module 632.

In embodiments, the system 600 simulates the passage of multiple implant components via one or more routes by the surgical robot 602. For example, the simulation module 638 is triggered, receiving route planning data and the customized implant components 622. For each route, simulations are performed such that each implant component 622 is inserted through the identified route and then installed at the implant site. If the implant component 622 is able to navigate from the incision site to the implant site and can be assembled into the implant 620, the route is added to a list of verified routes. In an example, the human organs are observed from the inside of the abdominal cavity, and the use of various instruments to grasp, cut or clip the organs is simulated. In an example, a simulator uses a computer screen displaying a three-dimensional graphic of the organs being operated on. Surgical tools can be connected to motion sensors and haptic or tactile feedback mechanisms in the simulation.

For each route, virtual simulations may be performed such that each virtual implant component is inserted into the anatomy through the virtual incision site and passed along the identified route. The virtual implant components may then be assembled into the surgical implant design or three-dimensional virtual implant model and virtually installed at the virtual implant site. If the virtual implant component is able to navigate from the virtual incision site to the virtual implant site and can be assembled into the surgical implant design or three-dimensional virtual implant model, system 600 may manufacture the surgical implant according to the segmented surgical implant design or segmented three-dimensional virtual implant model. In some embodiments, virtual simulations may be performed for assembly of the virtual implant components into the surgical implant design or the three-dimensional virtual implant model. Virtual simulations may be performed for the surgical implant design or the three-dimensional virtual implant model positioned at the virtual implant site.

In some embodiments, the system 600 may determine a predicted patient outcome based on the virtual simulations. For example, the system 600 may determine a score for the predicted patient outcome for each delivery path. In some embodiments, the score may reflect a success rate, a risk of damage to the patient, a healing outcome, or other metric. In some embodiments, the route or delivery path may be selected based on the virtual simulation or the score for the predicted patient outcome. In some embodiments, the system 600 may rank the scores for the predicted patient outcomes and may use the ranking to select the routes or delivery paths.

The simulation results including the verified routes or the scores are received by the base module 632 and can additionally include data describing failures that occurred during simulation of routes not included in the list of verified routes. In some embodiments, the system 600 may select at least one of the routes or delivery paths based on the virtual simulation or the simulation results, including the verified routes or the scores. In some embodiments, a machine learning model (e.g., ML model 216, as illustrated in FIG. 2) may be used to perform the selection of the routes or delivery paths. If there are no verified routes, the simulation results can be sent to the implant module 634 for further modification of the implant components 622, otherwise the procedure module 640 is triggered. The procedure module 640 receives the implant components 622 and verified routes and selects a verified route through which each implant component 622 is inserted. The procedure module 640 is implemented using computer hardware, computer software, computer firmware, or a combination thereof, e.g., as illustrated and described in more detail with reference to FIG. 3. The system 600 can generate an assembly plan for assembling the implant. The assembly plan can include, for example, order to assembling components, assembly parameters (e.g., minimum forces, minimum torques maximum forces, maximum torques, tool speeds, etc.), tools, and other data generated based on, for example, routes or delivery paths, configuration of the implantation site and surrounding features, the configuration and capabilities of the surgical robot, user input, etc.

If the implant component 622 cannot be successfully inserted via the selected route, an alternate route can be selected if available. A procedure status is generated and is received by the base module 632. The procedure status can indicate whether one or more routes require modification, thus triggering the route planning module 636, or the procedure status can indicate whether the procedure is complete. If the procedure is complete, then the patient's procedure ends, otherwise the procedure module 640 will be triggered until the procedure is completed.

The implant module 634 receives image data from the base module 632. The implant module 634 additionally queries the implant database 630 for implant 620 designs and selects at least one implant 620 design. Alternatively, a unique or customized implant 620 design can be generated that is not based upon the designs from the implant database 630. The implant 620 is then segmented into at least one implant component 622. The size and shape of the implant components 622 can be based upon the patient's anatomy as represented by the image data.

If the implant component 622 cannot be successfully inserted via the selected route, or if all routes or delivery paths fail to meet a selection criterion such as a route constraint, the system may make certain modifications. For example, the system 600 may modify a particular route such that the implant component 622 can be passed form the incision site to the implant site along a route. The route modifications may comprise routing around locations through which the implant component 622 is not able to pass. In embodiments, the system 600 modifies an implant component or causes the implant component to be modified such that the implant component can be passed from an incision site to an implant site along a route. For example, each implant component 622 is selected and evaluated for whether additional modification is required, and the implant components 622 are modified when necessary. In embodiments, modifying an implant component includes adding a flexible portion to the implant component. For example, modifications can include adding flexible materials or features, such as to a rod, to allow the rod to articulate to navigate through a narrow, curving installation route. Modifications can include replacing a solid structure with a mechanical structure such that the implant component 622 can begin the procedure with a collapsed profile to allow navigating along the selected installation route and then can be expanded when the implant component 622 arrives at the implant site. When all implant components 622 have been modified as necessary, the customized implant 620 and implant component 622 designs are saved to the implant database 630 and the implant components 622 are sent to the base module 632. The implant module 634 can additionally receive data from the simulation module 638 if no valid routes can be identified to navigate one or more implant components 622 from the incision sites to the implant site.

If a virtual implant component cannot be successfully inserted into the virtual anatomy via the selected route, an alternative route can be selected if available, or system 600 may modify the route, the virtual implant component, the virtual segmentation of the surgical implant design, or the incision site and the implant site. The system 600 may modify a particular route such that the virtual implant component can be passed form the virtual incision site to the virtual implant site along a route. The route modifications may comprise routing around or otherwise excluding locations through which the virtual implant component is not able to pass. The virtual implant component may be modified, for example, by replacing a solid structure with a mechanical structure within the surgical implant design. In some embodiments, modifications can include adding flexible materials or features, such as to a rod, to the surgical implant design. In some embodiments, the segmentation of the virtual implant component may be modified. For example, system 600 may modify the number of segments making up the surgical implant design, the shape of the segments, the positioning of the segments, or other features of the segmentation. In some embodiments, the incision site and the implant site may be modified based on the virtual simulation.

In embodiments, the system 600 determines one or more routes from an incision site to an implant site based on route constraints. For example, the route planning module 636 receives image data acquired from at least one imaging device 618 and the implant components 622 from the base module 632. The route planning module 636 additionally queries the procedure database 628 for data on medical or surgical procedures including the installation of one or more implants 620. At least one implant site and at least one incision site are identified, and possible routes through which the implant components 622 can be navigated are generated. Constraints are identified for the one or more implant components 622 such as their maximum physical dimensions and can additionally include safety margins. A route is selected from the generated routes and is evaluated for compliance with the identified constraints. A route may be noncompliant if it cannot accommodate the largest implant components 622 or the route does not provide adequate safety margins, which could result in harm to sensitive tissues during installation of implant components 622. If the route is compliant it is added to a list of valid routes and the remaining routes are assessed. When all routes have been assessed, the valid routes are saved to the procedure database 628 and are sent to the base module 632.

The simulation module 638 receives route data generated by the route planning module 636 and implant components 622 customized by the implant module 634 from the base module 632. For each route, simulations are performed for the insertion of each implant component 622. In embodiments, a route is identified via which an implant component can be passed from the incision site to the implant site by the surgical robot 602 based on simulations. If all of the implant components 622 are able to navigate from the incision site to the implant site without encountering an issue, such as being physically unable to fit through the space or by encroaching on clearances required for sensitive tissues, and the implant components 622 can be assembled into an implant 620, the route is added to a list of verified routes. The process is repeated for all routes and the verified routes are saved to the procedure database 628 and sent to the base module 632. In addition to the verified routes, data from the failed routes, such as the implant components 622 that were unable to navigate via each route and the manner in which they failed, can be sent to the base module 632.

The procedure module 640 receives implant components 622 and verified routes from the base module 632. A route is selected from the list of verified routes and an implant component 622 is inserted via the route. If the insertion is successful, the process is repeated for all remaining implant components 622. If the insertion of an implant component 622 is unsuccessful, another route is selected from the list of verified routes. When all implant components 622 have been inserted, the implant components 622 are assembled to form the implant 620. A procedure status is generated and sent to the base module 632. The procedure status can include the stage of the procedure, such as whether the procedure has been completed or is in progress, and can also include information such as whether all verified routes have been attempted unsuccessfully. In such cases, data relevant to the failures can be provided to the base module 632, such as data about the implant component 622 that was unsuccessfully inserted, and details of the attempt, such as where the implant exceeded allowable margins or contacted surrounding tissues.

The system 600 can perform simulations using virtual models that can include two or three-dimensional models to evaluate, for example, implant assembly, implant design, one or more steps of a surgical procedure (or an entire procedure), predicted events, outcomes, etc. The simulations can be used to identify and assess implantation parameters (e.g., implantation time, implantation complexity, etc.), access paths or routes, stresses (e.g., stresses in implant components, stresses in anatomical features, etc.), strains, deformation characteristics (e.g., load deformation characteristics in implants/anatomy, load distributions in implants/anatomy, etc.), fracture characteristics (e.g., fracture toughness), fatigue life, etc. The virtual model can include exemplary implant components, exemplary assembled implants, portions of a patient's anatomy, exemplary end effectors, exemplary instruments, exemplary access tools, or the like.

The simulations can be generated using three-dimensional models, surfaces, and virtual representations. The simulations can be generated by CAD software, finite element analysis (FEA) software (e.g., analyze stress in components), and robotic control software/programs based on patient data (e.g., images, scans, etc.), implant design data, or the like. A user can view, manipulate (e.g., rotate, move, etc.), modify, set parameters (e.g., boundary conditions, properties, etc.), and interact with the models. The control parameters, robotic kinematics, and functionality can be used to generate the simulations. In some embodiments, models of implants, installation tool, insertion instruments, end effectors of a robotic system, etc. are used to perform virtual procedures on virtual anatomical models. Virtual simulations of surgical procedures can be performed in which-user selected robotic surgical steps and physician steps are used to generate, modify, and select surgical plans, surgical robot configurations, or the like.

Pre-operative simulations can be performed for different surgical robots using pre-operative patient data (e.g., pre-operative scans, images, etc.). A surgical robot for performing a surgical procedure or portion thereof can be selected based on the simulation(s). This allows a healthcare provider to select a surgical robot suitable for a particular procedure for assembling implants. Additionally, the simulations can be used to generate, modify, and/or verify surgical plans. In some embodiments, a configuration of the surgical robot is selected based on the simulations. For example, multiple simulations can be performed for a surgical robot in different configurations (e.g., the surgical robot having different end effectors) and using different surgical techniques for assembling implants. The healthcare provider can select the surgical robot configuration and surgical plan based, at least in part, on the simulations. End effectors and tools of the surgical robot, imaging equipment, and manual equipment can be selected based on the simulations.

FIG. 7 illustrates a structure of an example database for performing route planning for robotic surgical implant installation, in accordance with one or more embodiments. FIG. 7 shows the patient database 626. The patient database 626 includes data about one or more patients and can include electronic medical records. Likewise, embodiments of the patient database 626 can include different and/or additional components or can be connected in different ways.

The patient database 626 can include personally identifiable information such as name, date of birth, address, insurance information, etc. A patient database 626 can additionally include information about a patient's health or medical history such as diagnosed conditions, allergies, medications, normal baseline vital sign ranges for the patient, etc. The patient database 626 can be populated by medical professionals such as a patient's physician, specialists such as surgeons, therapists, or any other medical professionals including nurses, emergency medical technicians, paramedics, etc. The patient database 626 additionally stores images acquired by the base module 632 using at least one imaging device 618 and can also store data related to the patient from the implant module 634, route planning module 636, simulation module 638, and procedure module 640.

The patient database 626 is used by the implant module 634, route planning module 636, simulation module 638, and procedure module 640. The patient database 626 can include, for example, medical images produced by imaging device 618, which can be, for example, X-rays, CT (computed tomography) scan, positron emission tomography (PET) scan, MRI (magnetic resonance imaging), ultrasound, or nuclear medicine imaging. Medical images can further include still images or videos from a camera either external or internal to the patient, such as an endoscope, laparoscope, etc. Medical image data can include metadata from the images, such as the specific model of equipment used to generate the image, the date and time the image was taken, the geographic location of the image, the anatomical location of the image, and the practitioner(s) who performed the imaging.

Additionally, the medical image data can include annotations from a practitioner and/or algorithm that indicate tissue types, structures, and/or other anatomical features. The patient database 626 can contain 3D anatomical representations of the user generated by medical images, such as, for example, using the cross-sectional imaging data provided by an MRI device to convert pixels from individual cross-sections into voxels defining a 3D volume by extrapolating the volume between at least two pixels of at least two medical images, wherein the volume can be determined by the distance between cross-sections that the MRI machine generated.

The 3D anatomical representation can further be generated by combining cross-sectional images from two or more axial planes of an imaging modality, such as MRI. In one example, the patient database includes an MRI scan of a male patient, age 46. The MRI can show portions of the hip joint that need to be replaced with prosthetic implants. The patient data can also include a prescription for the removal and replacement of portions of the pelvis and femur that form the patient's hip joint. The patient database 626 can include a 3D model of the patient's hip joint and the prosthetic that needs to be implanted.

In embodiments, a visible light imaging modality is used, such as encapsulating color images, e.g., in JPEG format, where the images captured include specialty-specific acquisition context metadata. The visible-light imaging modality can be used by a surgical robot (see FIGS. 4A-4B) for performing endoscopy (including fiberoptic endoscopy or rigid scope endoscopy), angioscopy, arthroscopy, bronchoscopy, colposcopy, etc. The visible-light imaging modality can be used by a surgical robot for performing light microscopy for anatomic pathology (e.g., transmission light microscopy and reflection light microscopy for cytology or histology), surgical microscopy (e.g., images produced by an operating microscope used in cardiothoracic surgery, neurologic surgery, ophthalmic surgery, etc.), anatomic pathology, dermatology, aesthetic (cosmetic) or reconstructive plastic surgery, etc.

In embodiments, the imaging devices use a computer tomography (CT) modality to generate a two-dimensional (2D) or three-dimensional (3D) image of the scanned region of interest. The CT images are a compilation of computer-processed X-ray images taken at a range of angles around the region to produce a single cross-sectional image. The region can be moved forward within the imaging device to scan a next cross-section similarly. The cross-sectional images can be viewed side by side or stacked on top of one another to create a 3D scan of the region. In embodiments, an imaging device uses an MRI imaging modality to provide highly detailed images of tissue structures. The imaging device detects and processes the signals generated when hydrogen atoms, which are abundant in tissue, are placed in a strong magnetic field and excited by a resonant magnetic excitation pulse.

FIG. 8 illustrates a structure of an example database 628 for performing route planning for robotic surgical implant installation, in accordance with one or more embodiments. FIG. 8 shows the procedure database 628. The procedure database 628 includes data about one or more procedures. Likewise, embodiments of the procedure database 628 can include different and/or additional components or can be connected in different ways.

The data in the procedure database 628 can include the steps of the procedure and can also include a plurality of alternative steps or responses to issues or complications. The data can additionally include one or more parameters or conditions by which the procedure can be halted or aborted. The data can additionally include actions taken, measurements taken such as vital signs, and personnel involved, including the patient, the surgeon, and any other personnel and equipment used. The procedure database 628 can be populated by surgeons, nurses, or any other medical professionals or technicians and can include relevant portions of patients' electronic medical records pertaining to a procedure.

In embodiments, the procedure database 628 can additionally include patient data such as the data in patient database 626 that may be relevant to one or more procedures. Procedures can include implant procedures or therapies that involve segmentation and customization of an implant 620. The procedure database 628 can also include procedures that are not relevant to implant procedures. The procedure database 628 is used by the route planning module 636, simulation module 638, and procedure module 640. In one example, the procedure database 628 contains data on a hip joint replacement surgery. The procedure database 628 indicates a procedure for a minimally invasive robotic surgery wherein portions of the pelvis and femur that form the patient's hip joint are removed and replaced with a prosthetic implant. In such examples, the procedure data can also include instructions for a customized implant 620 and implant components 622 and can additionally include installation route data.

The procedure database 628 can additionally include one or more incision sites, one or more implant sites, and a plurality of routes between one or more incision sites and one or more implant sites. The routes can be further qualified as valid routes capable of accommodating implant components 622 for the installation of an implant 620 and can be further verified by the simulation module 638. Routes that have been verified can additionally be scored, ranked, or otherwise identified by preference based upon the routes' ability to accommodate implant components 622, which can include physical clearances or the proximity of sensitive tissues such as nervous tissues, blood vessels, organs, etc., to the route.

FIG. 9 illustrates a structure of an example database for performing route planning for robotic surgical implant installation, in accordance with one or more embodiments. FIG. 9 shows the implant database 630. The implant database 630 stores data about implants 620 and implant components 622. Likewise, embodiments of the implant database 630 can include different and/or additional components or can be connected in different ways.

The data can include the type of implant 620, the location of the implant 620, one or more implant components 622 that make up the implant 620, the materials of each implant component 622, and the properties of those materials. For example, the implant 620 materials can include one or more of any biocompatible material including alumina, bioglass, cobalt-chromium alloy, hydroxyapatite, medical-grade silicone, polyvinylchloride (PVC), polyethylene (PE), polypropylene (PP), polytetrafluoroethylene (PTFE), polymethylmethacrylate (PMMA), stainless steel, trimethyl carbonate, TMC NAD-lactide, titanium and titanium alloys, zirconia, etc. The implant 620 data can further include installation data and patient outcomes.

Figure 10:
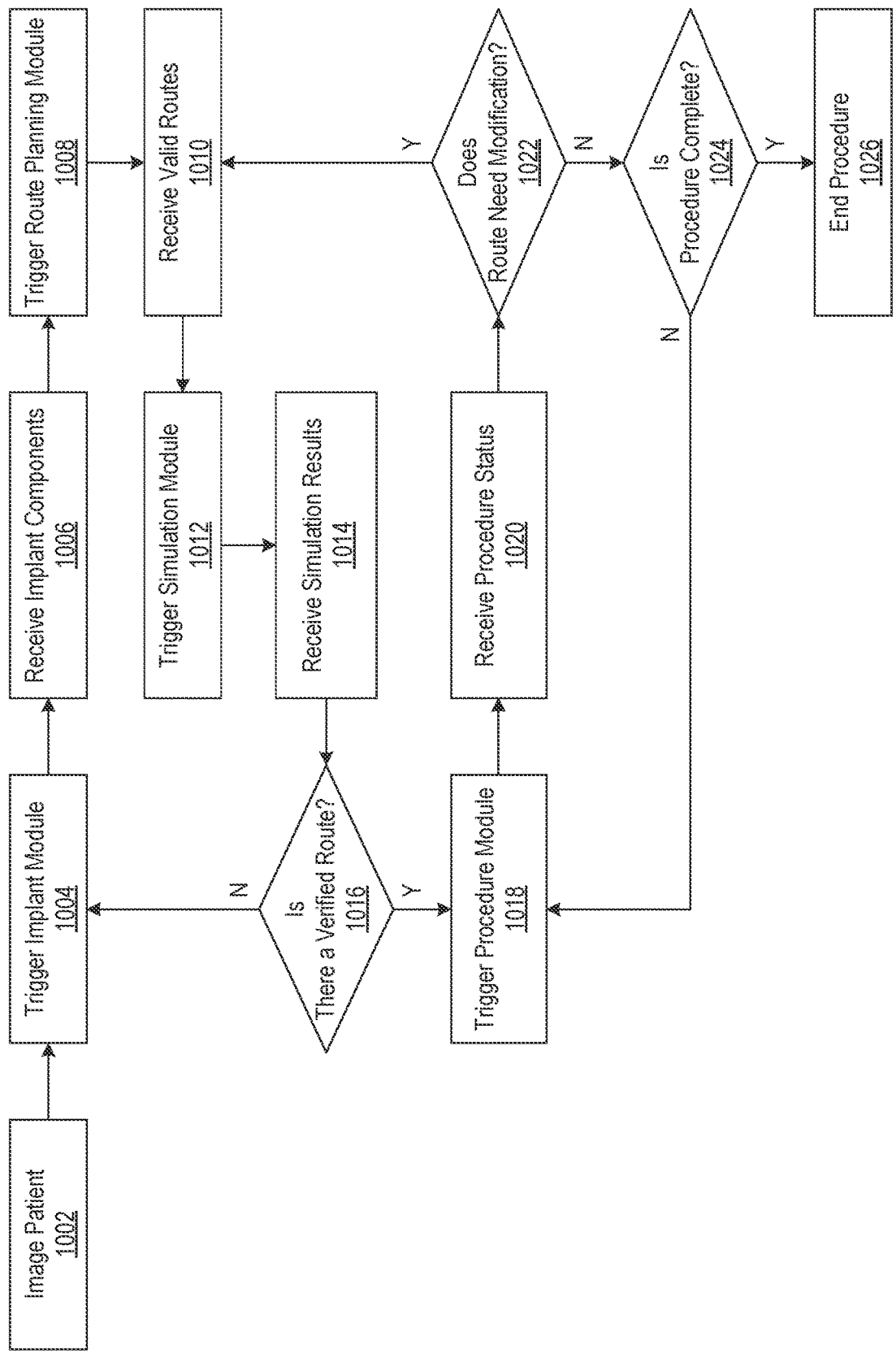
FIG. 10 is a flow diagram illustrating an example process for performing route planning for robotic surgical implant installation, in accordance with one or more embodiments.

FIG. 10 is a flow diagram illustrating an example process for performing route planning for robotic surgical implant installation, in accordance with one or more embodiments. An example operating room 102 is illustrated and described in more detail with reference to FIG. 1. In embodiments, the process of FIG. 10 is performed by the operating room system base module 632. The operating room system base module 632 is illustrated and described in more detail with reference to FIG. 6. In other embodiments, the process of FIG. 10 is performed by a computer system, e.g., the example computer system 300 illustrated and described in more detail with reference to FIG. 3. Particular entities, for example, the console 108 or the robotic surgical system 160, perform some or all of the steps of the process in other embodiments. The console 108 and the robotic surgical system 160 are illustrated and described in more detail with reference to FIG. 1. Likewise, embodiments can include different and/or additional steps, or perform the steps in different orders.

In step 1002, the base module 632 images the patient, including the location where an implant 620 is to be installed, using an imaging device 618. The imaging can be performed using at least one of any imaging methods, including both visual light and radiologic modalities. In preferred embodiments, however, at least one imaging modality is a radiologic modality such as CT, MRI, PET, etc. In some embodiments, a single imaging modality can be used, such as MRI. In other embodiments, multiple imaging modalities can be used, such as MRI, CT, and ultrasound. In some embodiments, a single image frame can be used. In other embodiments, multiple image frames can be used. When multiple image frames are used, multiple images can be used to create a higher resolution two-dimensional image. The same method can be applied in slices of varying depths, or from varying orientations, to create a three-dimensional representation of the implant site. In embodiments, imaging is performed on the right hip of a patient named John Smith using MRI. The image data can be further saved to the patient database 626.

In embodiments, the system 600 uses sound waves or acoustic energy (ultrasound imaging modality) in a frequency above human hearing (20,000 Hertz (Hz) or 20 kHz). A diagnostic sonographic scanner can be used in a frequency range of 2 to 18 MHz, hundreds of times greater than the limit of human hearing. In embodiments, X-ray imaging is performed using electromagnetic radiation of extremely short wavelength and high frequency, with wavelengths ranging from about $10^{-8}$ to $10H^2$ meters (m) and corresponding frequencies from about $10^{16}$ to $10^{20}$ Hz.

In embodiments, the system 600 performs one or more multi-modality analyses in which one or more multi-sensing devices (e.g., multi-modality imagers, multiple imaging machines, etc.) perform (sequentially or concurrently) multiple scans/tests, such as CT scans, radiation tests, sound tests, optical tests, acoustic tests, photoacoustic tests, combinations thereof, or the like. In embodiments, a multi-modality image can simultaneously image a target region to capture images with matching perspectives relative to the target region such that features from one image can be overlayed onto another, features from multiple images can be stitched together to form a composite image, and/or cross-image features identification can be performed. In embodiments, tests are performed during one or more scans of the target region. In a single scan test, the system 600 can concurrently perform multiple tests while moving along the tissue sample. In multiple scan tests, the system 600 sequentially performs tests during corresponding scans and/or concurrently performs multiple tests during each scan. The system 600 can perform different testing, imaging, and/or scanning protocols based on the analysis to be performed.

The system 600 can facilitate communication with another robotic surgical system, doctor, surgeon, or other medical professional by providing results (e.g., multi-modality data, raw data, visualizations of the data, and the like) from the test(s) in real time. Further, the system 600 can combine the results from imaging device(s) to provide a diagnosis of a tissue sample, target region, surgical site, or combinations thereof. In surgical procedures, the results can be automatically transmitted to a surgical robot that analyzes the results to perform one or more surgical steps. The surgical robot can request additional information from the system 600 to, for example, complete a surgical step, confirm completion of a surgical step, plan a surgical step, plan a series of surgical steps, or the like. For example, the surgical system 400 at FIG. 4A can receive multi-modality results from the system 600 to perform a multi-modality-guided robotic surgical step. In embodiments, the results are displayed via display 422 for viewing by the surgical team, as shown in FIG. 4A. Features of exemplary viewable multi-modality results are discussed in connection with FIG. 15. Additionally, or alternatively, the results can be viewable via console 420 by a user 421 of FIG. 4A while, for example, monitoring or performing one or more surgical steps.

In embodiments, the system 600 captures images of a region of interest of a patient's anatomy using a first imaging device and a second imaging device. The first imaging device uses a first imaging modality and the second imaging device uses a second imaging modality. The system 600 uses the different types of detected wavelengths individually or in combination for a variety of medical and non-medical applications. In embodiments, multi-modal image fusion is performed. A first set of (X,Y) data points and a second set of (X,Y) data points are fused by amalgamating two or more images from single or multiple imaging modalities, such as positron emission tomography, single photon emission computed tomography, computed tomography, or magnetic resonance imaging, into a single distinct image having more-detailed anatomical and spectral information. The benefits of the embodiments are to improve the quality of an image while preserving the most desirable and relevant characteristics of each in order to make the image more usable for clinical diagnosis and treatment procedures. In embodiments, feature processing, machine learning, and sparse representation are used to learn informative characteristics that portray the patterns and regularities in each set of data points.

In step 1004, the base module 632 triggers the implant module 634, which receives the image data acquired from at least one imaging device 618. In embodiments, the ML system 200 illustrated and described in more detail with reference to FIG. 2 extracts features from the images and uses a combination of digital image processing, computer vision, and image segmentation to partition an image into multiple image segments, also known as image regions or image objects (sets of pixels). The embodiments simplify and/or change the representation of the image into segments that are more meaningful and easier to analyze. The methods disclosed herein can be used to locate objects and boundaries (lines, curves, etc.) in images. The methods can assign a label to each pixel in an image such that pixels with the same label share certain characteristics. In embodiments, the set of segments generated cover the entire image, or at least a set of contours extracted from the image. Each of the pixels in a segment can be similar with respect to some characteristic or computed property, such as color, intensity, or texture. Adjacent segments are different with respect to the same characteristic(s). When applied to a stack of images in medical imaging, the resulting contours after the image segmentation can be used to create two-dimensional (2D) or three-dimensional (3D) reconstructions with the help of interpolation algorithms, such as marching cubes.

In embodiments, the implant module 634 improves in identification of the image segments over time. The implant module 634 can detect edges of the sample from the reference segment. For example, the implant module 634 identifies edges from a captured image, Picture 1, defining bone tissue, as the reference segments using the ML system 200. In embodiments, edges can even be manually identified by a doctor over the user interface. For example, the implant module 634 identifies edges defined by a contrast in the magnitude of light of gray-scale images. Successively, the implant module 634 can label a segment enclosed by the identified edges by comparing the detected images to similar previously acquired images. For example, the implant module 634 labels a segment bound by the detected edges by comparing the image with a database of similar images, and determining the segment that constitutes bone tissue. The segment can further be identified as a specific structure, such as the femur of a patient's right leg.

The implant module 634 further queries the implant database 630 for implant designs and selects an implant design. The implant design is optionally virtually segmented into a plurality of implant components 622. Each implant component 622 is evaluated for further customization and the implant components 622 are modified if necessary. When all implant components 622 have been modified, the customized implant 620 and implant components 622 are saved to the implant database 630.

In step 1006, the base module 632 receives the customized implant components 622 from the implant module 634. In embodiments, at least one implant component 622 is customized to be expandable. This customization changes the implant component 622 from a solid volume measuring 3 cm×3 cm×5 cm such that in its collapsed form the implant component 622 has a volume of 1 cm×1 cm×5 cm. In other embodiments, an implant component 622 material is changed from a titanium metal alloy to a more flexible polypropylene. In further embodiments, an implant component 622 is further segmented into two segments to accommodate installation via the route parameters.

In step 1008, the base module 632 triggers the route planning module 636, which receives from the implant module 634 the image data acquired from the at least one imaging device 618 and the implant components 622. In embodiments, the image data is MRI imagery of the abdomen and proximal legs of patient John Smith to encompass the hips, where an implant will be installed, and probable incision sites. Alternatively, the route planning module 636 receives a reference to a location in the patient database 626 where the image data is stored. In embodiments, a series of MRI images of John Smith's right hip is sent to the route planning module 636. Additionally, the route planning module 636 receives information about the implant components 622 that, when assembled, will form the implant 620 to be installed to reconstruct John Smith's right hip joint.

The route planning module 636 further queries the procedure database 628 and uses the data to identify an implant site and at least one incision site. The route planning module 636 generates routes between the at least one incision site and the at least one implant site, identifying constraints for the implant components 622 such as identifying the maximum dimensions of the largest implant components 622. Similarly, the route planning module 636 identifies the clearance or margins required to navigate the implant components 622 safely through the patient's body. Each route is evaluated for compliance with the constraints, and those that are compliant are added to a list of valid routes. When all routes have been assessed, the list of valid routes is saved to the procedure database 628. In embodiments, detailed data can be saved for each of the analyzed routes, such as the minimum clearances for compliant routes, which routes were noncompliant, and the reason the routes were noncompliant.

In embodiments, the system 600 (see FIG. 6) determines the route constraints or performs route planning based on a clearance at an implant site required for assembly of the surgical implant 620 from the implant components 622. For example, in step 1010, the base module 632 receives the valid routes from the route planning module 636. The routes include at least one path between an incision site and the implant site. The routes are capable of accommodating the implant component 622 constraints, such as maximum dimensions, which can represent the maximum height or width of implant components 622. The routes can additionally accommodate varying clearance margins depending on the type of tissues along the selected route and can further identify tissue sensitivities and required clearances to avoid possible injury of sensitive tissues during installation of implant components 622. In embodiments, five valid routes are received, each capable of accommodating all of the implant components 622.

In step 1012, the base module 632 triggers the simulation module 638, which receives the valid route data and the implant components 622. For each route and each implant component 622, simulations are performed that include navigating each implant component 622 from the incision site to the implant site via the route selected by the route planning module 636. For each implant component 622, the simulation module 638 determines whether the implant component 622 can be successfully navigated to the implant site without becoming stuck or without encroaching on clearances of anatomical structures such as sensitive tissues, including blood vessels and nerve tissue. When simulations have been completed for the navigation of all implant components 622 to the implant site via the selected route, the simulation module 638 simulates the assembly of the implant components 622 within the patient to form a completed implant 620. Routes capable of facilitating the movement and assembly of all implant components 622 are added to a list of verified routes.

In step 1014, the base module 632 receives the simulation results from the simulation module 638. The simulation results can include a list of verified routes. The simulation results can additionally include data such as errors or other issues identified during the simulations. In embodiments, the simulation results include three verified routes. In further embodiments, the simulation results include issues encountered during insertion and assembly of the implant components 622, such as an implant component 622 trespassing within the 0.5 cm margin of a nerve and therefore being unable to safely navigate to the implant site, thus resulting in a failed simulation.

In step 1016, the base module 632 determines whether there is at least one verified route that can accommodate the insertion, navigation, and assembly of all implant components 622. If no routes could be verified by the simulation module 638, the base module 632 determines that there are no verified routes and sends received simulation results, including detailed data on the errors encountered, to the implant module 634 for further modification of the implant components 622.

In embodiments, the system 600 (see FIG. 6) inserts each implant component 622 into a patient's anatomy via a route by the surgical robot 602. For example, in step 1018, the base module 632 triggers the procedure module 640, which receives the implant components 622 and verified routes. The procedure module 640 selects a route from the verified routes and selects and inserts an implant component 622. If insertion of the implant component 622 is unsuccessful, the procedure module 640 selects a different verified route, if available. The procedure module 640 repeats the insertion process until all implant components 622 have been successfully inserted into the patient and then assembles the implant components 622 into an implant 620.

If an implant component 622 could not be inserted via any of the verified routes or the implant components 622 could not be assembled, the procedure module 640 generates a procedure status indicating that the procedure is still in progress and that an issue has been encountered preventing the insertion of an implant component 622. The procedure status can additionally include detailed information about the failed insertion of the implant component 622 such as identification of the implant component 622, dimensions of the implant component 622, the locations where the implant component 622 was unable to pass through the patient, and structures that the implant component 622 was unable to navigate around. Alternatively, if the implant components 622 were successfully inserted and assembled into an implant 620 and the procedure is complete, the procedure module 640 generates a procedure status indicating that the implant 620 has been successfully installed and the installation procedure is complete.

In embodiments, the system 600 (see FIG. 6) determines that a particular implant component is unable to be passed from the incision site to the implant site via any of the routes. The system 600 determines one or more locations along the routes through which the particular implant component is unable to be passed. For example, in step 1020, the base module 632 receives a procedure status from the procedure module 640. The procedure status can indicate that the procedure is still in progress and that an implant component 622 was unable to navigate any of the available verified routes. The procedure status can additionally include details about the failed insertion of the implant component 622 such as identification of the implant component 622, dimensions of the implant component 622, the locations where the implant component 622 was unable to pass through the patient, and structures that the implant component 622 was unable to navigate around. Alternatively, the procedure status can include a success message indicating that the procedure has been successfully completed.

In embodiments, the system 600 (see FIG. 6) modifies a particular route such that a particular implant component can be passed from the incision site to the implant site along the particular route. The particular route excludes the one or more locations that the particular implant component is unable to navigate. For example, in step 1022, the base module 632 determines whether modification of one or more routes is necessary. Modification of a route can be required if one or more implant components 622 are unable to be navigated through any of the available verified routes or if the implant components 622 cannot be assembled within the patient. If a route requires modification, the base module 632 triggers the route planning module 636 and sends any available information included in the procedure status received from the procedure module 640. In embodiments, minor modifications can be required and made to an implant component 622 to facilitate successful insertion, navigation, and assembly during a procedure. Such modifications can be assumed to have been attempted during the installation attempt.

In step 1024, the base module 632 determines whether the procedure is complete based upon the procedure status received from the procedure module 640, if the route does not required modification. The procedure is complete if the procedure status received from the procedure module 640 indicates that the implant components 622 have been successfully inserted into the patient and assembled into an implant 620 at the implant site. If the procedure is not complete, the base module 632 triggers the procedure module 640 to continue the procedure.

In step 1026, the implant 620 installation procedure ends if the procedure is complete. Ending the procedure can include any processes or procedures required to terminate the procedure, such as removing tools and materials from the patient, closing any incisions made in the patient, monitoring the condition of the patient, and further providing post-operative treatment and therapy to the patient.

Figure 11:
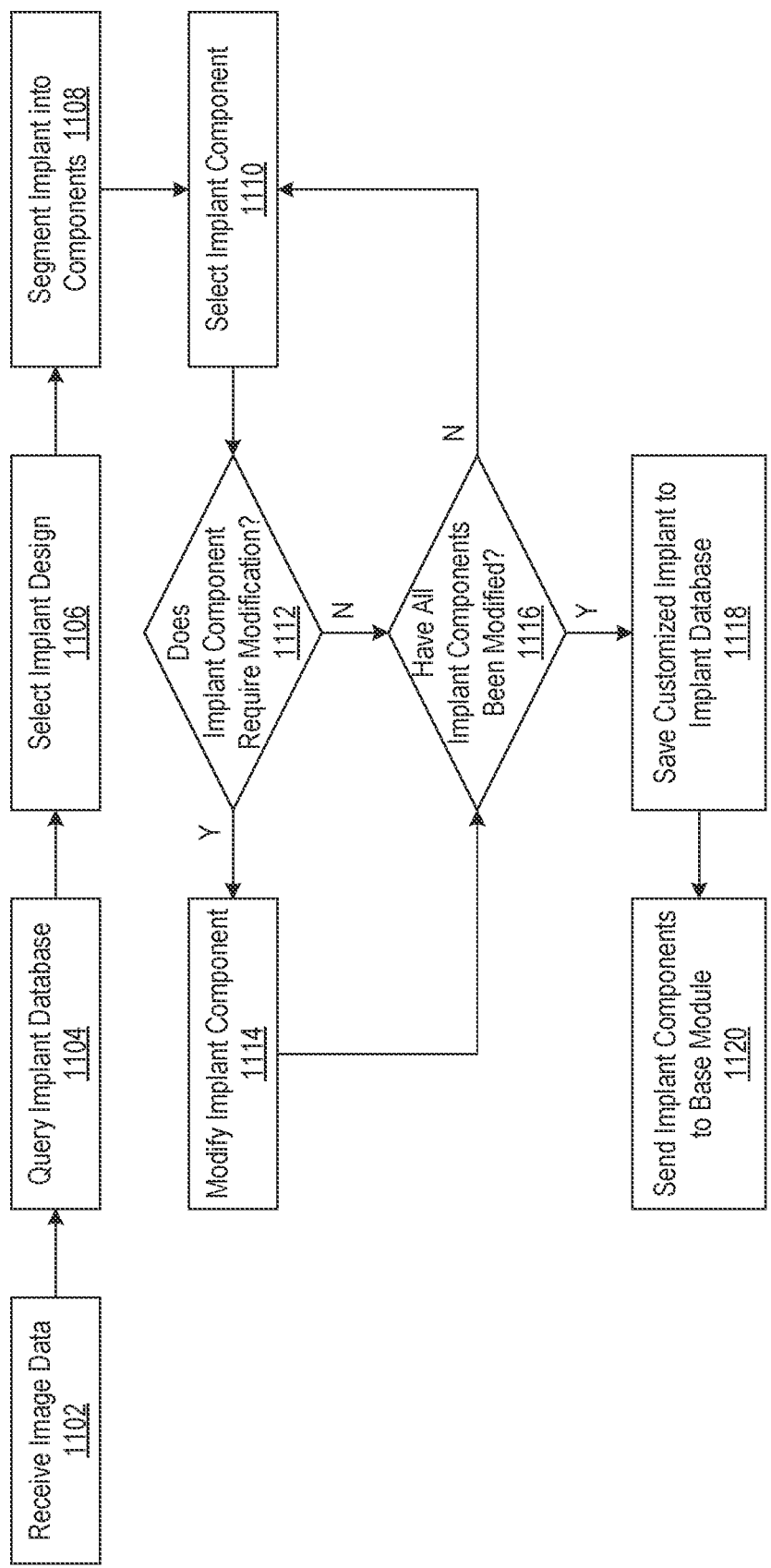
FIG. 11 is a flow diagram illustrating an example process for performing route planning for robotic surgical implant installation, in accordance with one or more embodiments.

FIG. 11 is a flow diagram illustrating an example process for performing route planning for robotic surgical implant installation, in accordance with one or more embodiments. An example operating room 102 is illustrated and described in more detail with reference to FIG. 1. In embodiments, the process of FIG. 11 is performed by the operating room system base module 632. The operating room system base module 632 is illustrated and described in more detail with reference to FIG. 6. In other embodiments, the process of FIG. 11 is performed by a computer system, e.g., the example computer system 300 illustrated and described in more detail with reference to FIG. 3. Particular entities, for example, the console 108 or the robotic surgical system 160, perform some or all of the steps of the process in other embodiments. The console 108 and the robotic surgical system 160 are illustrated and described in more detail with reference to FIG. 1. Likewise, embodiments can include different and/or additional steps, or perform the steps in different orders.

FIG. 11 displays the implant module 634. In step 1102, the implant module 634 receives the image data from the base module 632. Alternatively, the implant module 634 receives a reference location or other identifying information to facilitate retrieval of the image data from the patient database 626. In embodiments, the image data can include a series of MRI images compiled into a 3D model of patient John Smith's pelvis, specifically the right-side socket of the ball joint where the femur meets the pelvis.

In step 1104, the implant module 634 queries the implant database 630 for implant 620 designs. The implant 620 designs can be specific to the type of implant 620 to be installed, such as a hip joint, or can be a category of implants 620 such as ball and socket joints. Similarly, the implant designs 620 can perform a specific structural task, such as reinforcing or fusing part of the spine. Additionally, the implant module 634 retrieves from the implant database 630 biocompatible materials that can be used in an implant 620 and their physical and chemical properties. The implant 620 may be a physical implant or a virtual implant.

In step 1106, the implant module 634 selects an implant 620 design from the designs retrieved from the implant database 630. Alternatively, an implant 620 can be completely customized to meet the physiology or needs of the patient. Such implants 620 may not be stored in the implant database 630 or may have been populated by a separate source, such as a third-party database or process accessible via the cloud, which may or may not have been saved to the implant database 630. In embodiments, the implant module 634 can select an artificial ball and socket joint that has been previously modified to fit the physiology of patient John Smith's right hip joint.

In step 1108, the implant module 634 segments the implant 620 into a plurality of implant components 622. The segmentation can be guided by data received from the simulation module 638 or the procedure module 640, which can include route parameters such that the maximum size of the implant components 622 does not exceed the smallest dimensions provided in the route parameters or other dimensions based on anatomical features. In some embodiments, the segmentation may be based upon one or more images of the patient's anatomy using image processing and edge detection techniques. In embodiments, the implant components 622 can be arbitrarily segmented, or can be segmented based upon previously delineated break points that may have been provided when the implant 620 was designed. The implant components 622 may not necessarily fit the strict definition provided by the route parameters. For example, if the minimum clearance provided by the route parameters is 1 cm×1 cm×5 cm, but an implant component 622 is 2 cm×2 cm×5 cm, the implant component 622 would require additional modifications.

In step 1110, the implant module 634 selects an implant component 622 from the plurality of implant components 622. In embodiments, the implant module 634 can select an implant component 622 that forms a quarter of the ring of the socket for the ball and socket joint intended to replace John Smith's right hip joint.

In step 1112, the implant module 634 determines whether the implant component 622 requires modification. The implant component 622 may require modification if the physical attributes of the implant component 622 exceed the route parameters received from the simulation module 638 or procedure module 640, or exceed the dimensions of spaces between anatomical structures identified using the image data. For example, an implant component 622 with dimensions of 2 cm×2 cm×5 cm would be too large to navigate the route based upon a minimum clearance of 1 cm×1 cm×5 cm. Such an implant would require modification to allow it to fit through such a space. Likewise, the space between a bone and a blood vessel may be 2 cm, requiring the implant component 622 to have a width no larger than 1 cm to allow for a clearance margin of 0.5 cm surrounding the implant component 622 while navigating through the patient's body.

In step 1114, the implant module 634 modifies the implant component 622 to achieve the necessary physical characteristics to allow compliance with the route parameters received from the simulation module 638 or the procedure module 640, or alternatively to comply with the identified dimensions of spaces between anatomical structures identified from image data. In embodiments, modifying an implant component includes replacing a solid portion of the implant component with a collapsible portion. For example, an implant component 622 with a solid volume of 2 cm×2 cm×5 cm can be changed to a collapsible structure such that in its collapsed form, the implant component 622 measures no more than 1 cm×1 cm×5 cm. Once at the implant site, however, the implant component 622 can be expanded to its original dimensions. In alternate embodiments, an implant component 622 can require modification to achieve desired physical characteristics, such as changing materials from a titanium alloy to a medical grade silicone to add more flexibility to an implant component 622. The modifications can facilitate navigation through the patient's body. In embodiments, the implant component 622 can be modified by further segmenting the implant component 622 into additional, smaller implant components 622.

In step 1116, the implant module 634 determines whether all of the implant components 622 have been modified or assessed for whether modifications are necessary. Similarly, the implant module 634 determines whether any implant components 622 remain unmodified. If more implant components 622 remain, the implant module 634 returns to step 1110 and selects an implant component 622.

In step 1118, the implant module 634 saves the customized implant 620 and implant components 622 to the implant database 630 when all of the implant components 622 have been modified or assessed for whether modifications are necessary. In step 1120, the implant module 634 sends the implant components 622 to the base module 632. The implant components 622 can include both modified and unmodified implant components 622. The implant components 622 can be modified to meet the patient's physiology, or to enable the implant component 622 to be compliant with the route parameters such that the implant components 622 can be navigated through the patient's body via the selected route.

Figure 12:
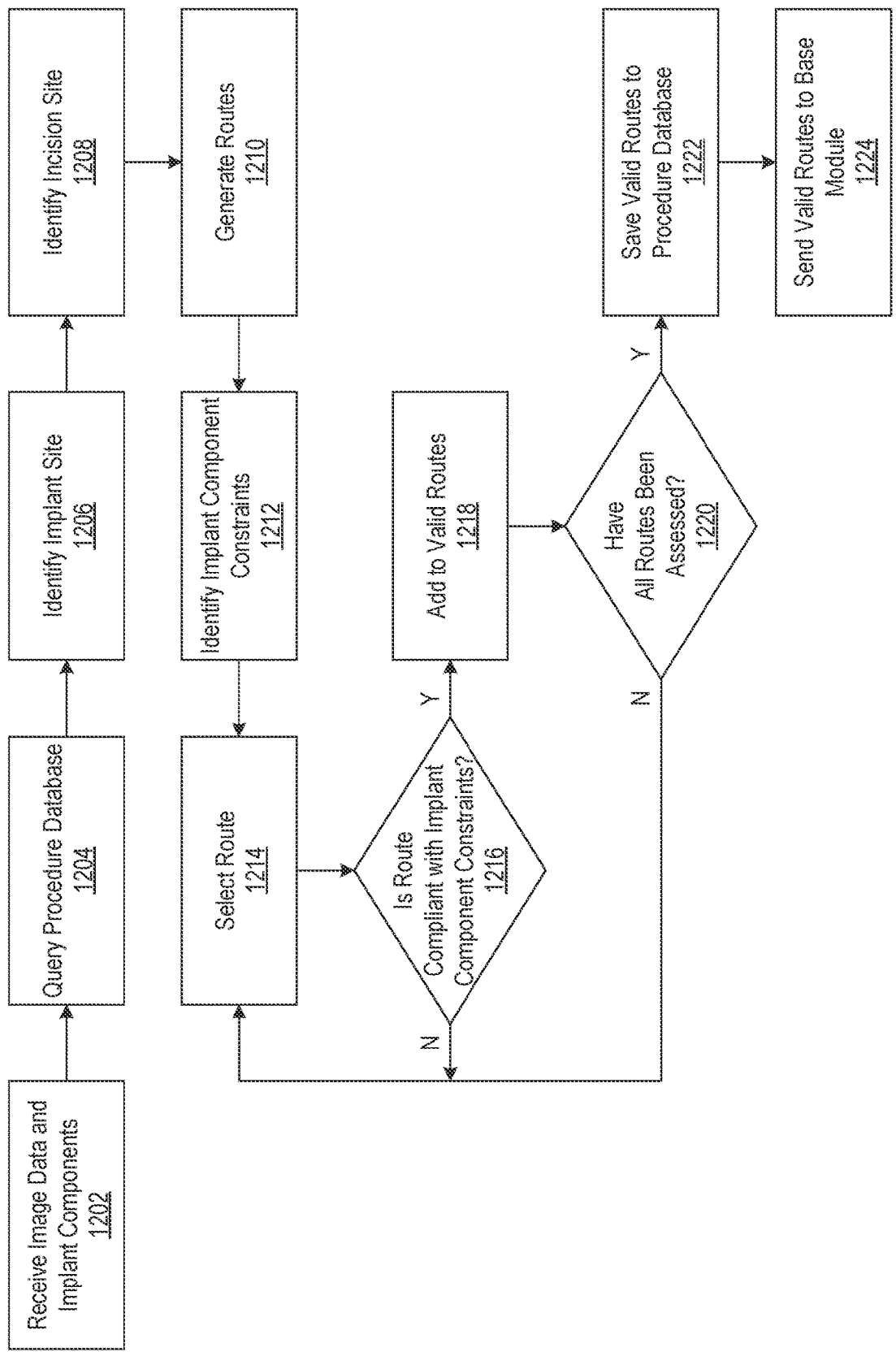
FIG. 12 is a flow diagram illustrating an example process for performing route planning for robotic surgical implant installation, in accordance with one or more embodiments.

FIG. 12 is a flow diagram illustrating an example process for performing route planning for robotic surgical implant installation, in accordance with one or more embodiments. An example operating room 102 is illustrated and described in more detail with reference to FIG. 1. In embodiments, the process of FIG. 12 is performed by the operating room system base module 624. The operating room system base module 624 is illustrated and described in more detail with reference to FIG. 6. In other embodiments, the process of FIG. 12 is performed by a computer system, e.g., the example computer system 300 illustrated and described in more detail with reference to FIG. 3. Particular entities, for example, the console 108 or the robotic surgical system 160, perform some or all of the steps of the process in other embodiments. The console 108 and the robotic surgical system 160 are illustrated and described in more detail with reference to FIG. 1. Likewise, embodiments can include different and/or additional steps, or perform the steps in different orders.

FIG. 12 displays the route planning module 636. In step 1202, the route planning module 636 receives the image data and implant components 622 from the base module 632. Alternatively, the route planning module 636 receives a reference location or other identifying information to facilitate retrieval of the image data from the patient database 626 and the implant components 622 from the implant database 630. In embodiments, the image data can include a series of MRI images compiled into a 3D model of patient John Smith's pelvis, specifically the right-side socket of the ball joint where the femur meets the pelvis, and the implant components 622 can include 12 discrete implant components 622 that, when assembled, form an implant 620.

In step 1204, the route planning module 636 queries the procedure database 628 for procedures involved in the installation of an implant. The procedures can include at least an incision site and an implant site, and can further include a route from the incision site and the implant site through which tools and implant components 622 pass during the installation of an implant 620. In embodiments, the procedures can include hip replacement procedures where a hip joint is replaced by an implant.

In step 1206, the route planning module 636 identifies an implant site where an implant 620 will be installed in a patient. The implant site can be a bone, a joint, or other anatomical structure to be removed and replaced. Alternatively, the implant site can be a void space to be occupied by an installed implant 620. The implant site can additionally include the space immediately surrounding the location where an implant 620 is to be installed. The implant site includes both the location of the implant 620 once installed and the space surrounding the implant 620, which will be used to stage and assemble the implant components 622 as well as any other tools or equipment necessary to complete the procedure. In embodiments, the implant site is John Smith's right hip and the surrounding void spaces.

In embodiments, the system 600 (see FIG. 6) identifies an incision site and an implant site within an anatomy of a patient for implant installation based on one or more images of the anatomy. For example, in step 1208, the route planning module 636 identifies incision sites. An incision site is a location through which at least some tools, equipment, implant components 622, etc., will enter the patient's body. In an ideal embodiment, the incision site refers to the point at which an implant component 622 is to enter the patient's body. For example, the system 600 uses non-invasive digital image processing for automated detection of incision sites and implant sites before or during surgery. A combination of digital image segmentation, representation, and numerical description can be employed and validated on 2-D X-ray images of the anatomy. The ML model 216 (see FIG. 2) can be used for exploration of 3D image datasets of the anatomy, e.g., obtained from a Computed Tomography (CT) or Magnetic Resonance Imaging (MRI) scanner to identify an incision site and an implant site for surgical planning. Though the examples provided may refer to and utilize a single incision site, such reference should not be construed as a limitation, as multiple incision sites can be used. Similarly, implant components 622 can be inserted through any number of incision sites in any combination. In embodiments, the route planning module 636 can select an incision site at the side of the right lower abdomen.

In step 1210, the route planning module 636 generates at least one route between the one or more incision sites and the implant site. The routes are possible paths along which a tool or implant component 622 can be navigated through the patient's body. Multiple routes can exist from the same incision site to the implant site. The routes can direct tools and implant components 622 along different paths around anatomical structures.

In embodiments, the system 600 determines route constraints for the passage of an implant component 622 from an incision site to an implant site based on the size and shape of the implant component 622. For example, in step 1212, the route planning module 636 identifies constraints on the implant components 622 such as the physical dimensions of the implant components 622 and the margins required to safely install the implant components 622, which can include varying margins depending on the type of tissues in proximity to the implant components 622. For example, an implant component can be allowed to be within 0.1 cm of a bone, but no less than 0.5 cm from nerves or blood vessels. The constraints can additionally include deployment of collapsed implant components 622 and the space required for expansion and activation of expansion. The constraints can also include the flexibility of the implant components 622 including the location and amount of flex.

In step 1214, the route planning module 636 selects a route from the generated routes that has not been assessed for compliance with the implant component 622 constraints. In step 1216, the route planning module 636 determines whether the route is compliant with implant component 622 constraints. The route is compliant if it is able to accommodate the implant components 622 including their physical dimensions, flexibility or rigidity, and the location of anatomical structures. The compliance with the implant component 622 constraints is primarily determined by analysis of and comparison with the imaging data received from the base module 632. In an ideal embodiment, the imaging data is in the form of a three-dimensional model of the patient's anatomy. The route consists of a path through the model between an incision site and an implant site, and the route is compliant if the implant component 622 constraints can be accommodated based on the imaging data. If the route is not compliant, data can be saved to the procedure database 628 with details of the route, the non-compatible implant components 622, and the constraints that the route could not accommodate. In embodiments, the route must accommodate all implant components 622. In alternate embodiments, the route must accommodate at least one implant component 622.

In step 1218, the route planning module 636 adds the selected route to a list of valid routes if the route is compliant with the implant component 622 constraints. Valid routes can accommodate the implant component 622 constraints including maintenance of safe margins in proximity to sensitive tissues such as nerves, blood vessels, organs, etc. In embodiments, a valid route can be specific to an implant component 622. The route data can additionally include a list of implant components 622 with which it is compliant, if not required to accommodate all implant components 622 to be considered a valid route. The valid routes can additionally include a score, a rank, or other form of prioritization such that the higher-scoring or higher-ranking routes indicate an increased preference, representing a higher level of accommodation for the implant components. Such scores can be applied to all implant components 622 generally or can be determined separately for each implant component 622.

In step 1220, the route planning module 636 determines whether all routes have been assessed. If all routes have not been assessed for compliance with the implant component 622 constraints, the route planning module 636 returns to step 1214 and selects another route.

In step 1222, the route planning module 636 saves the list of valid routes to the procedure database 628. The valid routes can include at least one incision site, at least one implant site, and at least one path through the patient's body from the incision site to the implant site. In embodiments, the valid routes can additionally include a list of implant components 622 for which the routes are compliant.

In step 1224, the route planning module 636 sends the list of valid routes to the base module 632. In embodiments, one of the valid routes can form a path between an incision site at the side of the right lower abdomen and an implant site at the right hip, and a path between the incision site and the right hip following just beneath the skin. The route can additionally include a list of ten implant components 622 that it is capable of accommodating.

Figure 13:
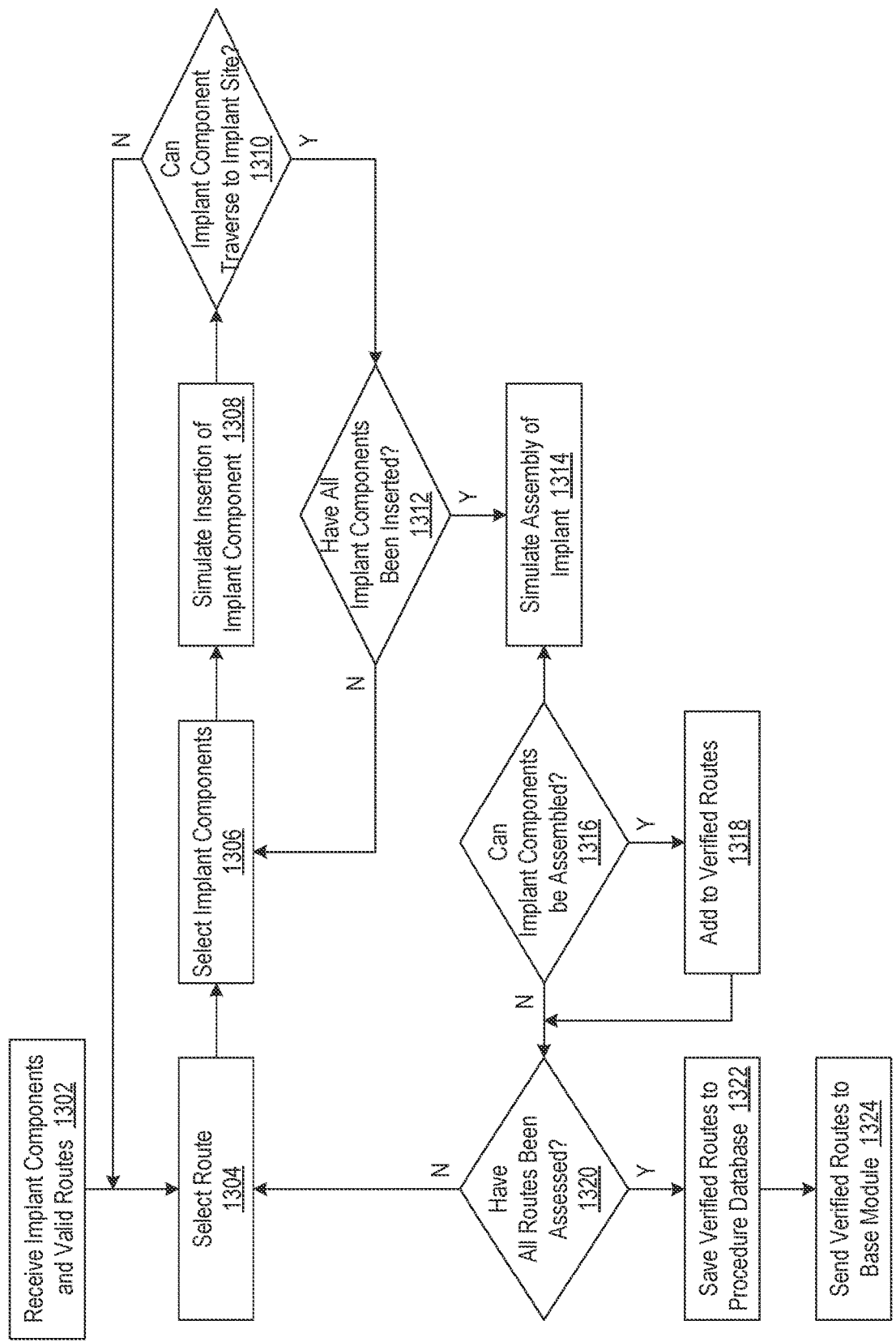
FIG. 13 is a flow diagram illustrating an example process for performing route planning for robotic surgical implant installation, in accordance with one or more embodiments.

FIG. 13 is a flow diagram illustrating an example process for performing route planning for robotic surgical implant installation, in accordance with one or more embodiments. An example operating room 102 is illustrated and described in more detail with reference to FIG. 1. In embodiments, the process of FIG. 13 is performed by the operating room system base module 632. The operating room system base module 632 is illustrated and described in more detail with reference to FIG. 6. In other embodiments, the process of FIG. 13 is performed by a computer system, e.g., the example computer system 300 illustrated and described in more detail with reference to FIG. 3. Particular entities, for example, the console 108 or the robotic surgical system 160, perform some or all of the steps of the process in other embodiments. The console 108 and the robotic surgical system 160 are illustrated and described in more detail with reference to FIG. 1. Likewise, embodiments can include different and/or additional steps, or perform the steps in different orders.

FIG. 13 displays the simulation module 638. In step 1302, the simulation module 638 receives the implant components 622 and valid routes from the base module 632. The implant components 622 are segmented and modified such that they can be navigated along a selected route from an incision site to an implant site through the patient's body where the implant components 622 can be assembled into an implant 620. The valid routes can form a path from an incision site to an implant site through the patient's body able to accommodate at least one implant component 622.

In step 1304, the simulation module 638 selects a route from the valid routes for insertion of an implant component 622. In embodiments, a route is selected that is valid for all implant components 622. In alternate embodiments, an implant component 622 is selected prior to the selection of a route such that the route is selected which is valid for the selected implant component 622. The route can be selected based on a score, a rank, or other form of prioritization such that the most suitable route is selected. Alternatively, the route can be selected arbitrarily. In embodiments, all routes, whether valid or otherwise, can be selected in turn for simulation by the simulation module 638.

In step 1306, the simulation module 638 selects an implant component 622 from the plurality of implant components 622. In embodiments, an implant component 622 is selected that forms a quarter of the ring of the socket for the ball and socket joint intended to replace John Smith's right hip joint.

In step 1308, the simulation module 638 simulates the insertion of the implant component 622 by simulating the movement of the implant component 622 from the incision site through the patient to the implant site following the selected route. The simulation can include multiple evolutions, which can include different orientations of the implant components 622 as well as variations of other insertion parameters. For example, in a second evolution, the orientation of the implant component 622 can be rotated 90 degrees relative to the orientation of the implant component 622 during the first evolution.

In step 1310, the simulation module 638 determines whether the implant component 622 can safely traverse the selected route from the incision site to the implant site. The implant component 622 is found to be unable to traverse to the implant site if it is physically unable to navigate through the body via the selected route. In embodiments, the implant component 622 has no valid paths through the body regardless of orientation. In alternate embodiments, the implant component 622 can navigate through the body, however, encroaches on the required clearances of sensitive tissues. For example, an implant component 622 may pass within 0.3 cm of a nerve, while the required clearance is no less than 0.5 cm. If the implant component 622 can successfully traverse via the selected route, the simulation module 638 checks whether all implant components 622 have been inserted. If the implant component 622 cannot be inserted, the simulation module 638 can save data related to the attempt and failure to the procedure database 628 prior to returning to step 1304 and selecting an alternate route.

In step 1312, the simulation module 638 determines whether all implant components 622 have been inserted into the patient. If simulations have not been completed for all of the implant components 622, the simulation module 638 returns to step 1306 and selects another implant component 622.

In step 1314, the simulation module 638 simulates the assembly of the implant components 622 into the final implant 620 within the patient at the implant site. The assembly is spatially constrained by the space within the patient as determined by data from the procedure database 628 and images of the patient acquired from one or more imaging devices 618.

In step 1316, the simulation module 638 determines whether the implant components 622 can be successfully assembled into the final implant 620 within the patient. The implant components 622 cannot be assembled if, similar to simulating the movement of the implant components 622 to the implant site, the implant components 622 cannot be manipulated within the implant site sufficiently to assemble the implant 620. Likewise, the implant components must maintain safe clearances from sensitive tissues such as blood vessels and nerves, unless the implant 620 is supposed to be located in close proximity to such sensitive tissues, in which case an exception can be made.

In step 1318, the simulation module 638 adds the selected route to a list of verified routes if the route could be used to insert and navigate the implant components 622 to the implant site and successfully assemble the implant components 622 into an implant. In embodiments, a verified route can be specified for each implant component 622 instead of for all implant components 622. Verified routes allow for the implant components 622 and surgical tools to maintain safe margins in proximity to sensitive tissues such as nerves, blood vessels, organs, etc. The route data can additionally include a list of implant components 622 with which the verified route is compliant if not required to accommodate all implant components 622. The verified routes can additionally include a score, a rank, or other form of prioritization such that the higher-scoring or higher-ranking routes indicate an increased preference representing a higher level of accommodation for the implant components. Such scores can be applied to all implant components 622 generally or can be determined separately for each implant component 622.

In step 1320, the simulation module 638 determines whether all routes have been simulated. If all routes have not been simulated with each of the implant component 622 constraints, the simulation module 638 returns to step 1304 and selects another route.

In step 1322, the simulation module 638 saves the list of verified routes to the procedure database 628. The verified routes include at least one incision site, at least one implant site, and at least one path through the patient's body from the incision site to the implant site. In embodiments, the verified routes can additionally include a list of implant components 622 with which the routes are compliant.

In step 1324, the simulation module 638 sends the list of verified routes to the base module 632. In embodiments, one of the verified routes consists of a path between an incision site at the side of the right lower abdomen, an implant site at the right hip, and a path between the incision site and right hip following just beneath the skin. The route can additionally include a list of ten implant components that it is capable of accommodating.

Figure 14:
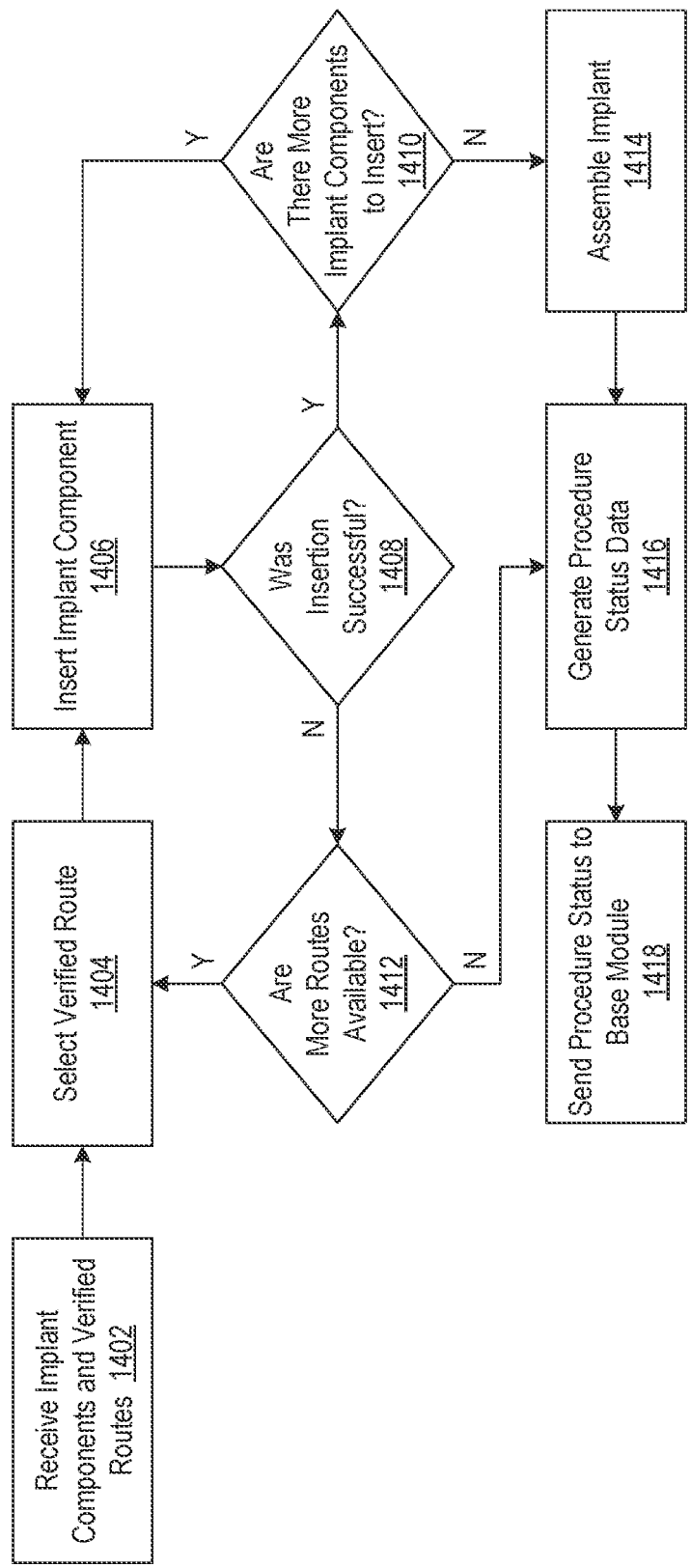
FIG. 14 is a flow diagram illustrating an example process for performing route planning for robotic surgical implant installation, in accordance with one or more embodiments.

FIG. 14 is a flow diagram illustrating an example process for performing route planning for robotic surgical implant installation, in accordance with one or more embodiments. An example operating room 102 is illustrated and described in more detail with reference to FIG. 1. In embodiments, the process 1400 of FIG. 14 is performed by the procedure module 640. The procedure module 640 is illustrated and described in more detail with reference to FIG. 6. In other embodiments, the process 1400 of FIG. 14 is performed by a computer system, e.g., the example computer system 300 illustrated and described in more detail with reference to FIG. 3. Particular entities, for example, the console 108 or the robotic surgical system 160, perform some or all of the steps of the process in other embodiments. The console 108 and the robotic surgical system 160 are illustrated and described in more detail with reference to FIG. 1. Likewise, embodiments can include different and/or additional steps, or perform the steps in different orders.

In step 1402, the procedure module 640 receives the implant components 622 and verified routes from the base module 632. The implant components 622 are segmented and modified such that they can be navigated along a selected route from an incision site to an implant site through the patient's body where the implant components 622 can be assembled into an implant 620. The verified routes consist of a path from an incision site to an implant site through the patient's body able to accommodate at least one implant component 622 that has been confirmed via simulations.

In step 1404, the procedure module 640 selects a route from the valid routes for insertion of an implant component 622. In embodiments, a route is selected that is valid for all implant components 622. In alternate embodiments, an implant component 622 is selected prior to the selection of a route such that the route is selected which has been verified for the selected implant component 622. The route can be selected based on a score, a rank, or other form of prioritization such that the most suitable route is selected. Alternatively, the route can be selected arbitrarily.

In step 1406, the procedure module 640 selects and inserts an implant component 622 from the plurality of implant components 622. In embodiments, an implant component 622 is selected that forms a quarter of the ring of the socket for the ball and socket joint intended to replace John Smith's right hip joint.

In step 1408, the procedure module 640 determines whether the implant component 622 was able to be safely maneuvered via the selected route from the incision site to the implant site. The implant component 622 is found to be unable to traverse to the implant site if it is physically unable to navigate through the body via the selected route. In embodiments, the implant component 622 has no valid paths through the body regardless of orientation. In alternate embodiments, the implant component 622 can navigate through the body but encroaches on the required clearances of sensitive tissues. For example, an implant component 622 may pass within 0.3 cm of a nerve, while the required clearance is no less than 0.5 cm. The assessment of whether the insertion of an implant component 622 was successful may be at the discretion of a surgeon, as the surgeon can use their clinical judgment to determine whether attempting to maneuver the implant component 622 may cause harm to the patient. If insertion was not successful, the procedure module 640 checks whether there are more routes available, otherwise it checks whether there are more implant components 622 to be inserted. In embodiments, minor modifications to the implant components 622 can be required. Such modifications may or may not constitute a failure of the implant component 622 depending upon whether the implant component 622 can be maneuvered to the implant site and additionally whether the implant component 622 can perform its original function upon arrival at the implant site.

In step 1410, the procedure module 640 determines whether there are more implant components 622 remaining to be inserted into the patient. If there are more implant components 622, the procedure module 640 proceeds to assemble the implant 620, otherwise, returns to step 1406 and selects and inserts the next implant component 622.

In step 1412, the procedure module 640 determines whether there are more routes available that can be used to insert the implant component 622. If another route is available, the procedure module 640 returns to step 1404 and selects another route. If no other routes are available, the procedure module 640 proceeds to step 1416 to generate procedure status data. The procedure status data indicates that the procedure is in progress and there are no remaining routes available. The procedure status can reference the specific implant component 622 that could not be successfully inserted and can additionally include data relevant to the failure, such as anatomical structures past which the implant component 622 could not be navigated. Such data can be automatically collected from at least one imaging device 618 or sensors 616, or can be provided manually by a surgeon or other medical staff.

In step 1414, the procedure module 640 assembles the implant components 622 into an implant 620 at the implant site. Should the assembly fail, the procedure module 640 generates procedure status data indicating the failure, which can be used to determine a method of assembly. In embodiments, minor modifications of the implant components 622 can be required during assembly.

In step 1416, the procedure module 640 generates procedure status data indicating the current status of the procedure. If the implant 620 is successfully assembled, a success message is generated indicating that the procedure has been successfully completed. If an implant component 622 could not be navigated to the implant site via a verified route and no routes remain to attempt, the procedure module 640 generates status data including at least the implant component, routes attempted, and any other data relevant to solving the pathfinding issue, such as the anatomical structures that prevented passage of the implant component 622, dimensions of the implant component that made it difficult to clear said anatomical structures, and any other sensitive tissues, structures, or concerns of the surgeon or other medical professionals preventing the successful insertion of the implant component 622 via one of the verified routes. Similarly, the generated procedure status data can indicate that the procedure is in progress and that a failure was encountered if the implant components 622 could not be successfully assembled, and can provide similar data indicating the components that could not be assembled and any data indicative of the issues preventing successful assembly.

In step 1418, the procedure module 640 sends the procedure status to the base module 632. The procedure status indicates that the implant components 622 have been successfully inserted and the implant 620 has been assembled and installed at the implant site. Alternatively, the procedure status can indicate that the procedure is still in progress. If the procedure is still in progress, the procedure module 640 additionally provides data indicating whether modification is required to the route of the implant components 622 or the assembly procedure for assembling the implant components 622. In embodiments, minor modifications to the implant components 622 can additionally be required.

Figure 15:
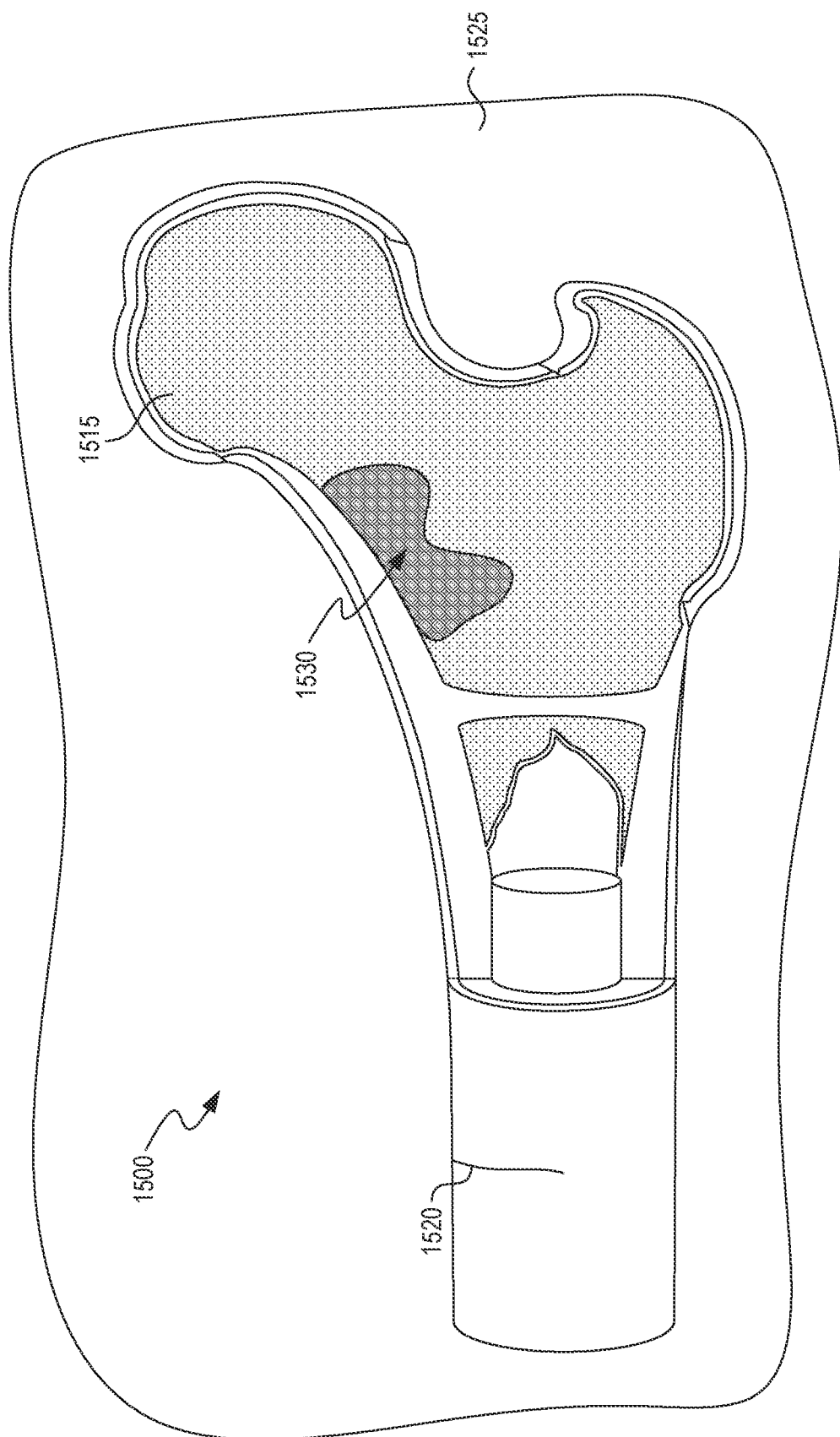
FIG. 15 illustrates an example image, in accordance with one or more embodiments.

FIG. 15 illustrates an example of an image 1500, in accordance with embodiments. The image 1500 can allow a healthcare worker to view a target region 1525 to analyze an automated diagnosis, identify anatomical features and tissues of interest, etc. Systems disclosed herein can analyze a surgical plan to identify potential one or more anatomical features of interest. The system can select imaging modalities based on the potential one or more anatomical features of interest and available imaging modalities. The system can obtain at least one image for each imaging modality and generate a multi-modality image based on each of the obtained images. The system can determine one or more imaging characteristics for each potential anatomical feature of interest and correlate imaging characteristics to identify the available imaging modalities used to select the image modalities. The system can identify anatomical features in the image 1500 (e.g., a pre-operative image, real-time intra-operative image, etc.). The multi-modality image 1500 can be generated based on a surgical plan, physician input, or other input data, and can indicate features (e.g., anatomical elements), margins, tissue type, etc.

To generate the image 1500, systems disclosed herein can receive a tissue density image from an MRI device, a bone fracture image from a CT scanner, a bone degeneration or cancerous tissue image from an ultrasound machine, or images from other imagers disclosed herein. In embodiments, the image 1500 is generated for a surgical plan for treating a damaged bone and can include, for example, tissue density data 1515 (e.g., healthy tissue data from an MRI device), a bone fracture 1520 (e.g., identified using a CT scan), diseased tissue 1530 (e.g., low-density tissue, cancerous tissue, etc., from ultrasound images), or the like. The system can combine the data to generate the image 1500 with features and/or information of interest. In embodiments, the image 1500 highlights regions 1525 of a tissue sample according to the diagnoses and/or the values from a multi-modality device or multiple imaging devices. For example, the image 1500 can annotate, highlight, and/or otherwise identify/emphasize features of interest. The emphasis can help direct the doctor's review of the target region 1525 and/or further analysis of the patient. In embodiments, images are generated that include raw data and multi-modality images (e.g., composite images, a multi-layer overlaid image, etc.) to allow a physician to perform an independent diagnosis. In embodiments, the raw data is indicated via differences in shading, color, fill patterns, express indications, display tables, selectable displays, and/or in any other suitable manner.

The multi-modality images can include selectable layers. For example, the multi-modality images can include a first layer created using a first modality, a second layer created using a second modality, and a third layer created using a third modality. A composite layer can include selected data from one or more of the three layers. The number of layers, number of imaging modalities, types of imaging modalities, data sets, fused data sets, and/or image processing (e.g., scaling of images, filtering of images, etc.) can be selected based on target characteristics of the composite layer and surgical plan (e.g., features of interest, anatomical elements, etc.). For example, the image 1500 of FIG. 15 can include selectable layers, each with one or more anatomical features identified (e.g., via annotation, false colors, etc.).

The functions performed in the processes and methods can be implemented in differing order. Furthermore, the outlined steps and operations are only provided as examples, and some of the steps and operations can be optional, combined into fewer steps and operations, or expanded into additional steps and operations without detracting from the essence of the disclosed embodiments.

The techniques introduced here can be implemented by programmable circuitry (e.g., one or more microprocessors), software and/or firmware, special-purpose hardwired (i.e., non-programmable) circuitry, or a combination of such forms. Special-purpose circuitry can be in the form of one or more application-specific integrated circuits (ASICs), programmable logic devices (PLDs), field-programmable gate arrays (FPGAs), etc.

The description and drawings herein are illustrative and are not to be construed as limiting. Numerous specific details are described to provide a thorough understanding of the disclosure. However, in certain instances, well-known details are not described in order to avoid obscuring the description. Further, various modifications can be made without deviating from the scope of the embodiments.

The terms used in this specification generally have their ordinary meanings in the art, within the context of the disclosure, and in the specific context where each term is used. Certain terms that are used to describe the disclosure are discussed above, or elsewhere in the specification, to provide additional guidance to the practitioner regarding the description of the disclosure. For convenience, certain terms can be highlighted, for example using italics and/or quotation marks. The use of highlighting has no influence on the scope and meaning of a term; the scope and meaning of a term is the same, in the same context, whether or not it is highlighted. It will be appreciated that the same thing can be said in more than one way. One will recognize that "memory" is one form of a "storage" and that the terms can on occasion be used interchangeably.

Consequently, alternative language and synonyms can be used for any one or more of the terms discussed herein, and no special significance is to be placed upon whether or not a term is elaborated or discussed herein. Synonyms for certain terms are provided. A recital of one or more synonyms does not exclude the use of other synonyms. The use of examples anywhere in this specification, including examples of any term discussed herein, is illustrative only and is not intended to further limit the scope and meaning of the disclosure or of any exemplified term. Likewise, the disclosure is not limited to various embodiments given in this specification.

It is to be understood that the embodiments and variations shown and described herein are merely illustrative of the principles of this invention and that various modifications can be implemented by those skilled in the art.

We claim:

1. A computer-implemented digital image analysis method for robotic installation of a surgical implant, comprising:
   receiving one or more images of an anatomy of a patient using one or more imaging devices;
   identifying an incision site and an implant site within the anatomy for the robotic installation based on the one or more images;
   generating, based on the one or more images, a virtual anatomy comprising a virtual incision site and a virtual implant site corresponding to the incision site and the implant site, respectively;
   virtually segmenting a surgical implant design for the surgical implant into a plurality of virtual implant components based on the one or more images such that each virtual implant component has a virtual size and a virtual shape compatible with the virtual implant site;
   determining route constraints for passage of the each virtual implant component from the virtual incision site to the virtual implant site based on the virtual size and the virtual shape;
   determining one or more routes from the virtual incision site to the virtual implant site based on the route constraints;
   virtually simulating the passage of the plurality of virtual implant components via the one or more routes by a surgical robot;
   selecting a route of the one or more routes via which the each virtual implant component can be passed from the virtual incision site to the virtual implant site by the surgical robot based on the virtual simulation;
   virtually inserting the each virtual implant component into the virtual anatomy via the route by the surgical robot; and
   virtually assembling, at the virtual implant site, the plurality of virtual implant components into the surgical implant design.

2. The method of claim 1, comprising:
   segmenting, based on the virtual segmentation and the virtual assembly, the surgical implant into a plurality of implant components;
   inserting each implant component of the plurality of implant components into the anatomy via the route by the surgical robot; and
   assembling, at the implant site, the plurality of implant components into the surgical implant.

3. The method of claim 1, comprising:
   determining that a virtual implant component of the plurality of virtual implant components is unable to be passed from the virtual incision site to the virtual implant site via any of the one or more routes; and
   determining one or more locations along the one or more routes through which the virtual implant component is unable to be passed.

4. The method of claim 3, comprising:
   modifying a particular route of the one or more routes such that the virtual implant component can be passed from the virtual incision site to the virtual implant site along the particular route, wherein the particular route excludes the one or more locations.

5. The method of claim 3, comprising:
   modifying the virtual implant component such that the virtual implant component can be passed from the virtual incision site to the virtual implant site along the one or more routes.

6. The method of claim 3, comprising:
   modifying the virtual segmentation such that each new implant component of a new plurality of implant components can be passed from the virtual incision site to the virtual implant site along the one or more routes.

7. The method of claim 1, wherein the route constraints are determined based on a clearance at the virtual implant site required for the virtual assembly of the plurality of virtual implant components into the surgical implant design.

8. A surgical robot for performing digital image analysis for installation of a surgical implant, comprising:
   a non-transitory computer-readable storage medium storing computer instructions, which when executed by one or more computer processors cause the surgical robot to:
   receive one or more images of an anatomy of a patient using one or more imaging devices;
   identify an incision site and an implant site within the anatomy for the robotic installation based on the one or more images;
   generate, based on the one or more images, a virtual anatomy comprising a virtual incision site and a virtual implant site corresponding to the incision site and the implant site, respectively;
   virtually segment a surgical implant design for the surgical implant into a plurality of virtual implant components based on the one or more images such that each virtual implant component has a virtual size and a virtual shape compatible with the virtual implant site;
   determine route constraints for passage of the each virtual implant component from the virtual incision site to the virtual implant site based on the virtual size and the virtual shape;
   determine one or more routes from the virtual incision site to the virtual implant site based on the route constraints;

virtually simulate the passage of the plurality of virtual implant components via the one or more routes by the surgical robot;

select a route of the one or more routes via which the each implant component can be passed from the incision site to the implant site by the surgical robot based on the virtual simulation;

virtually insert the each virtual implant component into the virtual anatomy via the route by the surgical robot; and virtually assemble, at the virtual implant site, the plurality of virtual implant components into the surgical implant design.

9. The surgical robot of claim 8, wherein the computer instructions cause the surgical robot to:

segment, based on the virtual segmentation and the virtual assembly, the surgical implant into a plurality of implant components;

insert each implant component of the plurality of implant components into the anatomy via the route by the surgical robot; and assemble, at the implant site, the plurality of implant components into the surgical implant.

10. The surgical robot of claim 8, wherein the computer instructions cause the surgical robot to:

determine that a virtual implant component of the plurality of virtual implant components is unable to be passed from the virtual incision site to the virtual implant site via any of the one or more routes; and determine one or more locations along the one or more routes through which the virtual implant component is unable to be passed.

11. The surgical robot of claim 10, wherein the computer instructions cause the surgical robot to:

modify a particular route of the one or more routes such that the virtual implant component can be passed from the virtual incision site to the virtual implant site along the particular route, wherein the particular route excludes the one or more locations.

12. The surgical robot of claim 10, wherein the computer instructions cause the surgical robot to:

modify the virtual implant component such that the virtual implant component can be passed from the virtual incision site to the virtual implant site along the one or more routes.

13. The surgical robot of claim 10, wherein the computer instructions cause the surgical robot to:

modify the virtual segmentation such that each new implant component of a new plurality of implant components can be passed from the virtual incision site to the virtual implant site along the one or more routes.

14. The surgical robot of claim 8, wherein the route constraints are determined based on a clearance at the virtual implant site required for the virtual assembly of the plurality of virtual implant components into the surgical implant design.

15. A system for performing digital image analysis for robotic installation of a surgical implant, comprising:

one or more computer processors; and a non-transitory computer-readable storage medium storing computer instructions, which when executed by the one or more computer processors cause the system to:

receive one or more images of an anatomy of a patient using one or more imaging devices;

identify an incision site and an implant site within the anatomy for the robotic installation based on the one or more images;

generate, based on the one or more images, a virtual anatomy comprising a virtual incision site and a virtual implant site corresponding to the incision site and the implant site, respectively;

virtually segment a surgical implant design for the surgical implant into a plurality of virtual implant components based on the one or more images such that each virtual implant component has a virtual size and a virtual shape compatible with the virtual implant site;

determine route constraints for passage of the each virtual implant component from the virtual incision site to the virtual implant site based on the virtual size and the virtual shape;

determine one or more routes from the virtual incision site to the virtual implant site based on the route constraints;

virtually simulate the passage of the plurality of virtual implant components via the one or more routes by a surgical robot;

select a route of the one or more routes via which the each virtual implant component can be passed from the virtual incision site to the virtual implant site by the surgical robot based on the virtual simulation;

virtually insert the each virtual implant component into the virtual anatomy via the route by the surgical robot; and virtually assemble, at the virtual implant site, the plurality of virtual implant components into the surgical implant design.

16. The system of claim 15, wherein the computer instructions cause the system to:

segment, based on the virtual segmentation and the virtual assembly, the surgical implant into a plurality of implant components;

insert each implant component of the plurality of implant components into the anatomy via the route by the surgical robot; and assemble, at the implant site, the plurality of implant components into the surgical implant.

17. The system of claim 15, wherein the computer instructions cause the system to:

determine that a virtual implant component of the plurality of virtual implant components is unable to be passed from the virtual incision site to the virtual implant site via any of the one or more routes; and determine one or more locations along the one or more routes through which the virtual implant component is unable to be passed.

18. The system of claim 17, wherein the computer instructions cause the system to:

modify a particular route of the one or more routes such that the virtual implant component can be passed from the virtual incision site to the virtual implant site along the particular route, wherein the particular route excludes the one or more locations.

19. The system of claim 17, wherein the computer instructions cause the system to:

modify the virtual implant component such that the virtual implant component can be passed from the incision site to the implant site along the one or more routes.

20. The system of claim 15, wherein the computer instructions cause the system to:

modify the virtual segmentation such that each new implant component of a new plurality of implant components can be passed from the virtual incision site to the virtual implant site along the one or more routes.

\* \* \* \* \*